(12) United States Patent
Larson et al.

(10) Patent No.: US 10,350,080 B2
(45) Date of Patent: Jul. 16, 2019

(54) SYSTEMS FOR DISTRACTING UNCINATE JOINTS

(71) Applicant: UNCINATE JOINT, LLC, Coeur d'Alene, ID (US)

(72) Inventors: Jeffrey John Larson, Coeur d'Alene, ID (US); Theodore P. Bertele, Longmont, CO (US)

(73) Assignee: UNCINATE JOINT, LLC, Coeur d'Alene, ID (US)

( * ) Notice: Subject to any disclaimer, the term of this patent is extended or adjusted under 35 U.S.C. 154(b) by 0 days.

(21) Appl. No.: 15/687,945

(22) Filed: Aug. 28, 2017

(65) Prior Publication Data

US 2017/0354515 A1    Dec. 14, 2017

Related U.S. Application Data

(63) Continuation of application No. 15/553,556, filed as application No. PCT/US2016/019896 on Feb. 26, 2016.

(Continued)

(51) Int. Cl.
    *A61F 2/44*           (2006.01)
    *A61B 17/70*         (2006.01)
    (Continued)

(52) U.S. Cl.
    CPC .......... *A61F 2/4405* (2013.01); *A61B 17/025* (2013.01); *A61B 17/7058* (2013.01); *A61B 17/7062* (2013.01); *A61B 17/8014* (2013.01); *A61F 2/2846* (2013.01); *A61F 2/446* (2013.01); *A61F 2/4455* (2013.01); *A61F 2/4611* (2013.01); *A61B 17/0218* (2013.01); *A61B 2017/0256* (2013.01); *A61B 2017/564* (2013.01); *A61B 2017/681* (2013.01); *A61F 2/4684* (2013.01); *A61F 2002/2835* (2013.01);
(Continued)

(58) Field of Classification Search
    CPC ........................ A61F 2/4611; A61F 2/4405; A61F 2002/448; A61F 2/4455; A61F 2/447; A61B 2017/0256
    See application file for complete search history.

(56) References Cited

U.S. PATENT DOCUMENTS 5,609,635 A      3/1997    Michelson
6,039,761 A *   3/2000    Li ........................ A61B 17/70
                                                                       623/17.16

(Continued)

FOREIGN PATENT DOCUMENTS

WO      WO 02/41811 A1    5/2002
WO      WO 2016138451 A1    2/2016

OTHER PUBLICATIONS

U.S. Appl. No. 15/553,556 Non-Final Rejection dated Apr. 11, 2018, 11 pages.

(Continued)

*Primary Examiner* — Julianna N Harvey
(74) *Attorney, Agent, or Firm* — Lathrop Gage LLP

(57) ABSTRACT

A system for distracting uncinate joints of a cervical spine segment includes two tapered elements and an actuator configured to couple with the tapered elements and change distance between the tapered elements, to insert the tapered elements into the uncinate joints, respectively, from the intervertebral disc space of the cervical spine segment.

15 Claims, 24 Drawing Sheets

Related U.S. Application Data

(60) Provisional application No. 62/121,260, filed on Feb. 26, 2015.

(51) Int. Cl.
  | | | |
  |---|---|---|
  | *A61F 2/46* | (2006.01) | |
  | *A61B 17/02* | (2006.01) | |
  | *A61B 17/80* | (2006.01) | |
  | *A61F 2/28* | (2006.01) | |
  | *A61B 17/56* | (2006.01) | |
  | *A61F 2/30* | (2006.01) | |
  | *A61B 17/68* | (2006.01) | |

(52) U.S. Cl.
  CPC ............... *A61F 2002/3055* (2013.01); *A61F 2002/30062* (2013.01); *A61F 2002/3085* (2013.01); *A61F 2002/3093* (2013.01); *A61F 2002/30433* (2013.01); *A61F 2002/30579* (2013.01); *A61F 2002/30624* (2013.01); *A61F 2002/30754* (2013.01); *A61F 2002/30985* (2013.01); *A61F 2002/448* (2013.01); *A61F 2002/4475* (2013.01); *A61F 2002/4635* (2013.01); *A61F 2310/00017* (2013.01); *A61F 2310/00023* (2013.01); *A61F 2310/00029* (2013.01); *A61F 2310/00059* (2013.01)

(56) References Cited

U.S. PATENT DOCUMENTS

| | | | |
|---|---|---|---|
| 6,090,143 | A | 7/2000 | Meriwether |
| 6,210,412 | B1 | 4/2001 | Michelson |
| 6,723,126 | B1 | 4/2004 | Berry |
| 7,494,463 | B2 | 2/2009 | Nehls |
| 8,070,782 | B2 | 12/2011 | McKay |
| 8,663,293 | B2 | 3/2014 | Assell et al. |
| 2002/0099444 | A1 | 7/2002 | Boyd et al. |
| 2002/0111679 | A1 | 8/2002 | Zucherman |
| 2002/0128717 | A1 | 9/2002 | Alfaro et al. |
| 2002/0156478 | A1* | 10/2002 | Bonutti ............... A61B 17/562 606/86 R |
| 2003/0055430 | A1 | 3/2003 | Kim |
| 2004/0176764 | A1 | 9/2004 | Dant |
| 2005/0187626 | A1 | 8/2005 | McKay et al. |
| 2005/0192669 | A1 | 9/2005 | Zdeblick et al. |
| 2006/0089646 | A1 | 4/2006 | Bonutti |
| 2007/0083266 | A1 | 4/2007 | Lang |
| 2007/0100212 | A1 | 5/2007 | Pimenta et al. |
| 2007/0265627 | A1 | 11/2007 | Dorchak et al. |
| 2007/0282448 | A1 | 12/2007 | Abdou |
| 2009/0043394 | A1 | 2/2009 | Zdeblick et al. |
| 2009/0276045 | A1 | 11/2009 | Lang |
| 2010/0152793 | A1 | 6/2010 | Lowry et al. |
| 2012/0185048 | A1 | 7/2012 | Phelps |
| 2013/0053894 | A1 | 2/2013 | Gamache et al. |
| 2013/0103152 | A1 | 4/2013 | Kwon |
| 2013/0238039 | A1 | 9/2013 | Bonutti |
| 2013/0268076 | A1 | 10/2013 | Carlson et al. |
| 2014/0288565 | A1 | 9/2014 | McCormack et al. |
| 2017/0100117 | A1 | 4/2017 | Sahai et al. |
| 2017/0354516 | A1 | 12/2017 | Larson et al. |

OTHER PUBLICATIONS

PCT/US2016/019896 International Preliminary Report on Patentability dated Jan. 27, 2017, 58 pages.
PCT/US2016/019896 Response to Written Opinion dated Dec. 19, 2016, 52 pages.
PCT/US2016/019896 International Search Report and Written Opinion dated Jul. 5, 2016, 19 pages.
U.S. Appl. No. 15/688,419 Notice of Allowance dated Feb. 2, 2018, 5 pages.
U.S. Appl. No. 15/687,970 Non-Final Rejection dated Feb. 1, 2018, 11 pages.
U.S. Appl. No. 15/688,419 Non-Final Rejection dated Nov. 17, 2017, 7 pages.
U.S. Appl. No. 15/688,419, filed Aug. 28, 2017, 86 pages.
U.S. Appl. No. 15/695,375, filed Sep. 5, 2017, 150 pages.
U.S. Appl. No. 15/695,444, filed Sep. 5, 2017, 151 pages.
U.S. Appl. No. 15/694,579, filed Sep. 1, 2017, 150 pages.
U.S. Appl. No. 15/687,970 Final Rejection dated Jul. 9, 2018, 10 pages.
U.S. Appl. No. 15/553,556 Notice of Allowance dated Sep. 26, 2018, 6 pages.
U.S. Appl. No. 15/687,970 Notice of Allowance dated Oct. 10, 2018, 5 pages.
European Patent Application No. 16756491.3, Extended Search and Opinion dated Sep. 28, 2018, 11 pages.
U.S. Appl. No. 15/694,579 Office Action dated Mar. 7, 2019, 12 pages.
U.S. Appl. No. 15/695,375 Office Action dated Apr. 29, 2019, 14 pages.
U.S. Appl. No. 15/695,444 Office Action dated Apr. 29, 2019, 12 pages.

* cited by examiner

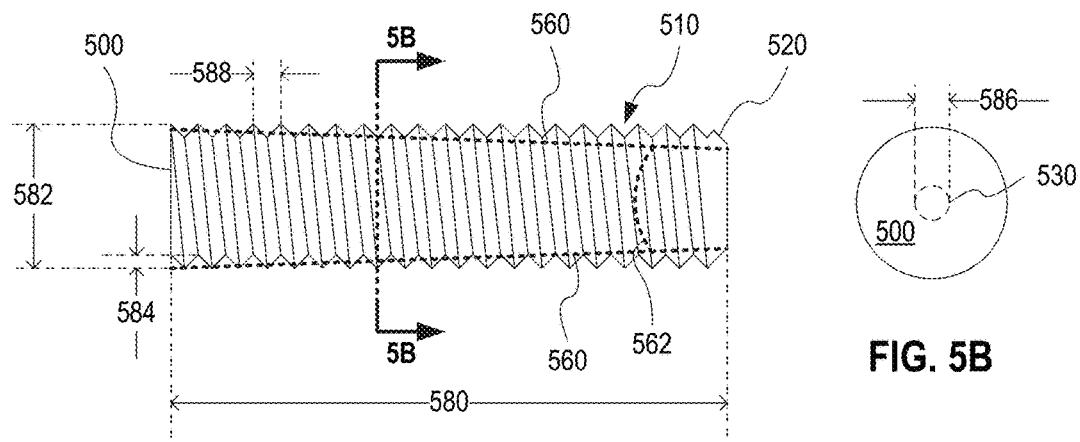
FIG. 5A
FIG. 5B
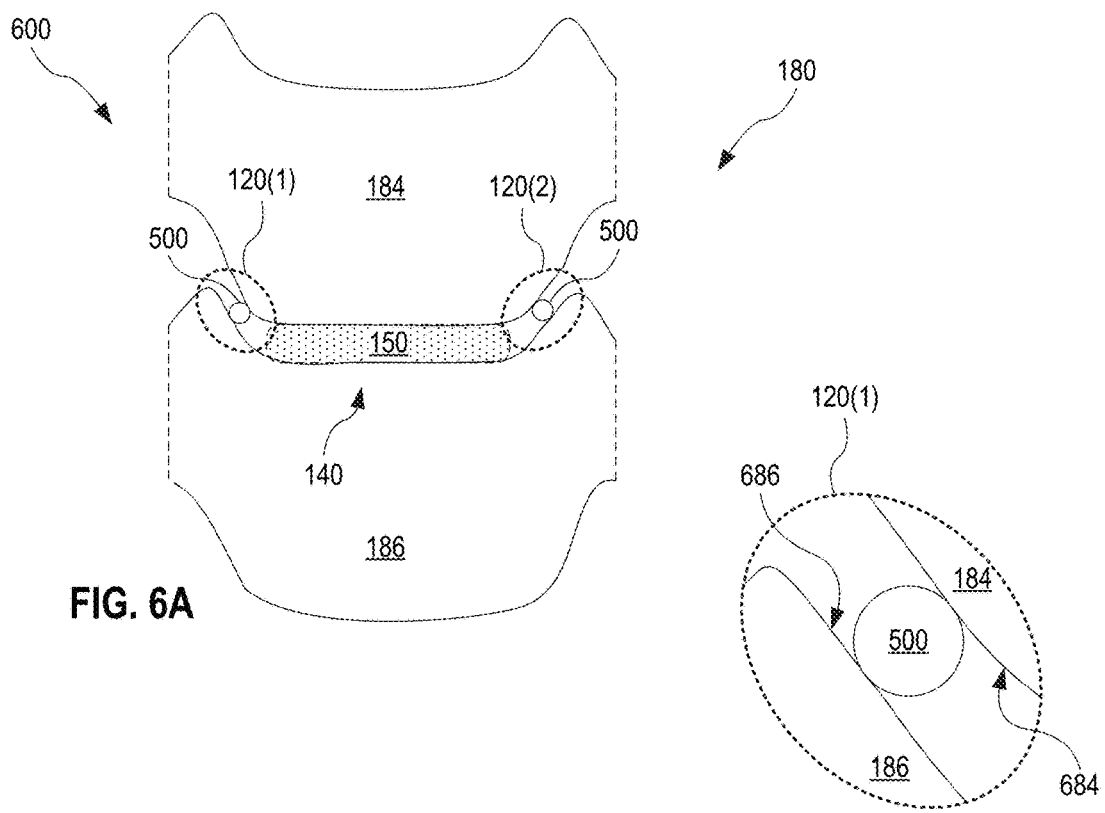
FIG. 6A
FIG. 6B

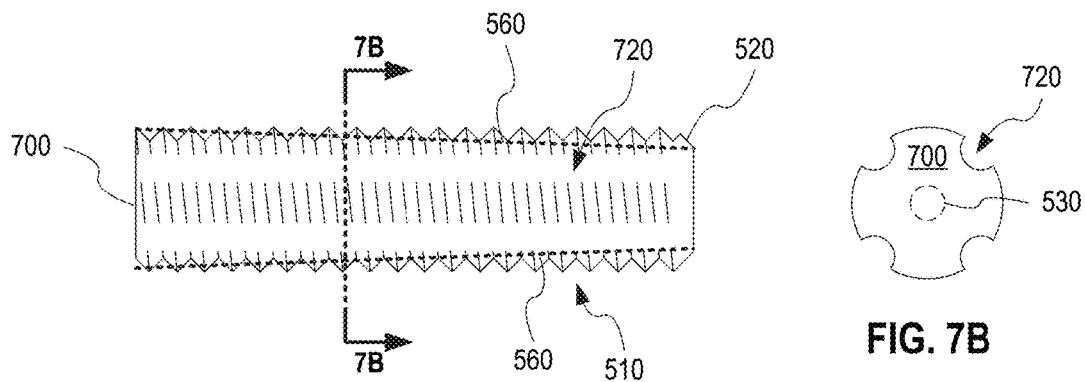
FIG. 7A
FIG. 7B
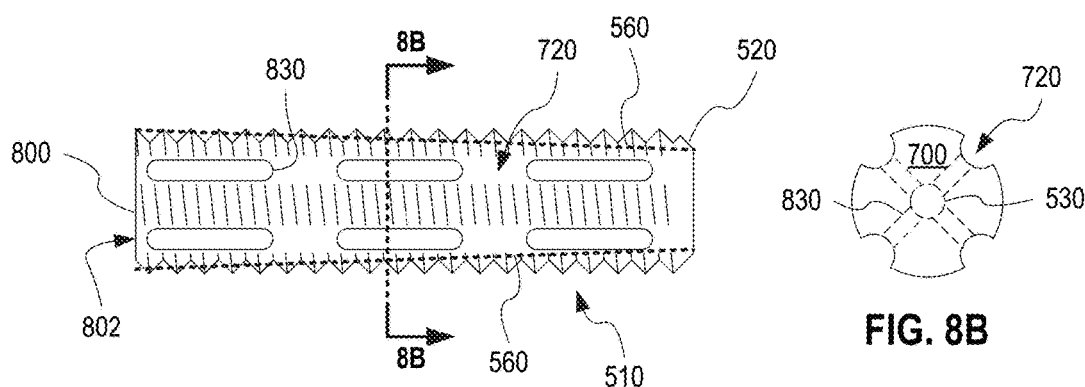
FIG. 8A
FIG. 8B
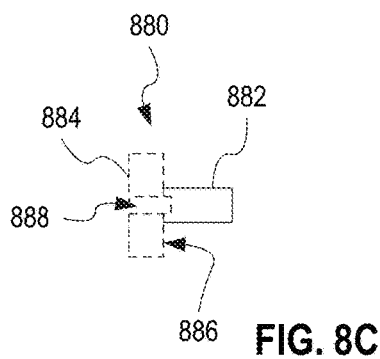
FIG. 8C
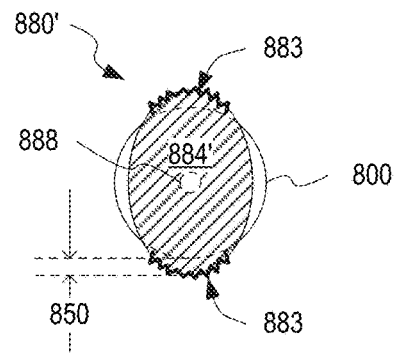
FIG. 8D

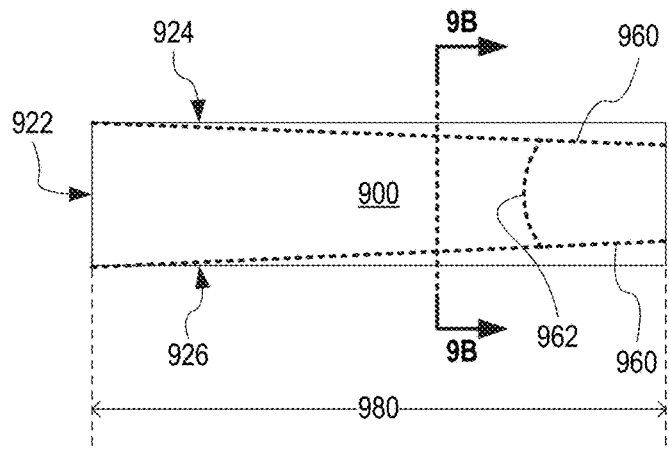
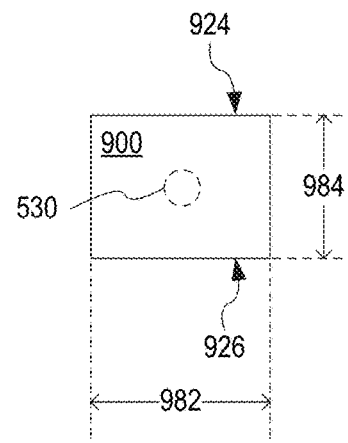
FIG. 9A  FIG. 9B
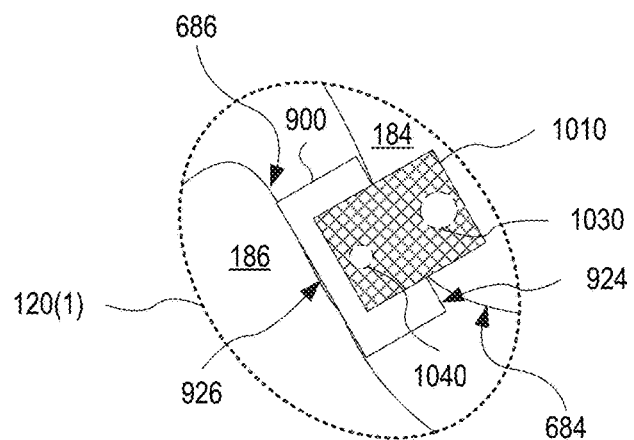
FIG. 10A
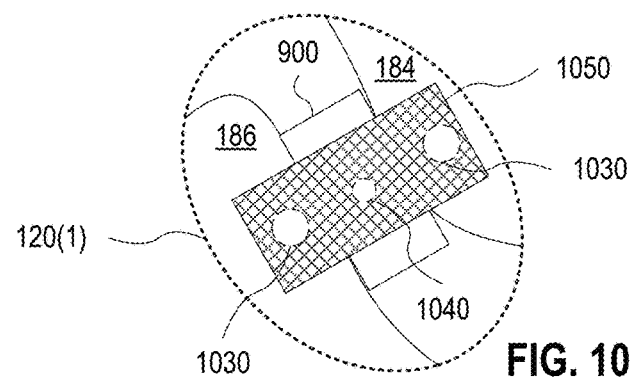
FIG. 10B

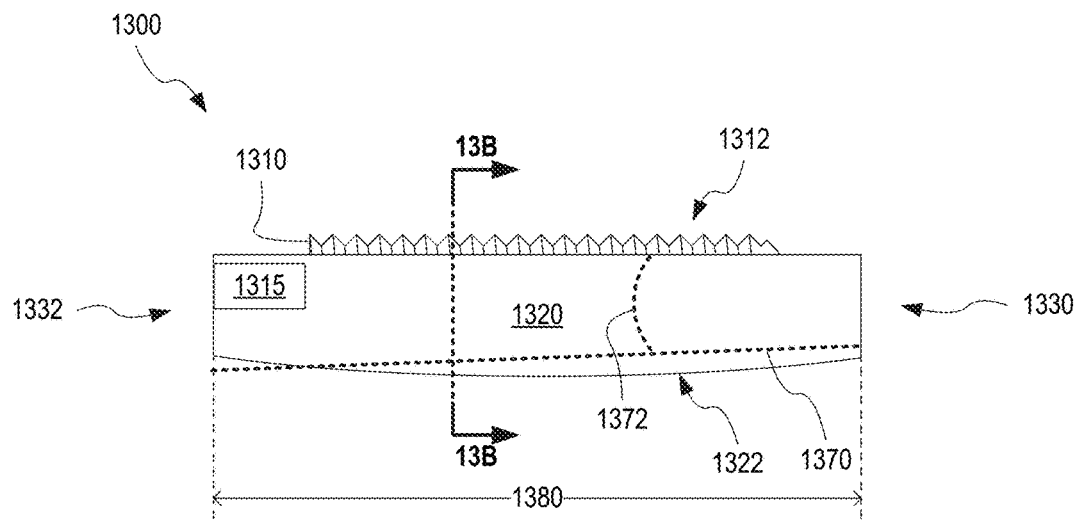
FIG. 13A
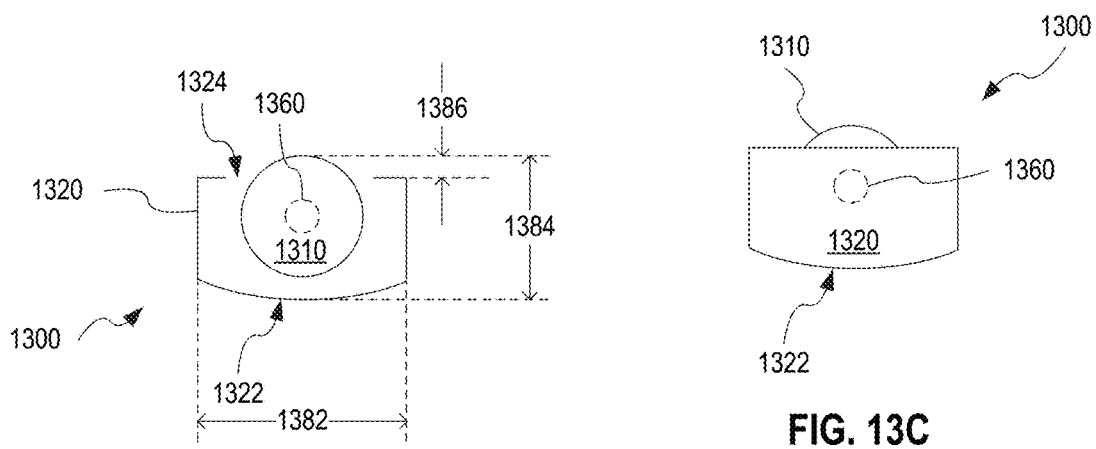
FIG. 13B
FIG. 13C
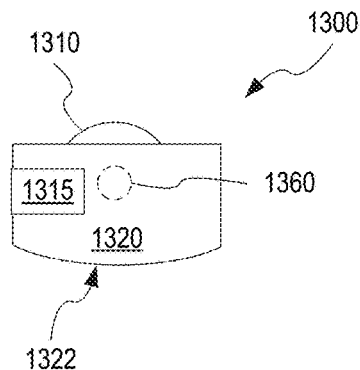
FIG. 13D

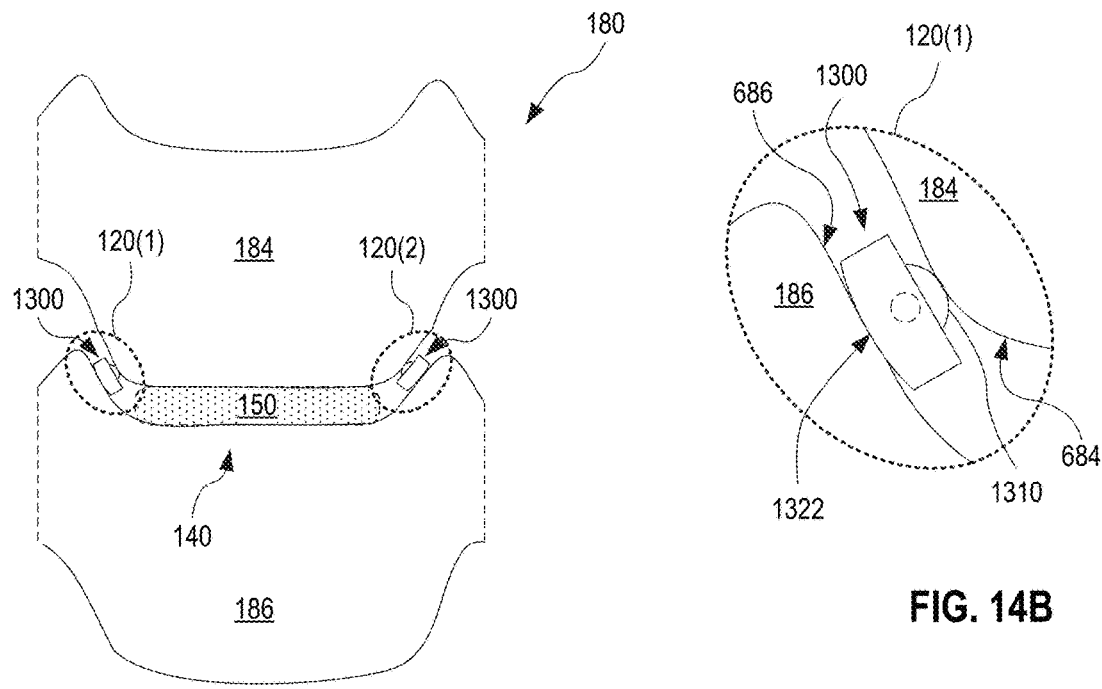
FIG. 14A
FIG. 14B
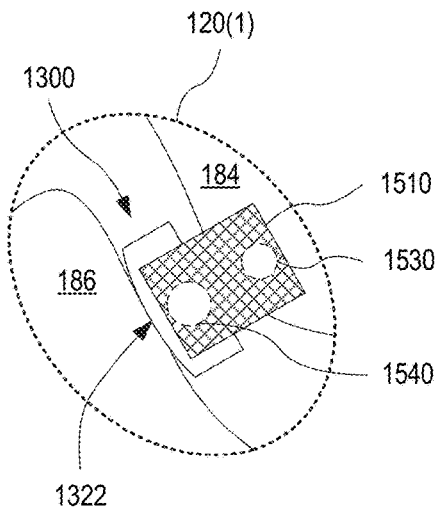
FIG. 15

SYSTEMS FOR DISTRACTING UNCINATE JOINTS

CROSS-REFERENCE TO RELATED APPLICATIONS

The present application is a continuation of U.S. patent application Ser. No. 15/553,556, filed on Aug. 24, 2017, which is a 35 U.S.C. § 371 filing of International Application No. PCT/US2016/019896, filed Feb. 26, 2016, which claims the benefit of priority from U.S. Provisional Patent Application Ser. No. 62/121,260 filed on Feb. 26, 2015. All of the aforementioned applications are incorporated herein by reference in their entireties.

BACKGROUND

The cervical spine is the neck portion of the spine. The cervical spine has a series of seven vertebrae connecting the skull to the thoracic spine (upper back). These seven vertebrae are referred to as C1-C7, with C1 being closest to the skull and C7 being furthest from the skull. Each pair of neighboring vertebrae forms a cervical spine segment that allows movement of the spine, such as rotation and flexion. Each cervical spine segment includes an intervertebral disc that separates the two vertebra to allow for smooth joint movement and provide cushioning.

The cervical spine houses the spinal cord responsible for neural communication between the brain and the body. Therefore, damage to the cervical spine can lead to neck pain, apparent pain in other parts of the body, and/or impaired functioning. For example, damage to the cervical spine may result in apparent arm pain or partial/complete loss of hand function. Although cervical spine damage may be caused by trauma, cervical spine damage usually is a gradual process occurring with aging. Common cervical spine damage includes degeneration of the intervertebral disc and degeneration of the uncinate joints located adjacent the intervertebral disc space. Intervertebral disc degeneration may cause spinal cord or nerve impingement from the formation of bone spurs and/or intervertebral disc protrusion. Uncinate joint degeneration may cause spinal cord or nerve impingement from the formation of bone spurs. Surgery may be required to resolve either of these issues.

Surgical methods used to resolve cervical spine damage traditionally include cervical discectomy (removal of intervertebral disc). The purpose of such surgery is to restore proper spacing between the cervical vertebrae of the damage cervical spine segment. The intervertebral disc may be replaced by a cage that includes bone graft material for subsequent fusion of the cervical spine segment. A fused cervical spine segment is stiff and does not allow for joint movement. Alternatively, the intervertebral disc is replaced by an artificial disc device that allows for active joint movement of the cervical spine segment.

Conventionally, cervical discectomy is performed from the front (the anterior side). To access the cervical spine segment, the surgeon (a) makes a skin incision in the front of the neck, (b) makes a tunnel to the spine by moving aside muscles and retracting the trachea, esophagus, and arteries, and (c) lifts and holds aside the longus colli muscles that support the front of the spine. Next, the surgeon screws pins into both the superior (upper) cervical vertebra and the inferior (lower) cervical vertebra of the cervical spine segment and uses these pins to increase the intervertebral spacing. The surgeon then performs the cervical discectomy and inserts a cage into the intervertebral disc space.

When the cage includes bone graft material, bone growth within the intervertebral disc space takes place over the next several months, ultimately fusing the cervical spine segment. Each vertebral body (the portion of the vertebra located above or below the intervertebral disc space) has a denser shell of cortical bone surrounding an inner, cylindrical core of spongy cancellous bone. At the intervertebral disc space, the cortical bone shell forms a ring around the cancellous bone. Fusion of the cervical spine segment requires bone growth between the two cortical bone shells of the cervical spine segment.

SUMMARY

In an embodiment, a method for stabilizing a cervical spine segment, includes implanting a respective uncinate joint stabilizer into each uncinate joint of the cervical spine segment to stabilize the uncinate joints and thereby stabilize the cervical spine segment.

In an embodiment, a system for stabilizing a cervical spine segment, includes a pair of uncinate joint stabilizers for stabilizing a respective pair of uncinate joints of the cervical spine segment. Each uncinate joint stabilizer is elongated along a lengthwise dimension and configured for placement in the respective uncinate joint with the lengthwise dimension substantially oriented along an anterior-to-posterior direction of the cervical spine segment. Each uncinate joint stabilizer has height in a heightwise dimension orthogonal to the lengthwise dimension. The height is configured to define spacing of the respective uncinate joint.

In an embodiment, a system for distracting uncinate joints of a cervical spine segment includes two tapered elements and an actuator. The actuator is configured to couple with the tapered elements and change distance between the tapered elements, to insert the tapered elements into the uncinate joints, respectively, from intervertebral disc space of the cervical spine segment.

BRIEF DESCRIPTION OF THE DRAWINGS

FIGS. 5A and 5B illustrate a threaded implant for stabilizing an uncinate joint, according to an embodiment.

FIGS. 6A and 6B depict a diagram showing, in an anterior view, a pair of the threaded implant of FIGS. 5A and 5B installed in the uncinate joints of a cervical spine segment according to the method of FIG. 4, according to an embodiment.

FIGS. 7A and 7B illustrate a fenestrated, threaded implant for stabilizing an uncinate joint, according to an embodiment.

FIGS. 8A and 8B illustrate another fenestrated, threaded implant for stabilizing an uncinate joint, according to an embodiment.

FIG. 8C illustrates a cap for sealing a through-hole of the fenestrated, threaded implant of FIGS. 8A and 8B, according to an embodiment.

FIG. 8D illustrates a cap which is an implementation of the cap of FIG. 8C, which further implements a locking lever, according to an embodiment.

FIGS. 9A and 9B illustrate a shim implant for stabilizing an uncinate joint, according to an embodiment.

FIGS. 10A and 10B illustrate, in an anterior view, the shim implant of FIGS. 9A and 9B secured to an uncinate joint using additional hardware, according to an embodiment.

FIGS. 13A, 13B, 13C, and 13D illustrate a motion-preserving implant for stabilizing an uncinate joint, according to an embodiment.

FIGS. 14A and 14B show, in an anterior view, a pair of the motion-preserving implant of FIGS. 13A-D installed in the uncinate joints of a cervical spine segment according to the method of FIG. 4, according to an embodiment.

FIG. 15 shows, in an anterior view, the motion-preserving implant of FIGS. 13A-D secured to an uncinate joint using additional hardware, according to an embodiment.

DETAILED DESCRIPTION OF THE EMBODIMENTS

Figure 1:
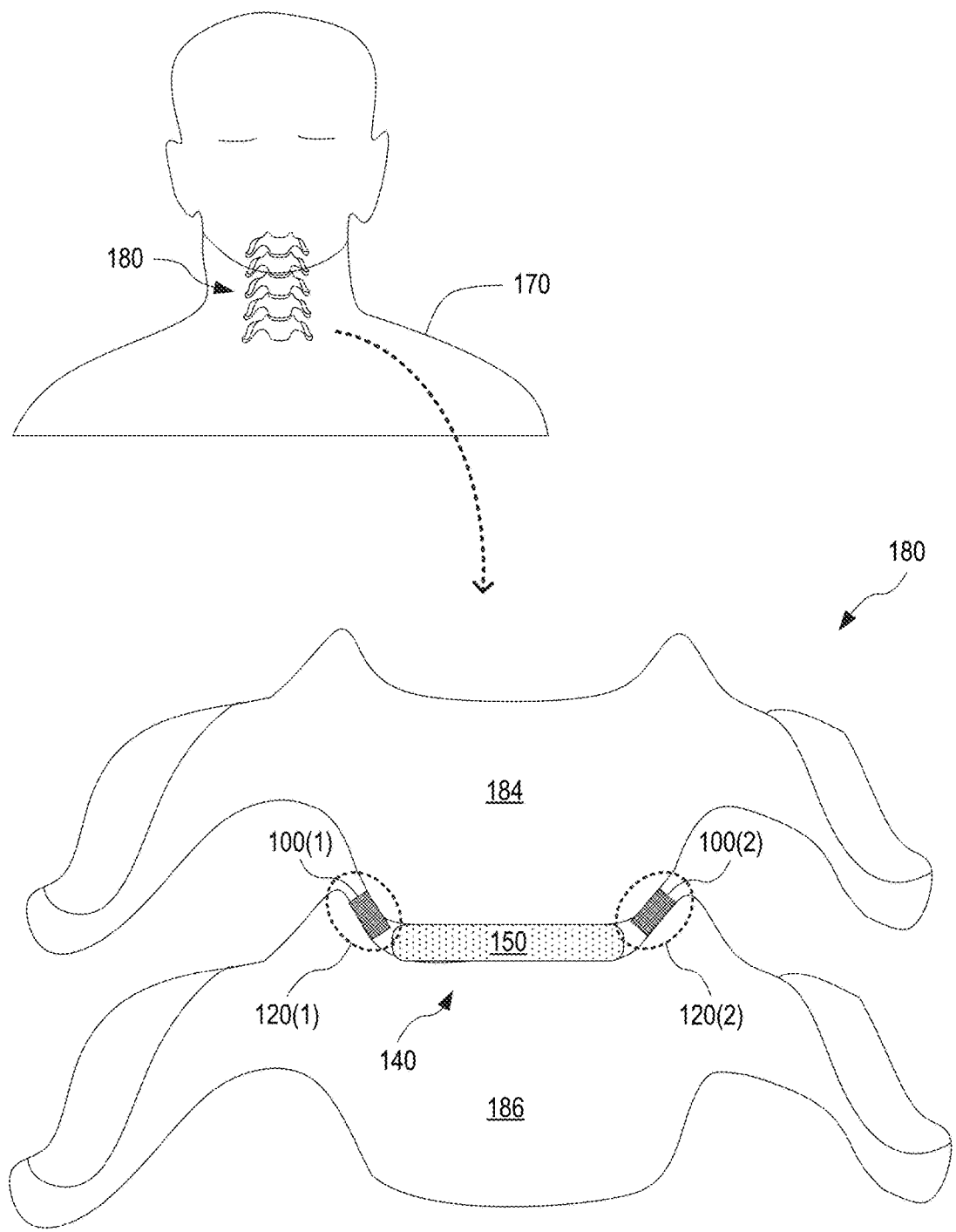
FIG. 1 illustrates implants that stabilize the uncinate joints of a cervical spine segment, according to an embodiment.

FIG. 1 illustrates two exemplary implants 100 that stabilize the uncinate joints 120 a cervical spine segment 180 of a patient 170, according to an embodiment. Implant 100 may also be referred to as an uncinate joint stabilizer. Cervical spine segment 180 includes superior vertebra 184 and inferior vertebra 186, wherein superior vertebra 184 is one of C3, C4, C5, and C6. Uncinate joints 120, also known as the uncovertebral joints or the joints of Luschka, are located adjacent the intervertebral disc space 140 of cervical spine segment 180. Uncinate joints 120 are associated with cortical bone of cervical vertebrae 184 and 186.

In one embodiment, implant 100 is a permanent implant that stays in place over the life of the patient, unless surgically removed. In another embodiment, implant 100 is biodegradable and eventually degrades. In one embodiment, implants 100 lock the mobility of cervical spine segment 180 and, optionally, include bone graft material that promotes fusion of uncinate joints 120. In one fusion-promoting example, implant 100 is porous or have cavities configured to accommodate bone graft material. In another fusion-promoting example, at least a portion of implant 100 is a porous portion composed of bone graft material that promotes bone growth in the pores thereof. Herein, "bone graft material" refers to a material that promotes bone growth. Exemplary bone graft materials include biological materials, stem cell based materials, synthetic bone growth promoting materials, other bone growth promoting materials known in the art, and a combination thereof. In another embodiment, implants 100 are motion-preserving implants that preserve at least some degree of mobility of cervical spine segment 180.

Implant 100 is notably smaller than conventional implants placed in intervertebral disc space 140. Hence, implant 100 may be less expensive, require less hardware, and be installed in uncinate joints 120 using less invasive methods than those associated with the installation of conventional implants placed in intervertebral disc space 140.

Disclosed herein are methods that insert implants 100 into uncinate joints 120 to stabilize cervical spine segment 180, while leaving intact intervertebral disc 150 located in intervertebral disc space 140. Herein, an "intact" intervertebral disc may refer to a disc that is entirely undisturbed by implants 100, or an intervertebral disc that is slightly altered by implant(s) 100 in a generally lateral dimension. In certain embodiments, the methods disclosed herein stabilize cervical spine segment 180 while preserving motion of cervical spine segment 180 and also allowing for normal health and functionality of intervertebral disc 150. These methods are, in certain embodiments, performed in a minimally invasive manner utilizing percutaneous access to uncinate joints 120. In contrast, conventional stabilization of cervical spine segment 180, based upon stabilization within intervertebral disc space 140, requires anterior access to intervertebral disc space 140, and relies on open access to intervertebral disc space 140. In one use scenario, the methods disclosed herein utilize biodegradable embodiments of implants 100, which stabilize uncinate joints 120 for a duration sufficient for healing of an injury to intervertebral disc 150, but subsequently degrades to play no or little role in the functionality of cervical spine segment 180. Also disclosed herein are methods that use implants 100 to stabilize uncinate joints 120 in conjunction with performing cervical discectomy. Whether implants 100 are used in conjunction with cervical discectomy or coexist in cervical spine segment 180 with an intact intervertebral disc 150, implants 100 may include or be substantially composed of bone graft material to promote (a) fusion of uncinate joints 120 or (b) bony ingrowth in uncinate joints 120 at the interfaces between implants 100 and one of cervical vertebrae 184 and 186. Since the surfaces of uncinate joints 120 are cortical bone, such fusion is expected to be fast and strong.

Figure 2:
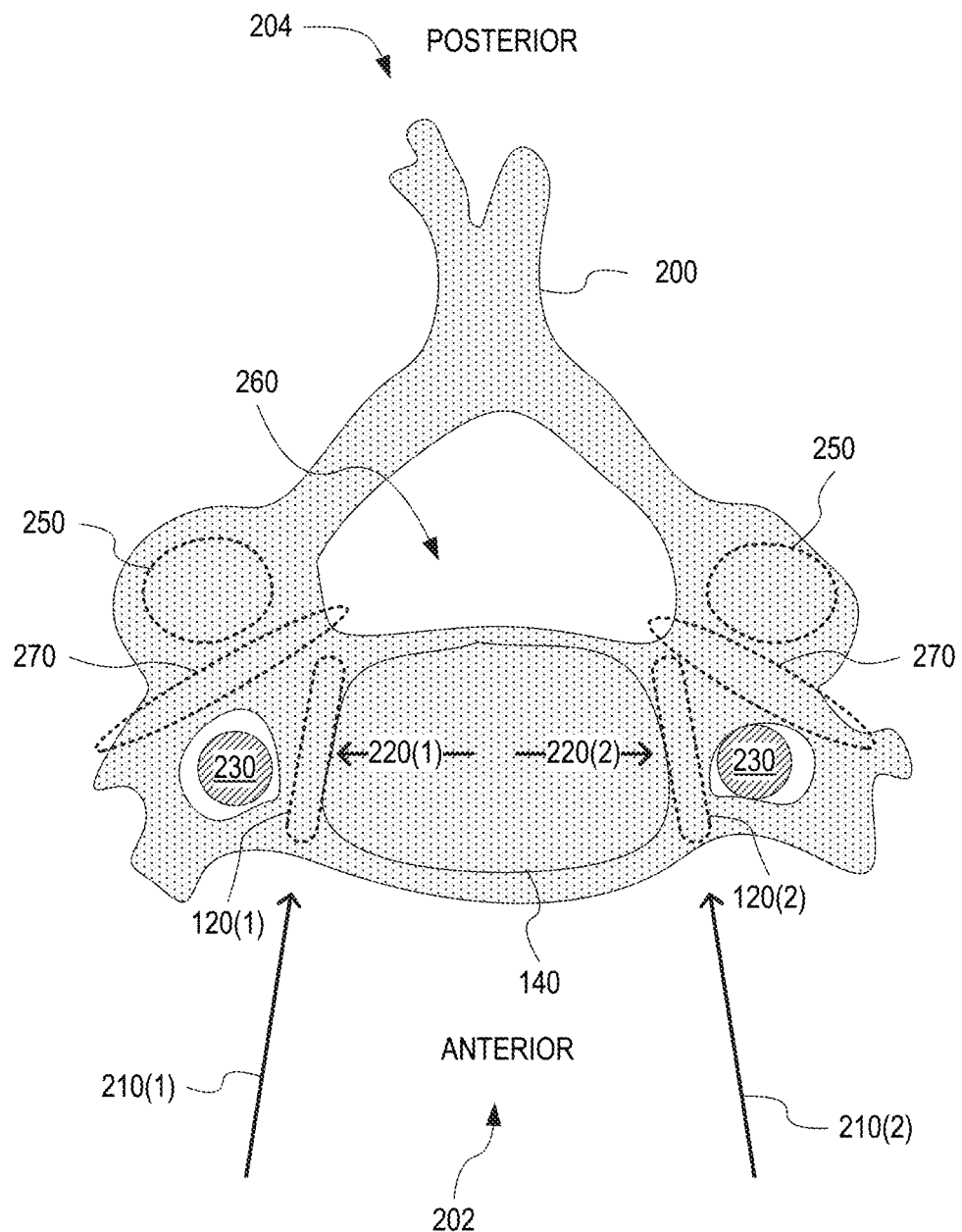
FIG. 2 shows an axial view (along the spine) of a cervical vertebra that is one of vertebra C3-C7.

FIG. 2 shows an axial view (along the spine) of a cervical vertebra 200 that is one of vertebrae C3-C7. Cervical vertebra 200 is, for example, one or cervical vertebrae 184 and 186. Label 202 indicates the anterior (front) side of cervical vertebra 200 and label 204 indicates the posterior (back) side of cervical vertebra 200. Uncinate joints 120 are located adjacent intervertebral disc space 140. Cervical vertebra 200 includes surfaces for forming facet joints 250 with a neighboring cervical vertebra 200. FIG. 2 further indicates the locations of vertebral arteries 230 passing through cervical vertebra 200. The spinal canal 260 is located posterior to intervertebral disc space 240. The spinal cord passes through spinal canal 260. Nerve roots pass through the neural foramen along paths 270.

Referring now to FIGS. 1 and 2 in combination, each implant 100 may be inserted into the respective uncinate joint 120 along an anterior-to-posterior direction 210. Herein, "anterior-to-posterior direction" refers to a direction that is generally from anterior side 202 towards posterior side 204, such that access to uncinate joint 120 along anterior-to-posterior direction 210 does not require passing through intervertebral disc space 140. Thus, when inserting implants 100 into uncinate joints 120 along anterior-to-posterior direction 210, intervertebral disc 150 may be left intact. Alternatively, each implant 100 may be inserted into the respective uncinate joint 120 along a medial-to-lateral direction 220. Herein, "medial-to-lateral direction" refers to a direction that is from intervertebral disc space 140 towards either one of uncinate joints 120. Thus, when inserting implants 100 into uncinate joints 120 along medial-to-lateral direction 220, implants 100 are inserted into uncinate joints 120 from intervertebral disc space 140.

Figure 3:
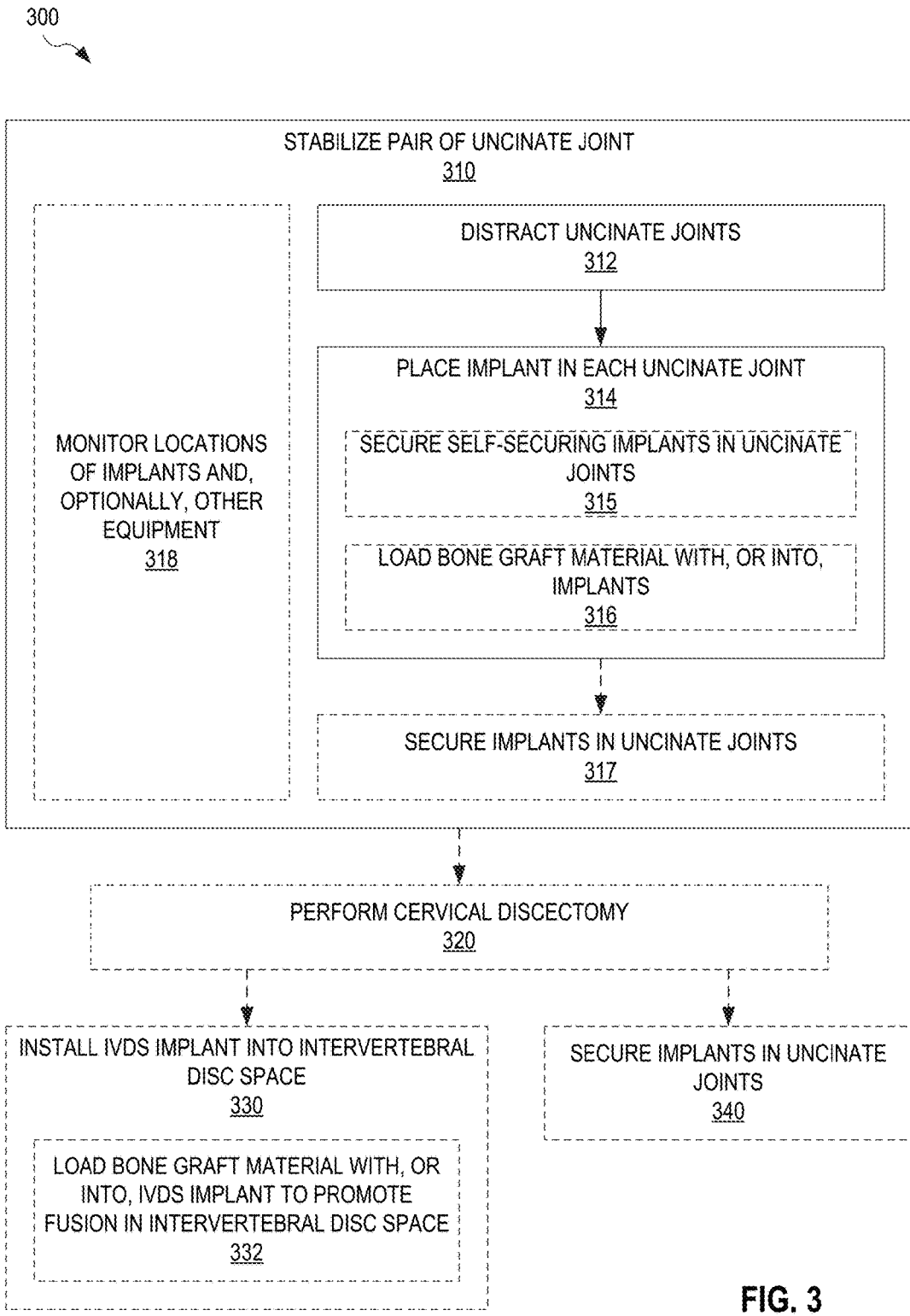
FIG. 3 illustrates a method for stabilizing a cervical spine segment by inserting implants into the uncinate joints of the cervical spine segment, according to an embodiment.

FIG. 3 illustrates one exemplary method 300 for stabilizing cervical spine segment 180 (FIG. 1) by inserting implants 100 into uncinate joints 120 of cervical spine segment 180. In method 300, uncinate joints 120 may be accessed via anterior-to-posterior directions 210 (FIG. 2) or via medial-to-lateral directions 220.

In a step 310, method 300 stabilizes uncinate joints 120. Step 310 includes steps 312 and 314. Step 312 distracts each uncinate joint 120 to prepare uncinate joints 120 for insertion of implants 100. In one example of step 312, a surgeon inserts a distraction tool into each uncinate joint 120 along anterior-to-posterior direction 210 or along medial-to-lateral directions 220, and uses this distraction tool to open uncinate joint 120. Herein, a "surgeon" may be assisted or replaced by robotic equipment without departing from the scope hereof. Step 314 places implants 100 into respective uncinate joints 120. Herein, a step of placing an implant may also be referred to as a step of implanting an uncinate joint stabilizer. In one example of step 314, a surgeon inserts implant 100 into each uncinate joint 120. Implants 100 used in step 314 may also perform step 312, and step 314 may be performed concurrently with or prior to step 312, without departing from the scope hereof.

In one implementation of method 300, implants 100 are self-securing and step 314 includes a step 315 of securing such self-securing embodiments of implants 100 in uncinate joints 120. Herein, a "self-securing" implant is an implant that stays in place without use of additional hardware. In one example, a self-securing embodiment of implant 100 has features that grip the surface of one or both of cervical vertebrae 184 and 186 at uncinate joint 120. A "self-securing" implant may secure itself at least in part by cooperation with a tension band. Herein, a "tension band" refers to one or more ligaments of cervical spine segment 180, which pull cervical vertebrae 184 and 186 toward each other. Hence, in one example of step 315, a surgeon places self-securing implants 100 in respective uncinate joints 120, where each implant 100 cooperates with respective uncinate joint 120 and, optionally, a tension band to secure itself.

In one implementation, step 314 includes a step 316 of loading bone graft material with, or into, implants 100 to promote subsequent (a) fusion of uncinate joints 120 or (b) bony ingrowth in uncinate joints 120 at interfaces between implants 100 and one of cervical vertebrae 184 and 186. In one example of step 314 implemented with step 316, a surgeon inserts, into each uncinate joint 120, an embodiment of implant 100 carrying bone graft material. In another example of step 314 implemented with step 316, a surgeon inserts, into each uncinate joint 120, an embodiment of implant 100 that has at least one void. This embodiment of implant 100 may include a porous portion, one or more fenestrations, and/or one or more cavities. Next, in this example, the surgeon loads bone graft material into the at least one void of implant 100.

In implementations of method 300 that do not utilize self-securing embodiments of implants 100, step 310 may further include a step 317 of securing implants 100 in uncinate joints 120. In one example of step 317, a surgeon secures each implant 100 to one or both of cervical vertebrae 184 and 186 using additional hardware, such as plates, screws, and/or pins.

In certain embodiments, step 310 includes a step 318 of monitoring locations of implants 100 and, optionally, equipment used to perform one, two, or all of steps 312, 314, and 317, to ensure that uncinate joints 120 are stabilized without unintentionally harming other structures. Step 318 may monitor the locations of implants 100, and optionally equipment used to handle implants 100, within patient 170 relative to the location of important structures such as vertebral arteries 230 (FIG. 2), nerve roots passing through the neural foramen (along paths 270 of FIG. 2), and spinal canal 260. In one example of step 318, real-time imaging of at least a portion of cervical spine segment 180 is performed concurrently with some or all of steps 312, 314, and 317. This real-time imaging may include fluoroscopy and/or other imaging method(s) known in the art.

Although not shown in FIG. 3, step 310 may be preceded by a step of locating uncinate joints 120, without departing from the scope hereof.

In one embodiment, method 300 further includes a step 320 of performing cervical discectomy. In one example of step 320, a surgeon removes at least the majority of intervertebral disc 150 from intervertebral disc space 140. Step 320 may utilize methods known in the art. Optionally, step 320 is followed by a step 330 that installs an intervertebral-disc-space (IVDS) implant in intervertebral disc space 140. In one implementation, step 330 includes a step 332 of loading bone graft material into intervertebral disc space 140, together with or into this IVDS implant, to promote subsequent fusion between cervical vertebrae 184 and 186 within intervertebral disc space 140. In one example of step 332, an IVDS implant, with at least one void capable of accommodating bone graft material, is inserted into intervertebral disc space 140. Bone graft material may be loaded into the void(s) prior to or after insertion of the IVDS implant into intervertebral disc space 140. In another example of step 332, the IVDS implant is a bag or malleable container with bone graft material.

In implementations of method 300 that include step 320 but do not utilize self-securing embodiments of implants 100 and also do not implement step 317, method 300 may further include a step 340, subsequent to step 320, of securing implants 100 in respective uncinate joints 120. Step 340 is, for example, performed in a manner similar to that of step 317.

Although for clarity not shown in FIG. 3, step 310 may utilize trial implants to stabilize uncinate joints 120, without departing from the scope hereof. Each such trial implant is an embodiment of implant 100, which is removed at a later stage. In one example, the trial implants are removed after step 320. When step 310 utilizes such trial implants, method 300 may include a later step of placing final implants 100 in uncinate joints 120. For example, method 300 may implement step 314 with final implants 100 after step 320 or during step 330.

Figure 4:
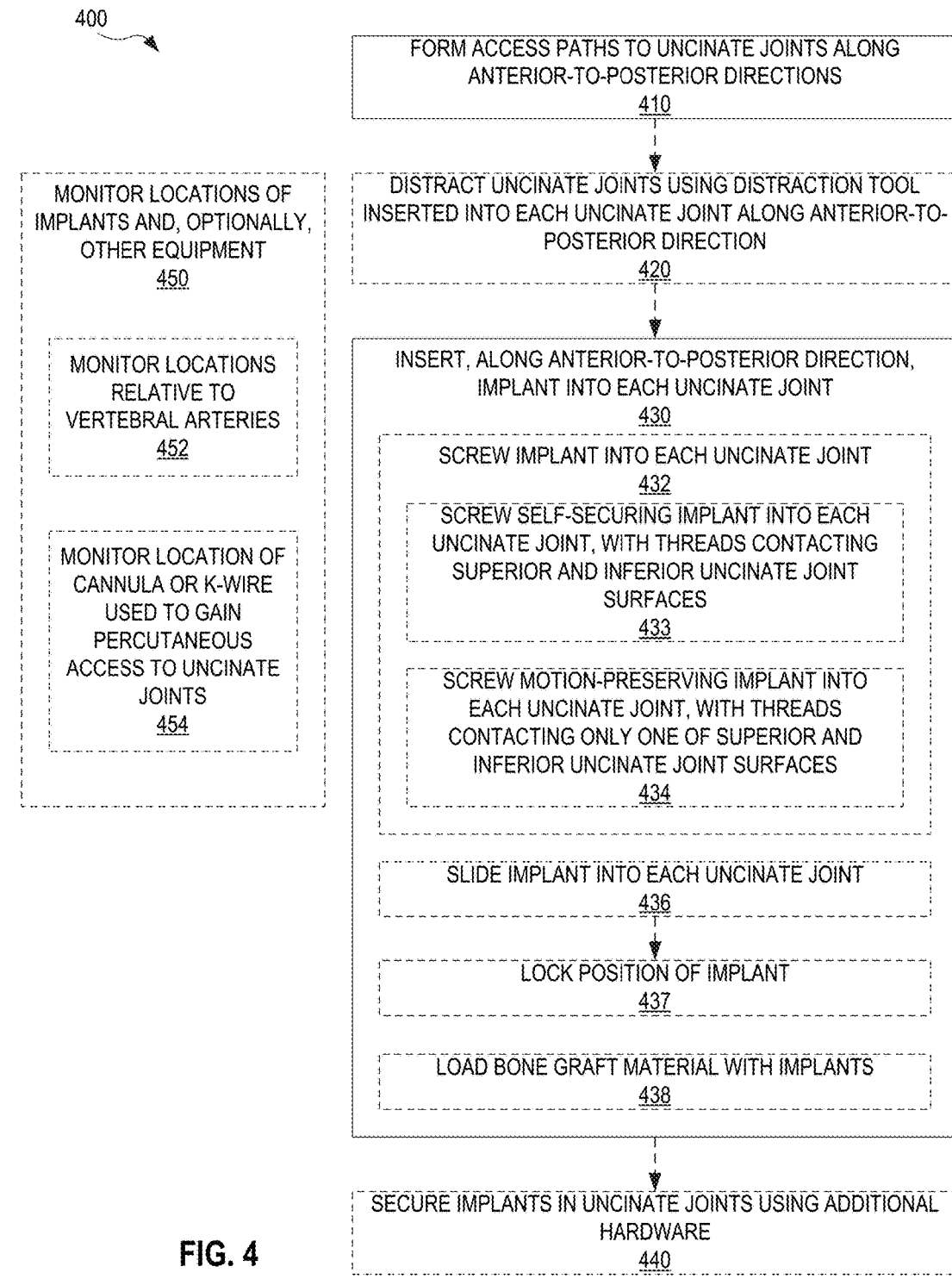
FIG. 4 illustrates a method for stabilizing the uncinate joints of a cervical spine segment, using access to the uncinate joints via anterior-to-posterior directions, according to an embodiment.

FIG. 4 illustrates one exemplary method 400 for stabilizing uncinate joints 120 (FIG. 1) of cervical spine segment 180, using access to uncinate joints 120 via anterior-to-posterior directions 210 (FIG. 2). Method 400 is an embodiment of step 310 of method 300 (FIG. 3) and may be performed percutaneously. Method 400 may be performed while leaving intervertebral disc 150 intact. In one implementation, method 400 facilitates fusion of uncinate joints 120. In another implementation, method 400 preserves motion of cervical spine segment 180. In yet another implementation, method 400 utilizes biodegradable implants that, after healing of an intervertebral disc injury, degrade and cease to play a role in the function of cervical spine segment 180.

In a step 410, an access path to each uncinate joint 120 is formed along a corresponding anterior-to-posterior direction 210, such that the access path is substantially in line with uncinate joint 120. In one example of step 410, for each uncinate joint 120, a guide wire is inserted into patient 170 along anterior-to-posterior direction 210. Herein, a "guide wire" refers to a wire that defines a direction and aids movement of tools and/or implants along this direction. A guide wire may refer to a Kirschner wire. The guide wire may be inserted to a depth of about 8-12 millimeters into uncinate joint 120. The guide wire may be threaded to cooperate with implants having a threaded cannulation. In another example of step 410, for each uncinate joint 120, a cannula is inserted into patient 170 along anterior-to-posterior direction 210. In yet another example, an access path is drilled along anterior-to-posterior direction 210, for example by implant 100 or a dedicated drill. Step 410 may utilize methods known in the art. For example, for each uncinate joint 120, a surgeon may use a robot or other device, mounted to patient 170 or mounted to a frame attached to patient 170, to align a guide wire with anterior-to-posterior direction 210, and then tapping the guide wire into patient 170 to reach uncinate joint 120. In one example, the access path goes through a longus colli muscle of patient 170.

In an optional step 420, each uncinate joint 120 is distracted using a distraction tool inserted into uncinate joint 120 along the corresponding access path formed in step 410. In one example of step 420, for each uncinate joint 120, a surgeon moves a cannulated distraction tool over a guide wire, placed in step 410, to reach uncinate joint 120, and then controls the distraction tool over the guide wire to distract uncinate joint 120. In another example of step 420, for each uncinate joint 120, a surgeon directs the distraction tool to uncinate joint 120 through a cannula, placed in step 410, to reach uncinate joint 120, and then controls the distraction tool through the cannula to distract uncinate joint 120.

In a step 430, for each uncinate joint 120, implant 100 is inserted into uncinate joint 120 using the access path formed in step 410. In one example of step 430, implants 100 are cannulated and, for each uncinate joint 120, a surgeon moves implant 100 over a guide wire to uncinate joint 120. In another example of step 430, for each uncinate joint 120, a surgeon moves implant 100 through a cannula to uncinate joint 120.

In certain implementations of method 400, compatible with both guide-wire insertion and through-cannula insertion of implants 100 into uncinate joints 120, each implant 100 includes threads and step 430 includes a step 432 of using the threads to screw implants 100 into place in uncinate joints 120. Such threaded embodiments of implants 100 are discussed below in reference to FIGS. 5A-8B, 13A-15, and 17A-18C. In one such implementation, step 432 includes a step 433 of screwing a self-securing and threaded embodiment of implant 100 into each uncinate joint 120, with the threads contacting both the superior surface and inferior surfaces of uncinate joint 120. The superior surface of uncinate joint 120 is that of superior cervical vertebra 184, and the inferior surface of uncinate joint 120 is that of inferior cervical vertebra 186. Exemplary implants compatible with step 433 are discussed below in reference to FIGS. 5A-8C. In another such implementation, step 432 includes a step 434 of screwing a motion-preserving embodiment of implant 100 into each uncinate joint 120, with the threads contacting only one of the superior surface and inferior surfaces of uncinate joint 120, while the other one of the superior surface and inferior surfaces of uncinate joint 120 is allowed to move relative to implant 100, at least during insertion of the implant into uncinate joint 120. Exemplary implants compatible with step 434 are discussed below in reference to FIGS. 13A-15 and 17A-D.

In another implementation of method 400, also compatible with both guide-wire insertion and through-cannula insertion of implants 100 into uncinate joints 120, step 430 includes a step 436 of sliding implants 100 into uncinate joints 120. Exemplary implants compatible with step 436 are discussed below in reference to FIGS. 9A-12B. Optionally, step 436 is followed by a step 437, wherein, for each uncinate joint 120, a lock mechanism of each implant 100 is engaged to lock the position of implant 100 within uncinate joint 120. The lock may be engaged by rotating a portion of implant 100 to grip the surfaces of uncinate joint 120. Exemplary implants with such a lock mechanism are discussed below in reference to FIGS. 11A-12B.

Optionally, step 430 includes a step 438 of loading bone graft material into each uncinate joint 120 together with, or into, the corresponding implant 100, to promote (a) fusion of uncinate joints 120 or (b) bony ingrowth in uncinate joints 120 at interfaces between implants 100 and one of cervical vertebrae 184 and 186. In one example of step 438, each implant 100 includes at least one void capable of accommodating bone graft material. Bone graft material may be loaded into the void(s) of each implant 100 before or after inserting implant 100 into uncinate joint 120. In another example of step 438, at least a portion of each implant 100 is a porous portion substantially composed of bone graft material. Since the surfaces of uncinate joints 120 are cortical bone, fusion promoted by step 438 may be stronger and/or faster than fusion within intervertebral disc space 140.

Without departing from the scope hereof, implant 100 and the distraction tool of step 420 may be integrated, or be the same. In this case, steps 420 and 430 may be performed concurrently. An example hereof is discussed below in reference to FIGS. 18A-19B.

In certain embodiments, method 400 includes a step 440 of securing each implant 100 to the corresponding uncinate joint 120 using additional hardware. In one example of step 440, a surgeon secures each implant 100 to both superior vertebra 184 and inferior vertebra 186 of cervical spine segment 180. In another example, a surgeon secures each implant 100 to only one of superior vertebra 184 and inferior vertebra 186 of cervical spine segment 180. Step 440 may be performed percutaneously. Exemplary implants compatible with step 440 are discussed in reference to FIGS. 9A-10B, 13A-15, and 17.

In certain embodiments, method 400 includes a step 450 of monitoring the locations, within patient 170, of implants 100 and, optionally, other equipment used to perform one or more of steps 410-440. Step 450 may be performed during the execution of some or all of steps 410-440. Step 450 is an embodiment of step 318. In one embodiment, step 450 includes a step 452 of monitoring locations of implants 100, and optionally other equipment, relative to vertebral arteries 230 (FIG. 2). In implementations of method 400 based upon percutaneous access to uncinate joints 120, step 450 may include a step 454 of monitoring the locations of cannulae, guide wires, or other devices providing percutaneous access to uncinate joints 120.

Without departing from the scope hereof, method 400 may be performed independently for each of the two uncinate joints 120 of cervical spine segment 180.

FIGS. 5A and 5B illustrate one exemplary threaded implant 500 for stabilizing uncinate joint 120 (FIG. 1). Threaded implant 500 is an embodiment of implant 100 and may be implemented in method 400 as the self-securing implant of step 433. FIG. 5A shows threaded implant 500 in side elevation. FIG. 5B shows a cross sectional view of threaded implant 500, wherein the cross section is taken along line 5B-5B in FIG. 5A. FIGS. 5A and 5B are best viewed together.

Threaded implant 500 has length 580 and diameter 582. Length 580 is at least six millimeters, for example, to provide sufficient contact area between threaded implant 500 and surfaces of uncinate joint 120 that threaded implant 500 is capable of supporting the load of uncinate joint 120. Length 580 is at most eighteen millimeters, for example, to ensure that threaded implant 500 does not encroach the neural foramen. Diameter 582 may be in the range between two and seven millimeters, to produce a spacing, between superior and inferior surfaces of uncinate joint 120 when threaded implant 500 is inserted therein, which is sufficient to relieve impingement issues or pressure on intervertebral disc 150 (FIG. 1) while minimizing damage to uncinate joint 120 and allowing for percutaneous insertion of threaded implant 500. In one example, diameter 582 is such that threaded implant 500 may be inserted into uncinate joint 120 through a cannula.

Threaded implant 500 includes threads 510 along at least a portion of length 580. Threads 510 have pitch 588 and depth 584. Depth 584 is, for example, in the range between 0.5 and 1.2 millimeters. Pitch 588 is, for example, in the range between 0.5 and 2.0 millimeters. Optionally, depth 584 and/or pitch 588 changes along the length of threaded implant 500. In one such example, pitch 588 is in the range between 3 and 4 millimeters for the full extent of threads 510, but closer to leading end 520 (the end that first enters uncinate joint 120 when inserting threaded implant 500 therein) threads 510 include only one set of threads while, further from leading end 520, threads 510 include two sets of interlaced threads. Although not shown in FIGS. 5A and 5B, threaded implant 500 may include a non-threaded portion at the trailing end of threaded implant 500 (opposite leading end 520), without departing from the scope hereof.

In one implementation, leading end 520 of threaded implant 500 is tapered to ease insertion of threaded implant into uncinate joint 120. In another implementation, at least a portion of threaded implant, extending to leading end 520, is tapered as indicated by dashed lines 560 to ease insertion of threaded implant into uncinate joint 120. In this implementation, the taper angle 562 may be less than 15°, for example between 4° and 8°. Taper angle 562 may be configured to match the deviation from parallelism between cervical vertebrae 184 and 186 at uncinate joint 120, which stems from the lordosis of the cervical spine. Although FIG. 5A shows optional tapering (as indicated by dashed lines 560) as extending along the full length of threaded implant 500, threaded implant 500 may be tapered only along a portion of the length of threaded implant 500, without departing from the scope hereof. In one such example, a leading end of threaded implant 500 is tapered (as indicated by dashed lines 560) while a trailing end of threaded implant 500, adjacent the leading end of threaded implant 500, is not tapered.

In one embodiment, threaded implant 500 is cannulated with a through-hole 530 extending for the full length 580. Through-hole 530 has diameter 586. Diameter 586 may be in the range from 0.5 to 4 millimeters. In an exemplary use scenario, threaded implant 500 is threaded into uncinate joint 120 over a guide wire, wherein the guide wire is passing through through-hole 530.

Although not shown in FIGS. 5A and 5B, threaded implant 500 may include an interface at its trailing end, without departing from the scope hereof. This interface is configured to interface with a driver or drill, such that this driver or drill threads threaded implant 500 into place in uncinate joint 120.

In one embodiment, threaded implant 500 is substantially composed of a metal such as titanium, titanium alloy, stainless steel, cobalt, chromium, or a combination thereof.

Without departing from the scope hereof, such metal embodiments of threaded implant 500 may include a coating, for example a hydroxyapatite coating, to achieve improved fixation of threaded implant 500 to uncinate joint 120. In another embodiment, threaded implant 500 includes a porous portion with pores capable of accommodating bone graft material, as discussed in reference to step 438 of method 400. In one example hereof, threaded implant 500 is substantially composed of, or includes, porous metal. In a related embodiment, at least a portion of threaded implant 500 is a porous portion substantially composed of bone graft material. In yet another embodiment, threaded implant 500 is substantially composed of allograft bone. In a further embodiment, threaded implant 500 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. In another embodiment, threaded implant 500 includes a polymer, such as polyetheretherketone (PEEK) or another polyaryletherketone (PAEK) polymer. Any of the above materials may be used in a 3-D printing process to make threaded implant 500.

FIG. 6A is a diagram 600 showing, in an anterior view, a pair of threaded implants 500 (FIGS. 5A and 5B) installed in uncinate joints 120 between cervical vertebrae 184 and 186 according to method 400. FIG. 6B is a close-up of diagram 600 showing one uncinate joint 120 with greater clarity. FIGS. 6A and 6B are best viewed together. When implemented in method 400, each threaded implant 500 is screwed into the corresponding uncinate joint 120 with threads 510 (not shown in FIGS. 6A and 6B) contacting both superior surface 684 and inferior surface 686 of uncinate joint 120. Threads 510 may grip superior surface 684 and inferior surface 686 and cooperate with a tension band to be self-securing in uncinate joint 120. Threaded implants 500 may be inserted into uncinate joints 120 while leaving intervertebral disc 150 intact. Method 400 may utilize optional through-hole 530 to insert threaded implant into uncinate joint 120 over a guide wire. Alternatively, or in combination therewith, method 400 may utilize optional through-hole 530 to carry or accept bone graft material used in step 438 of method 400.

FIGS. 7A and 7B illustrate one exemplary fenestrated, threaded implant 700 for stabilizing uncinate joint 120 (FIG. 1). Fenestrated, threaded implant 700 is an embodiment of threaded implant 500 (FIGS. 5A and 5B) and may be implemented in method 400 as the self-securing implant of step 432, as shown in FIGS. 6A and 6B. FIG. 7A shows fenestrated, threaded implant 700 in side elevation. FIG. 7B shows a cross section of fenestrated, threaded implant 700, wherein the cross section is taken along line 7B-7B in FIG. 7A. FIGS. 7A and 7B are best viewed together.

Fenestrated, threaded implant 700 is similar to threaded implant 500 as shown in FIGS. 5A and 5B, except for having fenestrations 720. Fenestrations 720 may serve to accommodate material displaced from uncinate joint 120 when fenestrated, threaded implant 700 is inserted therein. Fenestrations 720 may be particularly useful if using fenestrated, threaded implant 700 as the distraction tool in step 420 of method 400. Alternatively, or in combination therewith, fenestrations 720 may be cavities that carry bone graft material with the purpose of promoting fusion of uncinate joints 120. Furthermore, edges of fenestrations 720 may help secure fenestrated, threaded implant 700 in uncinate joint 120.

Although not shown in FIGS. 7A and 7B, fenestrations 720 may, at least in places, have depth sufficient to connect with through-hole 530 (if present), or fenestrations 720 may, at least in places, pass through fenestrated, threaded implant 700 from one side to another opposite side thereof, without departing from the scope hereof.

FIGS. 8A and 8B illustrate another exemplary fenestrated, threaded implant 800 for stabilizing uncinate joint 120 (FIG. 1). Fenestrated, threaded implant 800 is an embodiment of threaded implant 500 (FIGS. 5A and 5B) and may be implemented in method 400 (FIG. 4) as the self-securing implant of step 432, as shown in FIGS. 6A and 6B. FIG. 8A shows fenestrated, threaded implant 800 in side elevation. FIG. 8B shows a cross section of fenestrated, threaded implant 800, wherein the cross section is taken along line 8B-8B in FIG. 8A. FIGS. 8A and 8B are best viewed together.

Fenestrated, threaded implant 800 is similar to fenestrated, threaded implant 700 (FIGS. 7A and 7B), except for including cavities 830 in fenestrations 720. In one embodiment, at least some of cavities 830 are through-holes extending between fenestrations 720 located on opposite sides of fenestrated, threaded implant 800. In another embodiment, each cavity 830 is an separate pocket in fenestrated, threaded implant 800, which does not connect with other cavities 830 or with through-hole 530 (if present). In this embodiment, cavities 830 may serve to accommodate bone graft material loaded into cavities 830 prior to insertion of fenestrated, threaded implant 800 into uncinate joint 120. Thus, this embodiment of fenestrated, threaded implant 800 is compatible with embodiments of method 400 that include steps 432 and 438. In yet another embodiment, cavities 830 coexist with through-hole 530, and at least some of cavities 830 have depth sufficient to reach through-hole 530. In this embodiment, a surgeon may load bone graft material into through-hole 530, from anterior side 202, after placing fenestrated, threaded implant 800 in uncinate joint 120, whereafter the bone graft material is allowed to contact surfaces of uncinate joint 120 via cavities 830. Thus, this embodiment of fenestrated, threaded implant 800 is compatible with embodiments of method 400 that include steps 432 and 438.

FIG. 8C illustrates a cap 880 for sealing through-hole 530 of fenestrated, threaded implant 800 at the trailing end thereof. The trailing end of fenestrated, threaded implant 800 is the end opposite optionally tapered leading end 520. The trailing end is associated with a surface 802. Cap 880 may serve, for example in step 438, to seal the trailing-end portion of through-hole 530 after loading bone graft material into through-hole 530, to prevent bone graft material from leaking out of the trailing end of through-hole 530. In one implementation of method 400, sealing of through-hole 530 at leading end 520 is unnecessary since tissue of patient 170 provides resistance against bone graft material leaking out through through-hole 530 at leading end 520.

Cap 880 includes a cylindrical member 882 that fits in through-hole 530. Although not shown in FIGS. 8A-C, and without departing from the scope hereof, cylindrical member 882 and at least a portion of through-hole 530 may be threaded, such that a surgeon may screw cap 880 into through-hole 530. In one embodiment, cap 880 includes a larger-diameter element 884 with a surface 886 facing cylindrical member 882. In this embodiment, surface 886 of cap 880 faces surface 802 of fenestrated, threaded implant 800 when inserting cap 880 into through-hole 530. A surgeon may insert cap 880 into through-hole 530 to a depth determined by contact between surfaces 802 and 886.

In one implementation, cap 880 includes a recess 888 having shape matching that of a tool, for example a phillips-head screwdriver/drill or a star-head screwdriver/drill. A surgeon may insert such a tool into recess 888 to guide, and optionally screw, cylindrical member 882 into through-hole 530. In another embodiment, larger-diameter element 884 is shaped to at least partly fit within a tool, such as a hexagonal wrench, thus allowing a surgeon to use a tool to grab onto larger-diameter element 884 to guide, and optionally screw, cylindrical member 882 into through-hole 530.

FIG. 8D illustrates, in side elevation from direction opposite cylindrical member 882 and mounted in through-hole 530 of fenestrated, threaded implant 800, one exemplary cap 880' which is an implementation of cap 880 that further implements a locking lever. In cap 880', larger-diameter element 884 is implemented as an oblong element 884'. For example, oblong element 884' is oval, rectangular, or rectangular with rounded corners. The longer dimension of oblong element 884' extends beyond fenestrated, threaded implant 800 by a distance 850, while the shorter dimension of oblong element 884' has extent no greater than that of fenestrated, threaded implant 800. Optionally, at least a portion of oblong element 884' extending beyond fenestrated, threaded implant 800 includes a jagged surface 883. Jagged surface 883 is configured to grip a surface of uncinate joint 120 to at least participate in securing fenestrated, threaded implant 800 in uncinate joint 120. Without departing from the scope hereof, oblong element 884' may extend beyond fenestrated, threaded implant 800 in only one direction as opposed to the two directions shown in FIGS. 8D.

In one embodiment, cylindrical member 882 of cap 880' is sized for pressure fit into through-hole 530. Tissue of patient 170 prevents fenestrated, threaded implant 800 from migrating in any other direction than back out in the posterior-to-anterior direction. Cap 880', when secured to uncinate joint 120, prevents fenestrated, threaded implant 800 from migrating in the posterior-to-anterior direction, such that cap 880' locks fenestrated, threaded implant 800 in uncinate joint 120. In an exemplary use scenario, cap 880' is inserted into through-hole 530 (either prior to or after insertion of fenestrated, threaded implant 800 into uncinate joint 120) with cap 880' aligned such that the longer dimension of oblong element 884' does not interfere with surfaces of uncinate joint 120. After insertion of cap 880' into through-hole 530, cap 880' is rotated about the axis of through-hole 530, for example by about 45 to about 135 degrees, to secure cap 880' to one or two surfaces of uncinate joint 120. Optionally, each surface of uncinate joint 120 to which cap 880' is secured is prepared, for example by a high-speed drill, to form a recess for accommodating cap 880'.

Figure 8E:
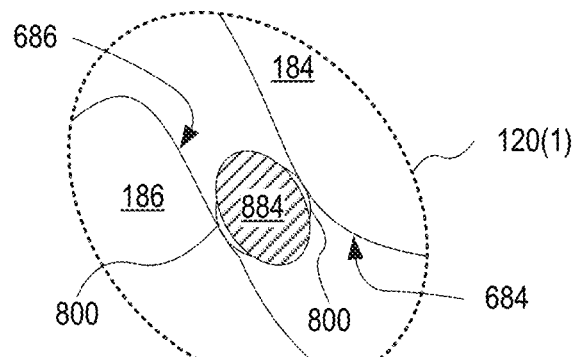
FIGS. 8E and 8F show, in an anterior view, the fenestrated, threaded implant of FIGS. 8A and 8B with the cap of FIG. 8D installed in uncinate joint 120, according to an embodiment.
Figure 8F:
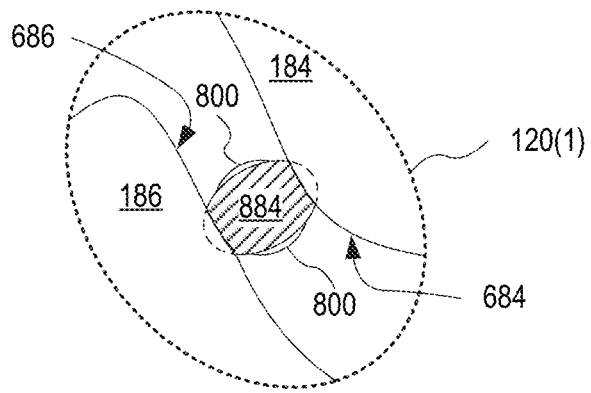

FIGS. 8E and 8F show, in an anterior view, fenestrated, threaded implant 800 (FIGS. 8A and 8B) with cap 880' (FIG. 8D) in uncinate joint 120, when installed in uncinate joint 120 according to method 400 (FIG. 4). FIGS. 8E and 8F are best viewed together. In FIG. 8E, cap 880' is in its unlocked configuration, after step 436 and before step 437 of method 400. In this configuration, fenestrated, threaded implant 800 contacts superior surface 684 (FIG. 6B) and inferior surface 686, respectively, but oblong member 884' does not grip either of superior surface 684 and inferior surface 686. In FIG. 8F, cap 880' is in its locked configuration, after step 437 of method 400. In this configuration, at least a portion of oblong member 884' is embedded into each of superior surface 684 and inferior surface 686, thus locking the position of fenestrated, threaded implant 800 in uncinate joint 120.

FIGS. 9A and 9B illustrate one exemplary shim implant 900 for stabilizing uncinate joint 120 (FIG. 1). Shim implant 900 is an embodiment of implant 100 and may be implemented in method 400 as the implant of step 436. FIG. 9A shows shim implant 900 in side elevation. FIG. 9B shows a cross section of shim implant 900, wherein the cross section is taken along line 9B-9B in FIG. 9A. FIGS. 9A and 9B are best viewed together.

Shim implant 900 has length 980, width 982, and height 984. Length 980 is at least six millimeters, for example, to provide sufficient contact area, between shim implant 900 and surfaces of uncinate joint 120, that shim implant 900 is capable of supporting the load of uncinate joint 120. Length 980 is at most eighteen millimeters, for example, to ensure that shim implant 900 does not encroach the neural foramen. Width 982 may be in the range between two and seven millimeters to provide sufficient contact area, between shim implant 900 and surfaces of uncinate joint 120, while minimizing lateral displacement of intervertebral disc 150 (FIG. 1). Height 984 may be in the range between two and seven millimeters, to produce a spacing, between superior and inferior surfaces of uncinate joint 120 when shim implant 900 is inserted therein, which is sufficient to relieve impingement issues or pressure on intervertebral disc 150 (FIG. 1), while minimizing damage to uncinate joint 120 and allowing for percutaneous insertion of shim implant 900.

Shim implant 900 has surfaces 924 and 926 configured to contact the superior surface and the inferior surface, respectively, of uncinate joint 120. Shim implant 900 also has a surface 922 configured to be the trailing surface of shim implant 900, when inserting shim implant 900 into uncinate joint 120 according to method 400. Without departing from the scope hereof, surfaces 924 and 926, as well as other surfaces of shim implant 900 may be non-planar. For example, shim implant 900 may be tapered, as indicated by dashed lines 960, with a taper angle 962. Taper angle 962 may be less than 15°, for example between 4° and 8°. Taper angle 962 may be configured to match the deviation from parallelism between cervical vertebrae 184 and 186 at uncinate joint 120, which stems from the lordosis of the cervical spine.

Optionally, shim implant 900 is cannulated with through-hole 530 extending for the full length 980, such that shim implant 900 may be inserted into uncinate joint 120 over a guide wire.

In one embodiment, shim implant 900 is substantially composed of a metal such as titanium, titanium alloy, stainless steel, cobalt, chromium, or a combination thereof. Without departing from the scope hereof, such metal embodiments of shim implant 900 may include a coating, for example a hydroxyapatite coating, on surfaces 924 and 926 to achieve improved fixation of shim implant 900 to uncinate joint 120. In another embodiment, shim implant 900 includes a porous portion with pores that may carry bone graft material to uncinate joint 120, as discussed in reference to step 438 of method 400. In one example, surfaces 924 and 926 are porous. In another example, shim implant 900 is substantially composed of, or includes, porous metal. In a similar embodiment, this porous portion is substantially composed of bone graft material that promotes bone growth in the pores thereof. In yet another embodiment, shim implant 900 is substantially composed of allograft bone. In a further embodiment, shim implant 900 includes a polymer. The polymer is, for example, polyetheretherketone (PEEK)

or another polyaryletherketone (PAEK) polymer. In a further embodiment, shim implant 900 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. Any of the above materials may be used in a 3-D printing process to make shim implant 900.

Although not shown in FIGS. 9A and 9B, shim implant 900 may include hollow portions and associated openings in the surfaces of shim implant 900, without departing from the scope hereof. Such hollow portions may accommodate bone graft material, as discussed in reference to step 438 of method 400.

FIGS. 10A and 10B illustrate, in an anterior view, shim implant 900 (FIGS. 9A and 9B) secured to uncinate joint 120 (FIG. 1) using exemplary additional hardware, as discussed in reference to step 440 of method 400 (FIG. 4). Shim implant 900 is placed in uncinate joint 120 with surfaces 924 and 926 contacting superior surface 684 (FIG. 6B) and inferior surface 686, respectively, of uncinate joint 120, and with surface 922 facing anterior side 202 (FIG. 2).

In FIG. 10A, shim implant 900 is secured to superior cervical vertebra 184 by affixing a bracket 1010 to shim implant 900 and superior cervical vertebra 184. Bracket 1010 may be affixed to shim implant 900 and superior cervical vertebra 184 by fasteners 1040 and 1030, respectively. Fastener 1030 is, for example, a screw or a pin. Fastener 1040 is, for example, a screw or a bolt. In one example, fastener 1040 is configured to attach to through-hole 530. Through-hole 530 may be threaded. In the implementation shown in FIG. 10A, surface 926 may be configured to allow relative movement between inferior surface 686 and surface 926, such that shim implant 900 is motion-preserving. Alternatively, surface 926 is textured to grip inferior surface 686, thus fixing inferior surface 686 with respect to superior surface 684.

In one example of the implementation shown in FIG. 10A, shim implant 900 includes voids at the interface with superior cervical vertebra 184. These voids are capable of accommodating bone graft material to promote bony ingrowth at this interface. The voids may be connected with through-hole 530, such that bone graft material may be loaded into the voids via through-hole 530 from anterior side 202 when shim implant 900 is located in uncinate joint 120. Fastener 1040, optionally in cooperation with bracket 1010, may function as a cap for sealing through-hole 530, to prevent leakage of bone graft material out of the trailing end of through-hole 530.

Without departing from the scope hereof, shim implant 900 may be mounted via bracket 1010 to inferior cervical vertebra 186 instead of superior cervical vertebra 184. Additionally, bracket 1010 may have shape different from that shown in FIG. 10A.

In FIG. 10B, shim implant 900 is secured to both superior cervical vertebra 184 and inferior cervical vertebra 186 by affixing a bracket 1050 to shim implant 900, superior cervical vertebra 184, and inferior cervical vertebra 186. Bracket 1050 may be affixed to shim implant 900, superior cervical vertebra 184, and inferior cervical vertebra 186 by fasteners 1040, 1030, and 1030, respectively, as discussed above in reference to FIG. 10A.

In one example of the implementation shown in FIG. 10B, shim implant 900 includes voids, at least at the interfaces with cervical vertebrae 184 and 186. These voids are capable of accommodating bone graft material to promote fusion of uncinate joint 120. The voids may be connected with through-hole, such that bone graft material may be loaded into the voids via through-hole 530 from anterior side 202 when shim implant 900 is located in uncinate joint 120. Fastener 1040, optionally in cooperation with bracket 1050, may function as a cap for sealing through-hole 530, to prevent leakage of bone graft material out of through-hole 530, as discussed in reference to FIG. 8C.

Figure 11A:
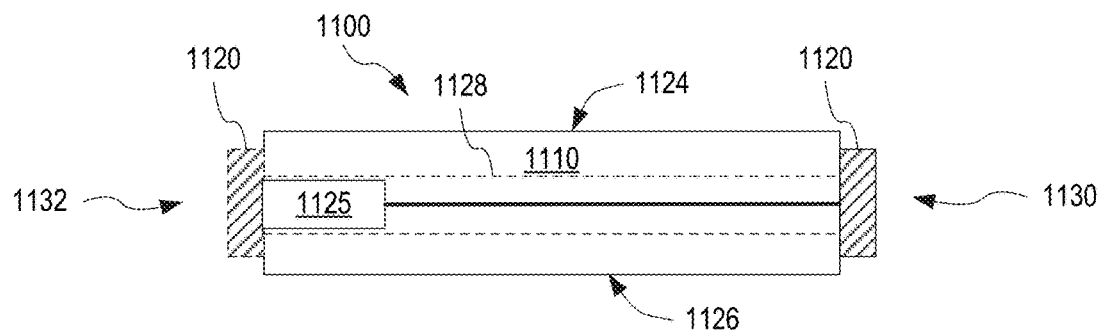
FIGS. 11A, 11B, 11C, 11D and 11E illustrate a locking implant for stabilizing uncinate joint 120, according to an embodiment.
Figure 11B:
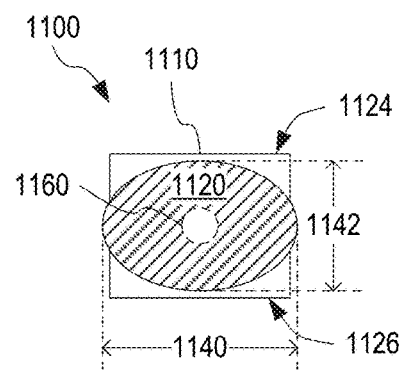
Figure 11C:
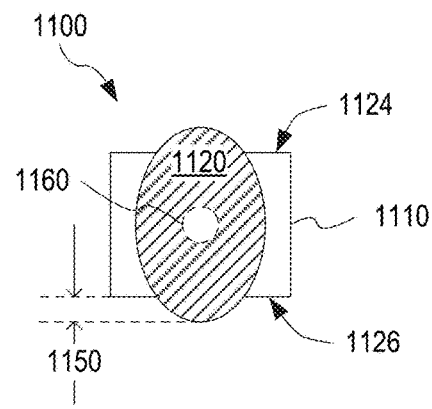

FIGS. 11A, 11B, and 11C illustrate one exemplary locking implant 1100 for stabilizing uncinate joint 120 (FIG. 1). Locking implant 1100 is an embodiment of implant 100 and may be implemented in method 400 (FIG. 4) as the implant of steps 436 and 437. FIG. 11A shows locking implant 1100 in side elevation. FIGS. 11B and 11C show a front elevation view of leading end 1130 of locking implant 1100, wherein leading end 1130 is the end of locking implant 1100 that first enters uncinate joint 120 when inserting locking implant 1100 into uncinate joint 120 according to method 400. In FIGS. 11A and 11B, locking implant 1100 is in its unlocked configuration. In FIG. 11C, locking implant 1100 is in its locked configuration. FIGS. 11A, 11B, and 11C are best viewed together.

Locking implant 1100 includes a body 1110 that is similar to shim implant 900 (FIG. 9). Body 1110 may be tapered as discussed in reference to shim implant 900. Body 1110 has surfaces 1124 and 1126 configured to face superior surface 684 (FIG. 6B) and inferior surface 686, respectively, of uncinate joint 120, when locking implant 1100 is placed in uncinate joint 120. At leading end 1130, locking implant 1100 further includes a locking lever 1120 attached to body 1110.

Locking implant 1100 has a longer dimension 1140 and a shorter dimension 1142. Shorter dimension 1142 is such that, when locking implant 1100 is in its unlocked configuration (see FIG. 11B), locking lever 1120 does not extend beyond surfaces 1124 and 1126. Longer dimension 1140 is such that, when locking implant 1100 is in its locked configuration (see FIG. 11C), locking lever 1120 extends beyond each of surfaces 1124 and 1126 by a distance 1150. Distance 1150 is, for example, in the range between 0.2 and 1.0 millimeters. The cross section of locking lever 1120 may be oval (as shown in FIGS. 11B and 11C), rectangular, or otherwise elongated to meet these requirements to longer dimension 1140 and shorter dimension 1142. Locking implant 1100 includes a rotation mechanism 1125 coupled with locking lever 1120. Rotation mechanism 1125 is accessible from trailing end 1132 of locking implant 1100. When actuated, rotation mechanism 1125 rotates locking lever 1120, for example from its unlocked position (FIG. 11B) to its locked position (FIG. 11C).

In one embodiment, locking implant 1100 is cannulated with a through-hole 1160 extending from leading end 1130 to trailing end 1132. Method 400 may utilize through-hole 1160 to insert locking implant 1100 into uncinate joint 120 over a guide wire, as discussed in reference to FIG. 4.

Rotation mechanism 1125 may be implemented in a shaft 1128 rigidly coupled to locking lever 1120. Shaft 1128 may implement rotation mechanism 1125 as a receptacle for a driver, such that rotation of the driver, when engaged with the receptable, results in rotation of locking lever 1120. The receptacle may be male or female or a combination thereof. Shaft 1128 may implement a portion of through-hole 1160.

Optionally, locking implant 1100 includes two or more locking levers 1120. In one example, a second locking lever 1120 is located at trailing end 1132. Rotation mechanism 1125 may be coupled with all locking levers 1120 of locking implant 1100 to simultaneously rotate all locking levers 1120. In embodiments including two or more locking levers 1120, all locking levers 1120 may be rigidly interconnected (for example via shaft 1128) and rotation mechanism 1125 may be integrated in one of locking levers 1120 as a receptacle for a driver, such that the driver, when acting on rotation mechanism 1125, rotates all locking levers 1120 in the same manner. The receptacle may be male or female or a combination thereof.

Without departing from the scope hereof, locking implant 1100 may include a locking lever 1120 only at trailing end 1132. In such an embodiment, rotation mechanism 1125 may be integrated in locking lever 1120 as a receptacle for a driver. The receptacle may be male or female or a combination thereof.

In one embodiment, locking implant 1100 is substantially composed of a metal such as titanium, titanium alloy, stainless steel, cobalt, chromium, or a combination thereof. Without departing from the scope hereof, such metal embodiments of locking implant 1100 may include a coating, for example a hydroxyapatite coating, on surfaces 1124 and 1126 and/or on locking lever(s) 1120 to achieve improved fixation of locking implant 1100 to uncinate joint 120. In another embodiment, locking implant 1100 includes a porous portion with pores that may carry bone graft material to uncinate joint 120, as discussed in reference to step 438 of method 400. For example, surfaces 1124 and 1126, or all of body 1110, may be porous. Surfaces 1124 and 1126, or all of body 1110, may be porous metal. In a similar embodiment, the porous portion is substantially composed of bone graft material that promotes bone growth in the pores thereof. In yet another embodiment, body 1110 is substantially composed of allograft bone. Although not shown in FIGS. 11A, 11B, and 11C, body 1110 may include hollow portions and associated openings in the surfaces of body 1110, without departing from the scope hereof. Such hollow portions may carry bone graft material, as discussed in reference to step 438 of method 400. In a further embodiment, locking implant 1100 is biodegradable or bioabsorbable and is composed, for example, of lactulose, proline, polyglycolic acid or a derivative thereof, poly-L-lactic acid or a derivative thereof, other biodegradable/bioabsorbable materials known in the art, or a combination thereof. Any of the above materials may be be used in a 3-D printing process to make body 1110.

Figure 11D:
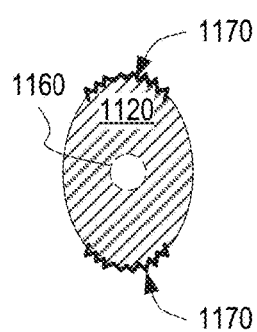

FIG. 11D illustrates one exemplary implementation of locking lever 1120 that includes a jagged surface 1170 on at least on a portion of locking lever 1120 configured to contact superior surface 684 and inferior surface 686.

Figure 11E:
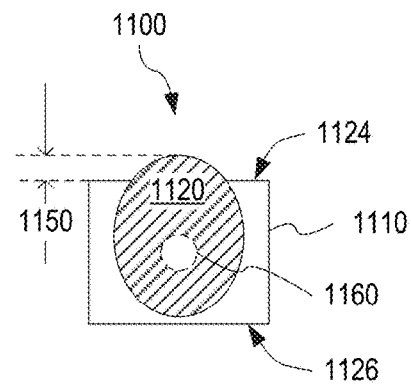

FIG. 11E illustrates another exemplary implementation of locking lever 1120, wherein locking lever extends beyond only one of surfaces 1124 and 1126 when in locked position. In this implementation, locking implant 1100 is configured such that locking lever 1120 contacts only one of superior surface 684 and inferior surface 686. Although not shown in FIG. 11E, the portion of locking lever 1120, which is configured to contact one of superior surface 684 and inferior surface 686, may be jagged as shown in FIG. 11D.

Figure 12A:
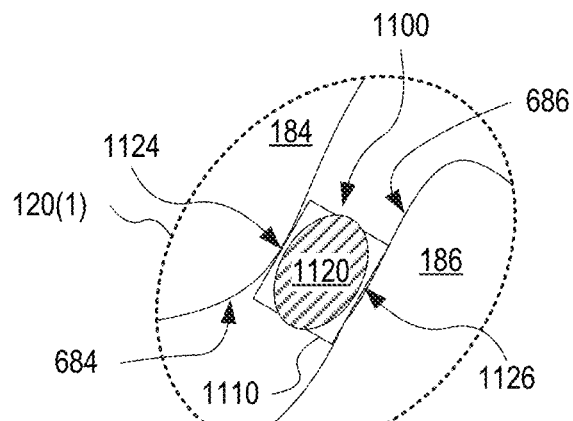
FIGS. 12A and 12B show, in a posterior view, the locking implant of FIGS. 11A-E) installed in an uncinate joint, according to an embodiment.
Figure 12B:
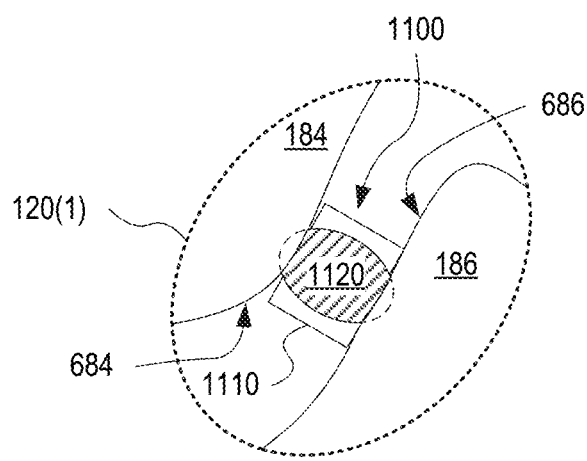

FIGS. 12A and 12B show, in a posterior view, locking implant 1100 (FIGS. 11A-E) in uncinate joint 120, when installed in uncinate joint 120 according to method 400 (FIG. 4). FIGS. 12A and 12B are best viewed together. In FIG. 12A, locking implant 1100 is in its unlocked configuration, after step 436 and before step 437 of method 400. In this configuration, surfaces 1124 and 1126 contact superior surface 684 (FIG. 6B) and inferior surface 686, respectively, but locking lever 1120 does not contact either of superior surface 684 and inferior surface 686. In FIG. 12B, locking implant 1100 is in its locked configuration, after step 437 of method 400. In this configuration, at least a portion of locking lever 1120 is embedded into each of superior surface 684 and inferior surface 686, thus locking the position of locking implant 1100 in uncinate joint 120.

FIGS. 13A, 13B, 13C, and 13D illustrate one exemplary motion-preserving implant 1300 for stabilizing uncinate joint 120 (FIG. 1). Motion-preserving implant 1300 is an embodiment of implant 100 and may be implemented in method 400 as the implant of step 434. FIG. 13A shows motion-preserving implant 1300 in side elevation. FIG. 13B shows motion-preserving implant 1300 in cross-sectional view, wherein the cross section is taken along line 13B-13B in FIG. 13A. FIG. 13C shows leading end 1330 of motion-preserving implant 1300 in elevation view, while FIG. 13D shows trailing end 1332 of motion-preserving implant 1300 in elevation view. Leading end 1330 is the end that first enters uncinate joint 120 when inserting motion-preserving implant 1300 into uncinate joint 120 according to method 400. FIGS. 13A-D are best viewed together.

Motion-preserving implant 1300 includes a screw 1310 with threads 1312. Threads 1312 may be similar to threads 510 (FIG. 5). Motion-preserving implant 1300 further includes a housing 1320 that partly contains screw 1310. Screw 1310 protrudes, by a distance 1386, through an opening 1324 of housing 1320, such that threads 1312 may contact a surface of uncinate joint 120. Distance 1386 is, for example, around one millimeter or a fraction of a millimeter. Distance 1386 may be such that housing 1320 contacts the surface of uncinate joint 120. Housing 1320 includes a surface 1322 that is able to slide on a surface of uncinate joint 120. In one example, surface 1322 is smooth. Surface 1322 may be curved to accommodate a variety of angles between surface 1322 and a surface of uncinate joint 120 in contact with surface 1322. Surface 1322 generally faces away from opening 1324. Motion-preserving implant 1300 further includes a rotation mechanism 1315 that, when actuated, rotates screw 1310. Rotation mechanism 1315 may be accessible from trailing end 1332. In one embodiment, rotation mechanism 1315 is a recess configured to accept a driver or drill, for example a hex driver or drill, such that this driver or drill may rotate screw 1310.

Motion-preserving implant 1300 has length 1380, width 1382, and height 1384, which may be similar to length 980, width 982, and height 984 of shim implant 900 (FIGS. 9A and 9B).

Optionally, motion-preserving implant 1300 is cannulated with a through-hole 1360 extending from leading end 1330 to trailing end 1332. Method 400 may utilize through-hole 1360 to insert motion-preserving implant 1300 into uncinate joint 120 over a guide wire, as discussed in reference to FIG. 4. Through-hole 1360 is centered relative to the cross section of screw 1310, such that screw 1310 may rotate while motion-preserving implant 1300 is placed over a guide wire.

Screw 1310 may be of similar material and/or structural composition as threaded implant 500 (FIGS. 5A and 5B). Housing 1320 may be of similar material and/or structural composition as shim implant 900.

Without departing from the scope hereof, housing 1320 may be tapered. In one example, housing 1320 is tapered, as indicated by dashed line 1370, with a taper angle 1372. Taper angle 1372 may be less than 15°, for example between 4° and 8°. Taper angle 1372 may be configured to match the deviation from parallelism between cervical vertebrae 184 and 186 at uncinate joint 120, which stems from the lordosis of the cervical spine. In another example, housing 1320 is curved and tapered, such that curved surface 1322 has orientation generally along dashed line 1370.

FIG. 14A shows, in an anterior view, a pair of motion-preserving implants 1300 (FIGS. 13A-D) installed in uncinate joints 120 according to method 400 (FIG. 4). FIG. 14B is a close-up of FIG. 14A showing one uncinate joint 120 in further detail. FIGS. 14A and 14B are best viewed together.

When inserting motion-preserving implant 1300 into corresponding uncinate joint 120, in step 434 of method 400, motion-preserving implant 1300 is oriented such that screw 1310 contacts superior surface 684 (FIG. 6B), while surface 1322 contacts inferior surface 686. A surgeon rotates screw 1310 using rotation mechanism 1315 (for clarity not shown in FIGS. 14A and 14B). Since screw 1310 contacts superior surface 684, this rotation screws motion-preserving implant 1300 into uncinate joint 120. Surface 1322 contacts inferior surface 686 while allowing relative movement between motion-preserving implant 1300 and inferior surface 686.

FIG. 15 shows, in an anterior view, motion-preserving implant 1300 (FIGS. 13A-D) secured to uncinate joint 120 (FIG. 1) using exemplary additional hardware, as discussed in reference to step 440 of method 400 (FIG. 4). Motion-preserving implant 1300 is located in uncinate joint 120 with screw 1310 contacting and gripping superior surface 684 (FIG. 6B). Motion-preserving implant 1300 is secured to superior cervical vertebra 184 by affixing a bracket 1510 to motion-preserving implant 1300 and superior cervical vertebra 184. Bracket 1510 may be affixed to motion-preserving implant 1300 and superior cervical vertebra 184 by fasteners 1540 and 1530, respectively. Fastener 1530 is, for example, a screw or a pin. Fastener 1540 is, for example, a screw or a bolt. In one example, fastener 1540 is configured to attach to through-hole 1360. Without departing from the scope hereof, bracket 1510 may have shape different from that shown in FIG. 15.

FIGS. 16A, 16B, 16C, and 16D illustrate one exemplary bracket 1600 for securing two implants 100, located in uncinate joints 120 of cervical spine segment 180 (FIG. 1), to one vertebra of cervical spine segment 180. Bracket 1600 is common to both implants 100. FIGS. 16A-D show a scenario, wherein bracket 1600 secures a pair of motion-preserving implants 1300 (FIGS. 13A-D) to cervical spine segment 180. However, bracket 1600 may be applied to other embodiments of implant 100, such as shim implant 900 (FIGS. 9A and 9B) and screw-in implant 1700 discussed below in reference to FIGS. 17A-D. Method 400 (FIG. 4) may implement bracket 1600 in step 440.

Figure 16A:
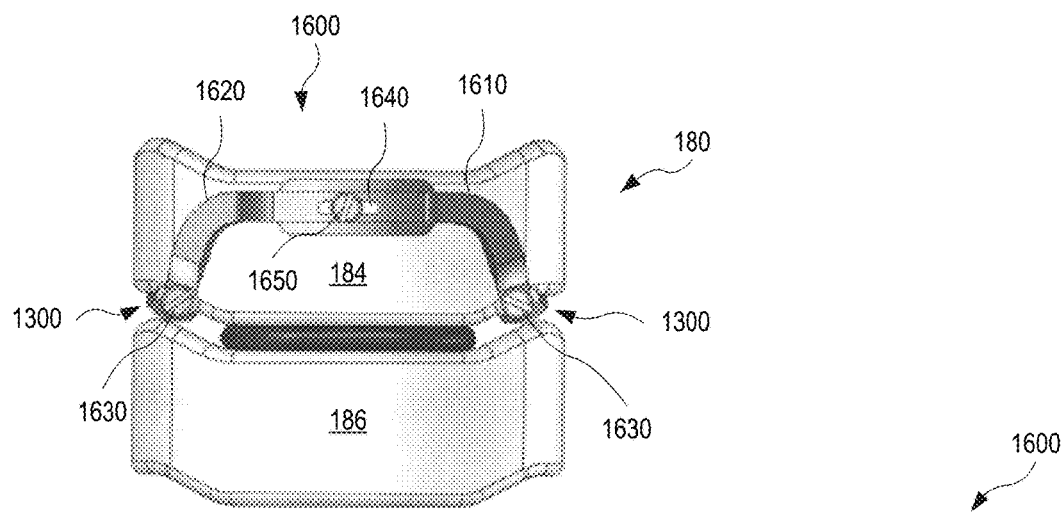
FIGS. 16A, 16B, 16C, and 16D illustrate a bracket for securing two implants, located in the uncinate joints of a cervical spine segment, to one vertebra of the cervical spine segment, according to an embodiment.
Figure 16B:
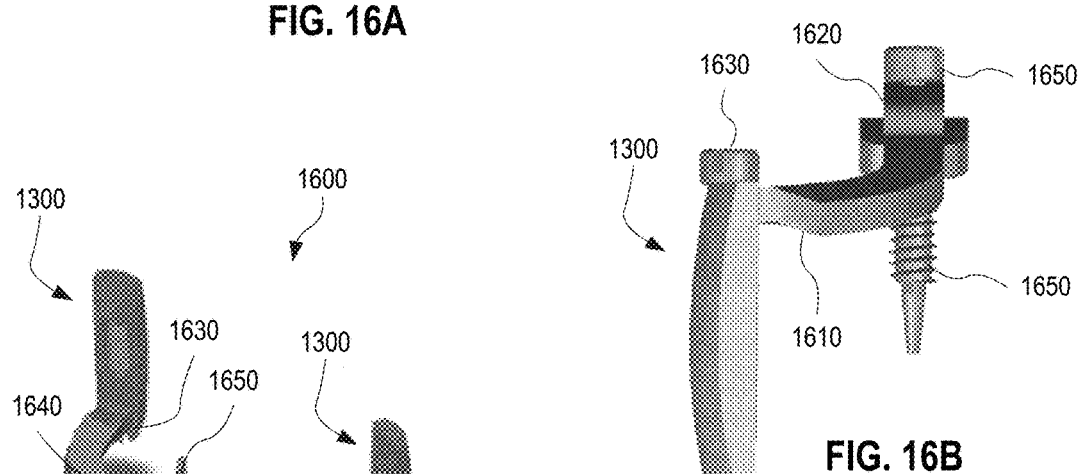
Figure 16C:
Figure 16D:
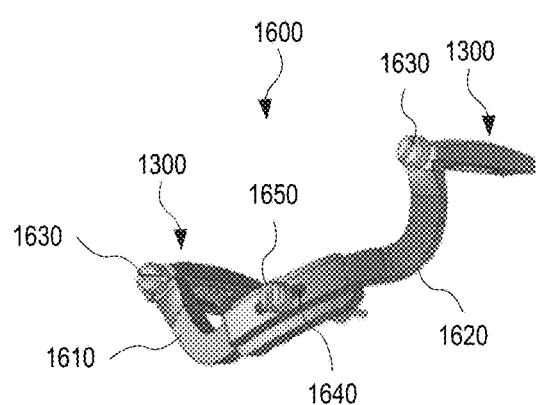

FIG. 16A shows, in an anterior view, a pair of motion-preserving implants 1300 (FIGS. 13A-D) secured to uncinate joints 120 (FIG. 1) using bracket 1600. FIG. 16B shows bracket 1600 in side elevation view, separate from cervical spine segment 180. Each of FIGS. 16C and 16D shows bracket 1600 in perspective view, separate from cervical spine segment 180. FIGS. 16A-D are best viewed together.

Bracket 1600 includes a half-bracket 1610 and a half-bracket 1620. Each of half-brackets 1610 and 1620 is attached to one motion-preserving implant 1300 by a fastener 1630. Fastener 1630 is, for example, a bolt or a screw. Each of half-brackets 1610 and 1620 has a slot 1640 configured to accept a screw 1650. Screw 1650 secures half-brackets 1610 and 1620 to an anterior surface of the vertebral body of superior cervical vertebra 184. The shape of half-brackets 1610 and 1620 may be different from those shown in FIGS. 16A-D, without departing from the scope hereof.

Although FIGS. 14-16D illustrate a configuration wherein motion-preserving implant 1300 is secured to superior cervical vertebra 184, motion-preserving implant 1300 may be inserted into uncinate joint 120 with screw 1310 contacting inferior surface 686 and with surface 1322 facing superior surface 684, such that motion-preserving implant 1300 may be secured to inferior cervical vertebra 186, without departing from the scope hereof.

Figure 17A:
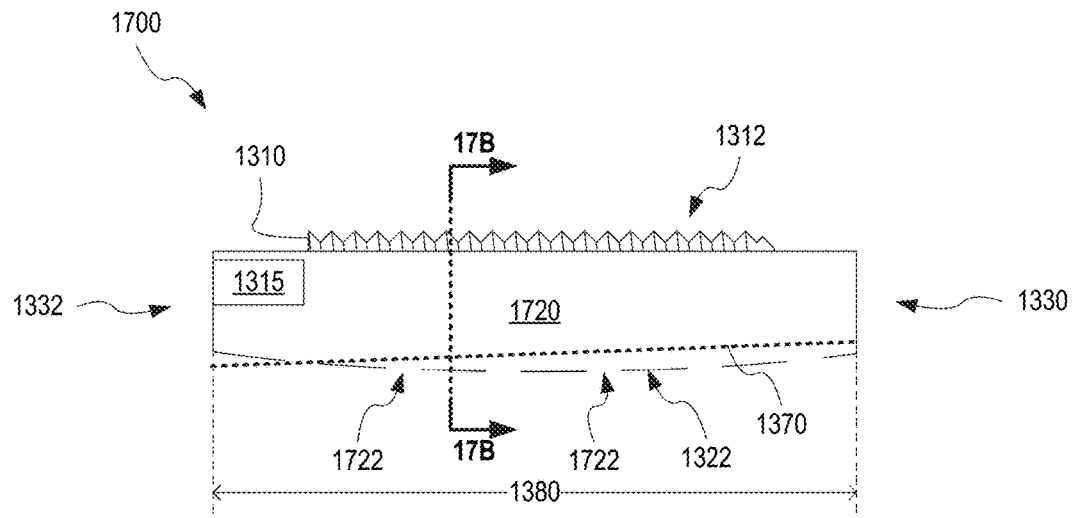
FIGS. 17A, 17B, 17C, and 17D illustrate a screw-in implant for stabilizing an uncinate joint, according to an embodiment.
Figure 17B:
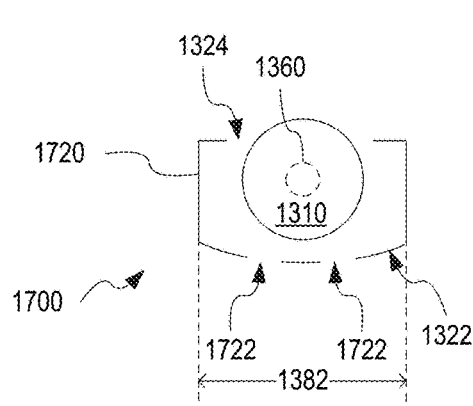
Figure 17C:
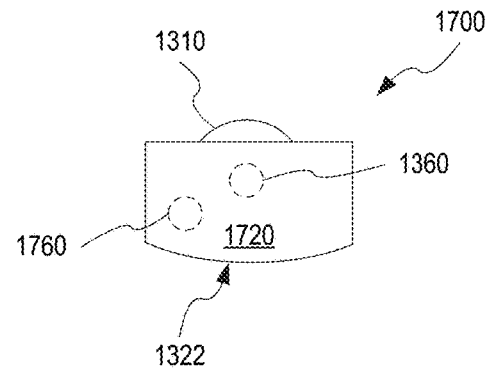
Figure 17D:
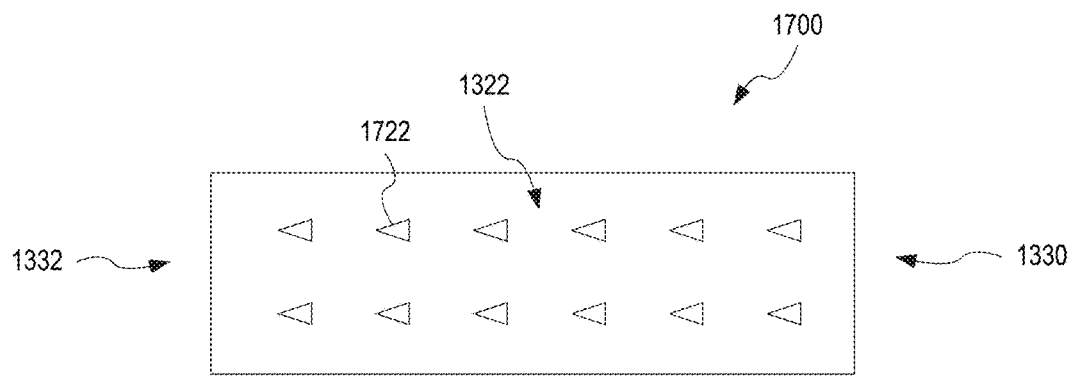

FIGS. 17A, 17B, 17C, and 17D illustrate one exemplary screw-in implant 1700 for stabilizing uncinate joint 120 (FIG. 1). Screw-in implant 1700 is similar to motion-preserving implant 1300 (FIGS. 13A-D) except that screw-in implant 1700 includes fenestrations 1722 that at least help secure screw-in implant 1700 to the surface of uncinate joint 120 opposite the surface of uncinate joint interfacing with screw 1310. Thus, screw-in implant 1700 is configured to fix motion of uncinate joint 120. Additionally, screw-in implant 1700 may include an access port 1760 that accepts bone graft material into screw-in implant 1700 from its trailing end 1332. FIG. 17A shows screw-in implant 1700 in side elevation. FIG. 17B shows screw-in implant 1700 in cross-sectional view, wherein the cross section is taken along line 17B-17B in FIG. 17A. FIG. 17C shows trailing end 1332 of screw-in implant 1700 in elevation view. FIG. 17D shows a fenestrated surface of screw-in implant 1700. FIGS. 17A-D are best viewed together.

As compared to motion-preserving implant 1300, screw-in implant 1700 includes a housing 1720 instead of housing 1320. Housing 1720 is similar to housing 1320, except that surface 1322 in housing 1720 includes fenestrations 1722. For clarity of illustration, not all fenestrations 1722 are labeled in FIGS. 17A-D. FIG. 17C shows surface 1322. Fenestrations 1722 may aid in securing screw-in implant 1700 to uncinate joint 120 through friction between fenestrations 1722 and an associated one of superior surface 684 and inferior surface 686.

In one embodiment, each fenestration 1722 is wider (in dimension associated with width 1382) closer to leading end 1330 and narrower closer to trailing end 1332. This shape may result in greater friction against lateral movement and posterior-to-anterior movement of surface 1322 in uncinate joint 120 than the friction between surface 1322 and uncinate joint 120 associated with insertion of screw-in implant 1700 along anterior-to-posterior direction 210 (FIG. 2). However, the shape of fenestration 1722 may differ from that shown in FIG. 17C, without departing from the scope hereof. Likewise, the number of fenestrations 1722, and/or the pattern in which fenestrations 1722 are arranged, may be different from what is shown in FIGS. 17A-C.

In one implementation, screw-in implant 1700 is self-securing by virtue of threads 1312. In another implementation, screw-in implant 1700 is secured to cervical spine segment 180 using a mounting bracket, and associated fasteners. In one example, screw-in implant 1700 is secured to cervical spine segment 180 using bracket 1510 (FIG. 15), bracket 1050 (FIG. 10B), or bracket 1600 (FIGS. 16A-D). In another example, screw-in implant 1700 is secured to cervical spine segment 180 using two brackets 1600 with one bracket secured to superior vertebra 184 and the other bracket secured to inferior vertebra 186.

In one exemplary scenario, screw-in implant 1700 is implemented in method 400 according to an embodiment of method 400, which includes step 434 and 438. In this scenario, bone graft material is loaded into housing 1720 and allowed to contact both superior surface 684 and inferior surface 686 (FIG. 6B) of uncinate joint 120 through fenestrations 1722 and opening 1324. In one implementation of step 438, bone graft material is loaded into housing 1720 prior to insertion of screw-in implant 1700 into uncinate joint 120. In another implementation of step 438, bone graft material is loaded into housing 1720 after insertion of screw-in implant 1700 into uncinate joint 120. In this implementation, bone graft material may be loaded into housing 1720 at trailing end 1332 via through-hole 1360, and with screw 1310 implemented with fenestrations that connect through-hole 1360 to an external surface of screw 1310 (as discussed in reference to fenestrated, threaded implant 800 (FIGS. 8A-D). Optionally, through-hole 1360 is subsequently sealed with a cap. In one example, sealing is accomplished by a mounting bracket, and/or associated fastener, used to secure screw-in implant 1700 to cervical spine segment 180. Such sealing may be accomplished using (a) fastener 1540 (FIG. 15) optionally with bracket 1510, (b) fastener 1040 optionally with bracket 1050 (FIG. 10B), or (c) fastener 1630 (FIGS. 16A-D) optionally with bracket 1600. In yet another implementation of step 438, bone graft material is loaded into housing 1720, via an access port 1760, after insertion of screw-in implant 1700 into uncinate joint 120. Access port 1760 may be subsequently sealed using a cap.

Without departing from the scope hereof, screw-in implant 1700 may be configured to allow for removal of screw 1310, along a posterior-to-anterior direction, when screw-implant 1700 is in place in uncinate joint 120. In this case, bone graft material may be loaded into housing 1720 after removal of screw 1310.

Figure 18A:
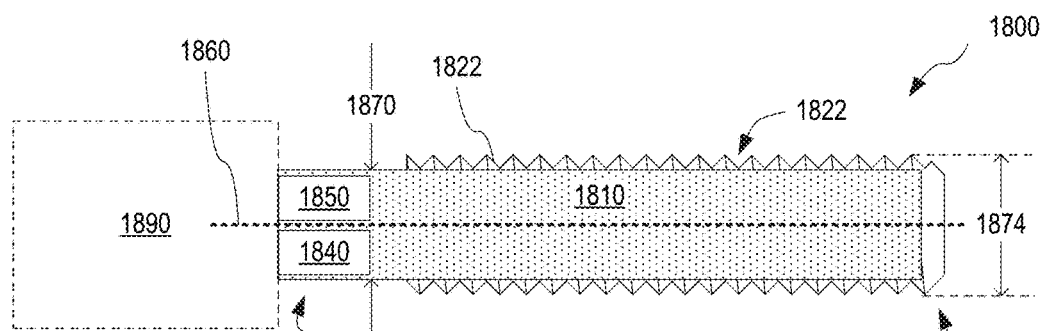
FIGS. 18A, 18B, 18C, and 18D illustrate an implant system including an implant, for stabilizing an uncinate joint, and a screw for inserting the implant into the uncinate joint, according to an embodiment.
Figure 18B:
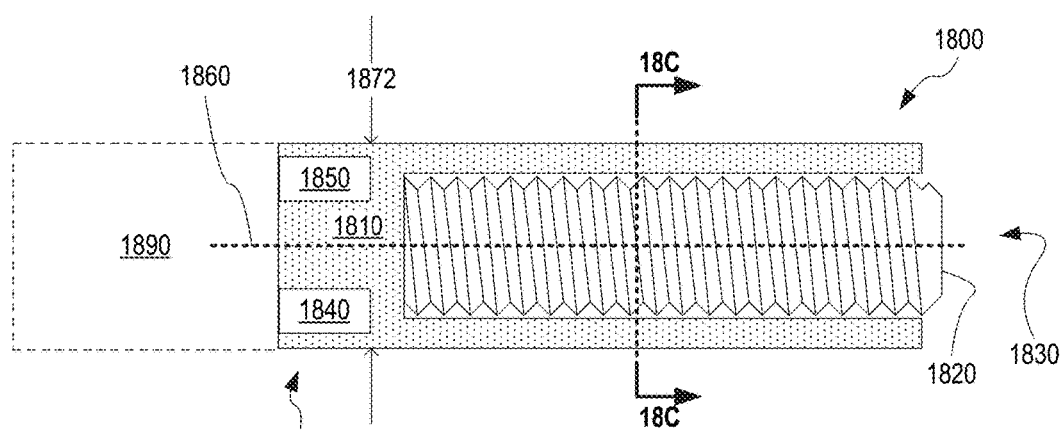
Figure 18C:
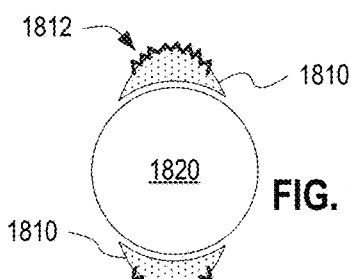
Figure 18D:
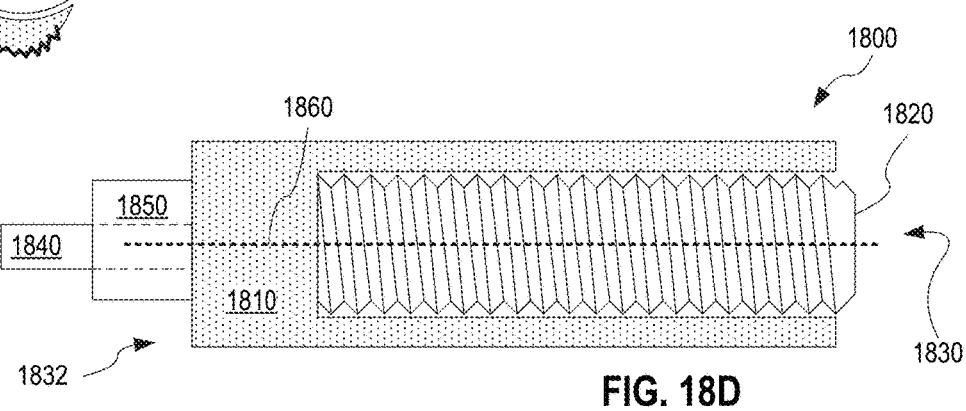

FIGS. 18A-D illustrate one exemplary implant system 1800 including (a) one exemplary implant 1810 for stabilizing uncinate joint 120 (FIG. 1) and (b) one exemplary screw 1820 for inserting implant 1810 into uncinate joint 120. Implant system 1800 is associated with a longitudinal axis 1860. Longitudinal axis 1860 is generally oriented along anterior-to-posterior direction 210 (FIG. 2) when implant system 1800 is located in uncinate joint 120. FIGS. 18A and 18B show implant system 1800 in mutually orthogonal side elevation views, both orthogonal to longitudinal axis 1860. FIG. 18C shows implant system 1800 in cross-sectional view, wherein the cross section is taken along line 18C-18C in FIG. 18B. FIG. 18D shows one example of implant system 1800 in the same view as used for FIG. 18B. FIGS. 18A-D are best view together. Implant system 1800 is configured to insert implant 1810 into uncinate joint 120 along anterior-to-posterior direction 210. Implant system 1800 and implant 1810 may be implemented in method 400 (FIG. 4).

Implant system 1800 has a leading end 1830 that enters uncinate joint 120 first, when inserting implant system 1800 into uncinate joint 120. Opposite leading end 1830, implant system has a trailing end 1832. Implant 1810 has an elongated cross section in the plane orthogonal to longitudinal axis 1860 (see FIG. 18C). For example, implant 1810 is oval, rectangular, or rectangular with rounded corners. The cross section of screw 1820 is circular in the plane orthogonal to longitudinal axis 1860. Screw 1820 includes threads 1822. Threads 1822 may have properties similar to threads 510 of threaded implant 500 (FIGS. 5A and 5B).

FIG. 18A shows implant system 1800 in an orientation associated with a minimum extent 1870 of implant 1810 in the plane orthogonal to longitudinal axis 1860. FIG. 18B shows implant system 1800 in an orientation associated with a maximum extent 1872 of implant 1810 in the plane orthogonal to longitudinal axis 1860. Screw 1820 has diameter 1874 that is greater than minimum extent 1870 and less than maximum extent 1872. Thus, in the dimension associated with minimum extent 1870, threads 1822 protrude from implant 1810, while in the dimension associated with maximum extent 1872, screw 1820 is enclosed by implant 1810.

Implant 1810 includes a rough surface 1812 on at least on a portion of implant 1810 configured to contact superior surface 684 and inferior surface 686 when implant 1810 is placed in uncinate joint 120. For clarity of illustration, rough surface 1812 is not indicated in FIGS. 18A and 18B. Rough surface 1812 may include fenestrations, protruding features, surface texture, or other elements to form rough surface 1812.

Implant system 1800 further includes interfaces 1840 and 1850, located at trailing end 1832. A surgeon may couple a tool 1890 to interfaces 1840 and 1850 to rotate implant 1810 and screw 1820, respectively, about longitudinal axis 1860. Tool 1890 and interfaces 1840 and 1850 are configured such that the surgeon may rotate screw 1820 independently of implant 1810. Without departing from the scope hereof, one or both of interfaces 1840 and 1850 may include functionality to rotate implant 1810 and screw 1820 in response to actuation by tool 1890. Tool 1890 may include two different tools respectively configured to interface with interfaces 1840 and 1850. In one embodiment, interface 1840 is nested in interface 1850 and/or protrudes interface 1840. In this embodiment, the tool configured to interface with interface 1850 fits over interface 1840, and optionally also over the tool configured to interface with interface 1840. FIG. 18D shows one such example of implant system 1800, wherein interface 1850 is an extension of implant 1810 away from leading end 1830, and interface 1840 is a shaft coupled to screw 1820 and extending through interface 1850 in the direction away from leading end 1830. In an alternate embodiment, 1850 has an opening for inserting a tool therethrough to engage with an interface 1840 closer than interface 1850 to leading end 1830.

Although not shown in FIGS. 18A and 18B, one or both of implant 1810 and screw 1820 may be tapered, as discussed for threaded implant 500 (FIGS. 5A and 5B), without departing from the scope hereof.

Figure 19A:
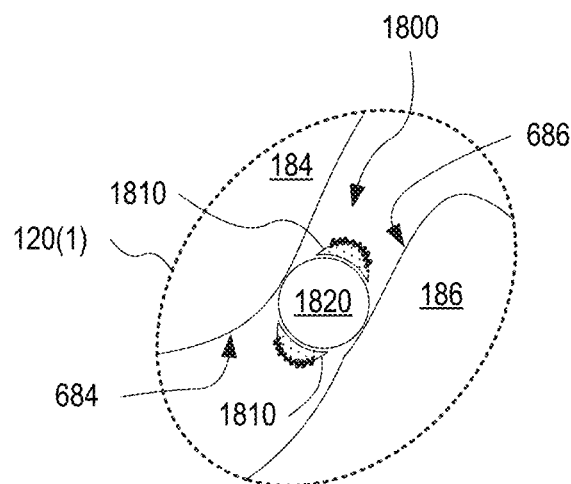
FIGS. 19A and 19B illustrate, in a posterior view, insertion of the implant of FIGS. 18A-D), using the implant system of FIGS. 18A-D, into an uncinate joint along an anterior-to-posterior direction, according to an embodiment.
Figure 19B:
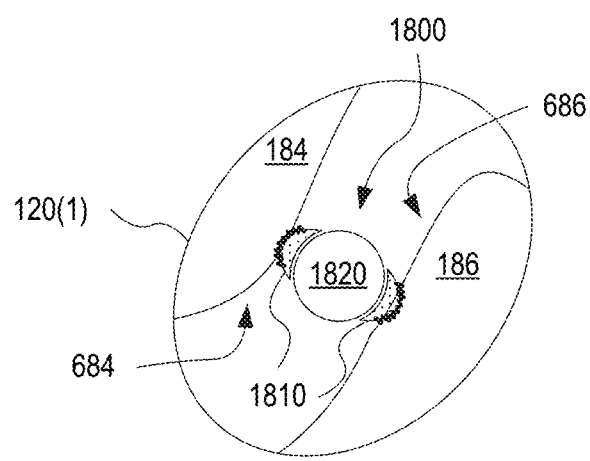

FIGS. 19A and 19B illustrate, in a posterior view, insertion of implant 1810 (FIGS. 18A-D), using implant system 1800, into uncinate joint 120 (FIG. 1) along anterior-to-posterior direction 210 (FIG. 2) according to method 400 (FIG. 4). Implant system 1800 may perform steps 420 and 430 of method 400. FIGS. 19A and 19B are best viewed together.

FIG. 19A shows implant system 1800 during insertion of implant system 1800 into uncinate joint 120 along anterior-to-posterior direction 210. During this operation, the surgeon operates tool 1890 (not shown in FIGS. 19A and 19B) to orient implant 1810 such that threads 1822 of screw 1820 are in contact with superior surface 684 (FIG. 6B) and inferior surface 686 of uncinate joint 120. The surgeon operates tool 1890 to rotate screw 1820 to screw implant system 1800 into uncinate joint 120. When implant system 1800 is in a location within uncinate joint 120, suitable for stabilizing uncinate joint 120 using implant 1810, the surgeon uses tool 1890 to rotate implant 1810, such that rough surfaces 1812 grip superior surface 684 and inferior surface 686 (see FIG. 19B). This operation secures implant 1810 to uncinate joint 120. Additionally, this operation may serve to distract uncinate joint 120 to increase the spacing between superior surface 684 and inferior surface 686. In turn, increasing the spacing between superior surface 684 and inferior surface 686 may relieve pathological issues in cervical spine segment 180, such as nerve impingement or damage to intervertebral disc 150. In one exemplary scenario, the spacing between superior surface 684 and inferior surface 686 is increased by one or several millimeters, when implant 1810 is rotated as shown in FIG. 19B.

After rotating implant 1810, as shown in FIG. 19B, the surgeon may use tool 1890 to back screw 1820 out of uncinate joint 120, along a posterior-to-anterior direction, while leaving implant 1810 in uncinate joint 120. Subsequently, the surgeon may load bone graft material into implant 1810 from trailing end 1832, and optionally seal trailing end 1832 with a cap, similar to the cap shown in FIG. 8C.

Figure 20:
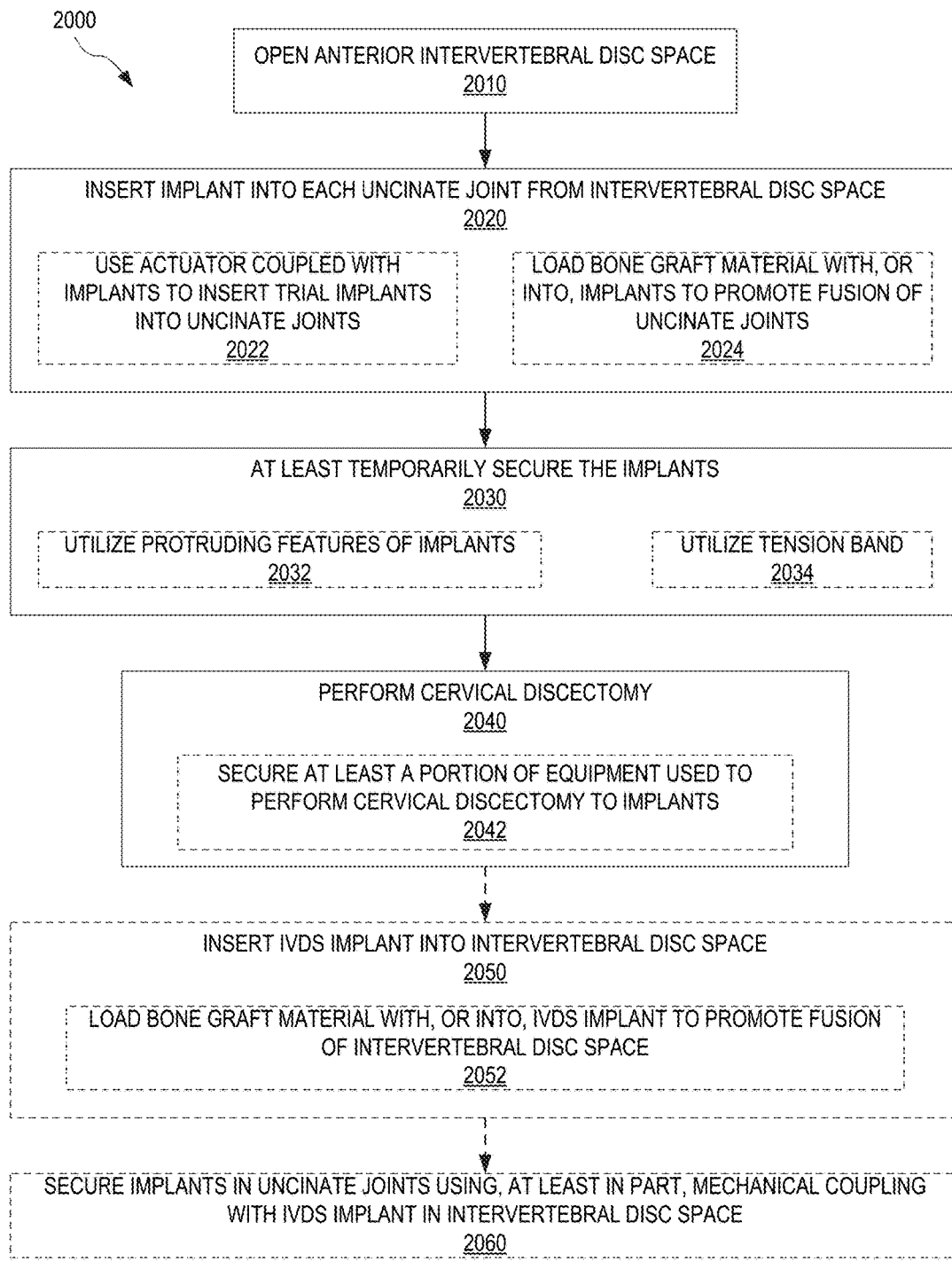
FIG. 20 illustrates a method for stabilizing the uncinate joints of a cervical spine segment, using access to the uncinate joints via medial-to-lateral directions, according to an embodiment.

FIG. 20 illustrates one exemplary method 2000 for stabilizing uncinate joints 120 (FIG. 1) of cervical spine segment 180, using access to uncinate joints 120 via medial-to-lateral directions 220 (FIG. 2). Method 2000 is an embodiment of method 300 (FIG. 3).

In a step 2010, at least an anterior portion of intervertebral disc space 140 is opened to gain access to uncinate joints 120 via medial-to-lateral directions 220. Step 2010 may utilize methods known in the art. For example, a surgeon may access intervertebral disc space 140 by (a) making a skin incision in the front of the neck, (b) making a tunnel to the spine by moving aside muscles and retracting the trachea, esophagus, and arteries, and (c) lifting and holding aside the muscles that support the front of the spine. Optionally, the surgeon screws pins into both superior cervical vertebra 184 and inferior cervical vertebra 186 and uses these pins to distract intervertebral disc space 140.

In a step 2020, for each uncinate joint 120, implant 100 is inserted into uncinate joint 120 from intervertebral disc space 140 along medial-to-lateral directions 220. Exemplary implants compatible with use in step 2020 are discussed below in reference to FIGS. 23A-26. In one embodiment, step 2020 includes a step 2022 of using an actuator coupled with implants 100 to insert implants 100 into uncinate joints 120. In one example of step 2022, a surgeon uses an actuator, holding a pair of implants 100, to insert implants 100 into uncinate joints 120 from intervertebral disc space 140. One exemplary actuator is discussed below in reference to FIGS. 27 and 28. Optionally, step 2020 includes a step 2024 of loading bone graft material with, or into, implants 100 to promote fusion of uncinate joints 120. In one example of step 2024, each implant 100 used in step 2020 has at least one void capable of accommodating bone graft material. Bone graft material may be loaded into the void(s) of each implant 100 before or after inserting implant 100 into uncinate joint 120. In another example of step 2024, at least a portion of each implant 100 is a porous portion substantially composed of bone graft material.

In a step 2030, implants 100, inserted into uncinate joints 120 in step 2020, are at least temporarily secured to respective uncinate joints 120. Step 2030 may be an integrated element of step 2020. Step 2030 may utilize self-securing embodiments of implants 100 or utilize additional hardware to secure implants 100 in uncinate joints 120. In one embodiment, step 2030 includes a step 2032 of, for each uncinate joint 120, utilizing one or more protruding features of implant 100 to grip at least one of superior surface 684 (FIG. 6B) and inferior surface 686, and thus at least temporarily securing implant 100 in uncinate joint 120. Exemplary protruding features include barbs, ribs, and surface texture. Exemplary implants compatible with step 2032 are discussed below in reference to FIGS. 23A-D, 25, and 29. Step 2030 may include a step 2034, wherein a tension band is utilized to secure each implant 100 to the corresponding uncinate joint 120. Steps 2032 and 2034 may be implemented in combination. Although not shown in FIG. 20, the actuator of step 2022 may remain coupled to implants 100 during step 2030, such that the actuator at least participates in securing implants 100 in uncinate joints 120.

In a step 2040, method 2000 performs cervical discectomy to remove intervertebral disc 150, or at least the majority thereof, from intervertebral disc space 140. Step 2040 may utilize methods and tools known in the art. Since implants 100 are located in uncinate joints 120, implants 100 prevent the surgeon from accidentally damaging the vertebral arteries 230 of patient 170. In one embodiment, step 2040 utilizes at least one of implants 100 located in uncinate joints 120, and includes a step 2042 of securing at least a portion of the equipment, used to perform the cervical discectomy, to implants 100. In one example of step 2042, at least one of implants 100 is coupled with an extension that extends outside the corresponding uncinate joint 120 in an anterior direction, and cervical discectomy equipment is attached to this at least one extension. For example, a soft-tissue retractor, used to retract soft tissue of the neck, may be attached to at least one implant 100 or extension thereof. Exemplary extensions are discussed below in reference to FIG. 28.

In one embodiment, method 2000 further includes a step 2050 subsequent to step 2040. In step 2050, an IVDS implant is inserted into intervertebral disc space 140. In one embodiment, the IVDS implant is an artificial disc device configured to preserve motion of cervical spine segment 180. In this embodiment, implants 100 may be motion-preserving as well or, alternatively, implants 100 are biodegradable/bioabsorbable and, after some time, cease to play a role in the mobility of cervical spine segment 180. In another embodiment, step 2050 promotes fusion of cervical spine segment 180 within intervertebral disc space 140. In this embodiment, step 2050 includes a step 2052 of loading bone graft material with, or into, the IVDS implant. Method 2000 may implement step 2052 together with step 2024 to achieve fusion strength and/or speed superior to that possible when fusing only intervertebral disc space 140. In one example, steps 2050 and 2052 utilize an IVDS implant that is a rigid structure with at least one void capable of accommodating bone graft material. The void(s) may be loaded with bone graft material prior to or after insertion of the IVDS implant into intervertebral disc space 140. In another example, steps 2050 and 2052 utilize an IVDS implant that is or includes a porous element substantially composed of bone graft material. In yet another example, the IVDS implant of steps 2050 and 2052 is a bag with bone graft material. The use of a non-rigid IVDS implant, such as a bag, in step 2050 is facilitated by stabilizing uncinate joints 120 through steps 2020 and 2030.

In certain embodiments, the IVDS implant of step 2050 is not load bearing in cervical spine segment 180, or carries only a fraction of the load. These embodiments are facilitated by the load bearing capacity of implants 100 inserted into uncinate joints 120 in step 2020. This is in contrast to conventional intervertebral cages that must be configured to carry the load of cervical spine segment 180, which imposes significant requirements on how the conventional intervertebral cages contact cervical vertebrae 184 and 186. In comparison, a non-load bearing or partial-load bearing IVDS implant, used in step 2050, may have less contact area with cervical vertebrae 184 and 186, for example.

Figure 29:
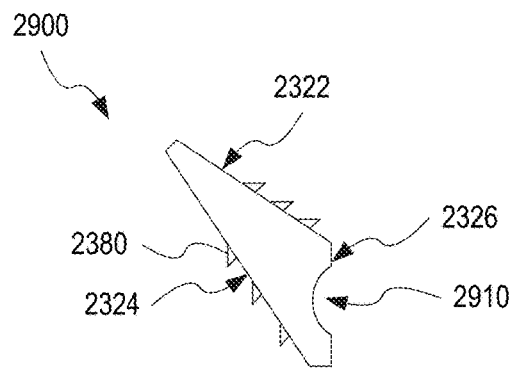
FIG. 29 illustrates a tapered implant for stabilizing an uncinate joint, according to an embodiment.
Figure 30:
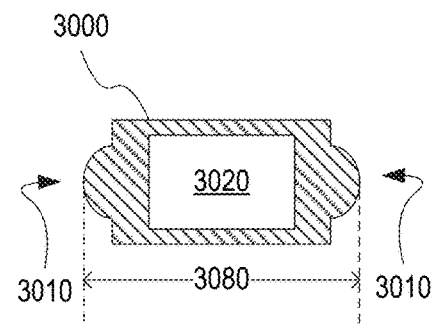
FIG. 30 illustrates an intervertebral-disc-space implant configured for placement in the intervertebral disc space of a cervical spine segment to at least participate in securing a pair of tapered implants in the uncinate joints of the cervical spine segment, according to an embodiment.
Figure 31:
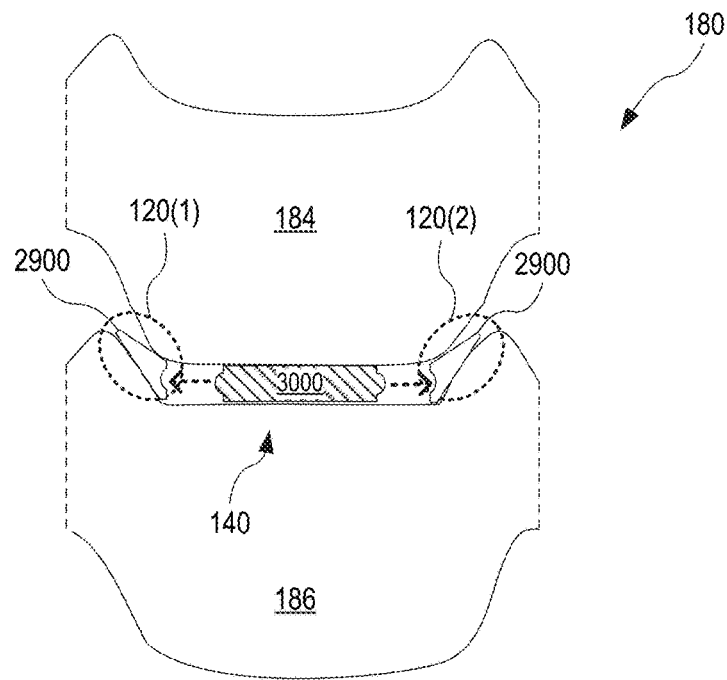
FIG. 31 illustrates use of the intervertebral-disc-space implant of FIG. 30 in the method of FIG. 20 or in the method of FIG. 22, according to an embodiment.

Optionally, step 2050 is followed by a step 2060 of securing implants 100 (inserted into uncinate joints 120 in step 2020) using, at least in part, mechanical coupling with an IVDS implant inserted into intervertebral disc space 140 in step 2052. For example, this IVDS implant may contact implants 100 to prevent implants 100 from migrating towards intervertebral disc space 140. In one exemplary scenario, intervertebral disc 150 participates in the tension band of step 2034. After cervical discectomy in step 2040, the tension band may be loosened and it may be preferred to employ additional measures to secure implants 100 in uncinate joints 120. Step 2060 serves to provide such measures. FIGS. 29-31, discussed below, illustrate one exemplary embodiment of implant 100 and one exemplary IVDS implant, which are compatible with step 2060. Without departing from the scope hereof, step 2052 may be performed after step 2060. Step 2060 may utilize a non-load bearing or partial-load bearing IVDS implant.

Figure 21:
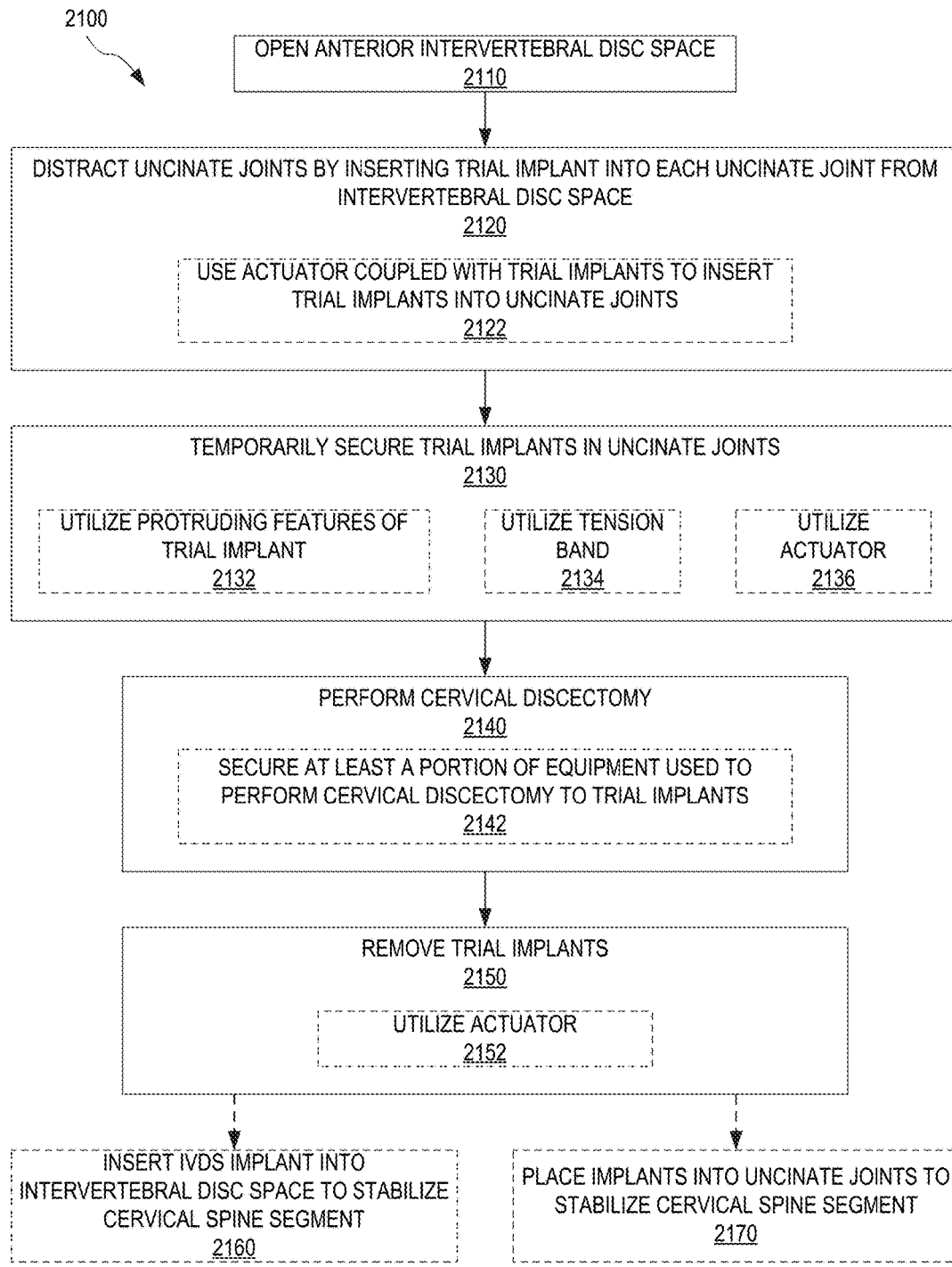
FIG. 21 illustrates a method for stabilizing the uncinate joints of a cervical spine segment at least while performing cervical discectomy, according to an embodiment.

FIG. 21 illustrates one exemplary method 2100 for stabilizing uncinate joints 120 of cervical spine segment 180 (FIG. 1) at least while performing cervical discectomy. Method 2100 accesses uncinate joints 120 from intervertebral disc space 140 along medial-to-lateral directions 220 (FIG. 2). Method 2100 is an embodiment of method 300 (FIG. 3), which utilizes temporary trial implants for at least a portion of the procedure. Trial implants are embodiments of implant 100 configured to be removable.

In a step 2110, at least an anterior portion of intervertebral disc space 140 is opened to gain access to uncinate joints 120 via medial-to-lateral directions 220. Step 2110 is similar to step 2010 of method 2000 (FIG. 20).

In a step 2120, each uncinate joint 120 is distracted by inserting a trial implant into uncinate joint 120 from intervertebral disc space 140 along medial-to-lateral direction 220. In one example of step 2120, a surgeon inserts a removable embodiment of implant 100 into each uncinate joint 120 from intervertebral disc space 140 along medial-to-lateral direction 220. Exemplary implants compatible with use in step 2020 are discussed below in reference to FIGS. 23A-26.

In a step 2130, the trial implants of step 2120 are temporarily secured in uncinate joints 120. Step 2130 may be an integrated element of step 2120. Step 2130 may utilize self-securing embodiments of implants 100. In one embodiment, step 2130 includes a step 2132 of, for each uncinate joint 120, utilizing one or more protruding features of implant 100 to grip at least one of superior surface 684 (FIG. 6B) and inferior surface 686, and thus temporarily securing the trial implant in uncinate joint 120. Exemplary protruding features include barbs, ribs, and surface texture. Exemplary implants compatible with step 2132 are discussed below in reference to FIGS. 23A-D, 25, and 29. Step 2130 may include a step 2134, wherein a tension band is utilized to secure each trial implant to the corresponding uncinate joint 120. Steps 2132 and 2134 may be implemented in combination.

In a step 2140, method 2100 performs cervical discectomy to remove intervertebral disc 150, or at least the majority thereof, from intervertebral disc space 140. Step 2140 may utilize methods and tools known in the art. Since the trial implants are located in uncinate joints 120, the trial implants prevent the surgeon from accidentally damaging the vertebral arteries 230 of patient 170. In one embodiment, step 2140 utilizes at least one of the trial implants located in uncinate joints 120, and includes a step 2142 of securing at least a portion of the equipment, used to perform the cervical discectomy, to this at least one trial implant. In one example of step 2142, at least one of the trial implants, or an extension coupled therewith, extends outside the corresponding uncinate joint 120 in an anterior direction, and cervical discectomy equipment is attached to this at least one trial implant or extension thereof. For example, a soft-tissue retractor, used to retract soft tissue of the neck, may be attached to at least one trial implant or extension thereof. Exemplary extensions are discussed below in reference to FIG. 28.

In a step 2150, the trial implants are removed from uncinate joints 120. The trial implants may be removed using methods known in the art. Step 2150 may include pulling out the trial implants using plier-type tools and/or tapping out the trial implants. Step 2150 may include breaking the trial implants.

In certain embodiments, at least a portion of method 2100 utilizes an actuator to handle the trial implants. Step 2120 may include a step 2122 of utilizing an actuator coupled with the trial implants to insert the trial implants into uncinate joints 120. In one example of step 2122, a surgeon uses an actuator, holding a pair of trial implants, to insert the trial implants into uncinate joints 120 from intervertebral disc space 140. One exemplary actuator is discussed below in reference to FIGS. 27 and 28. Step 2130 may include a step 2136 of utilizing an actuator to at least assist in securing the trial implants in uncinate joints 120. In one example of steps 2122 and 2136, the actuator used in step 2122 remains coupled with the trial implants during step 2136 to at least participate in securing the trial implants in uncinate joints 120. Step 2150 may include a step 2152 of utilizing an actuator coupled with the trial implants to remove the trial implants. Step 2150 may combine step 2152 with other removal methods such as tapping. In one example of step 2122 and 2152, the actuator used in step 2122 remains coupled with the trial implants during step 2136 to at least participate in removing the trial implants from uncinate joints 120.

In one embodiment, method 2100 further includes a step 2160 of inserting an IVDS implant into intervertebral disc space 140 to stabilize cervical spine segment 180. One example of step 2160 utilizes methods and IVDS implants known in the art.

In another embodiment, method 2100 further includes a step 2170, subsequent to step 2150, of placing implants 100 in uncinate joints 120 to stabilize uncinate joints 120 permanently or for a longer period of time, such that patient 170 leaves the procedure with implants 100 in uncinate joints 120. Method 2100 may include both of steps 2160 and 2170.

Figure 22:
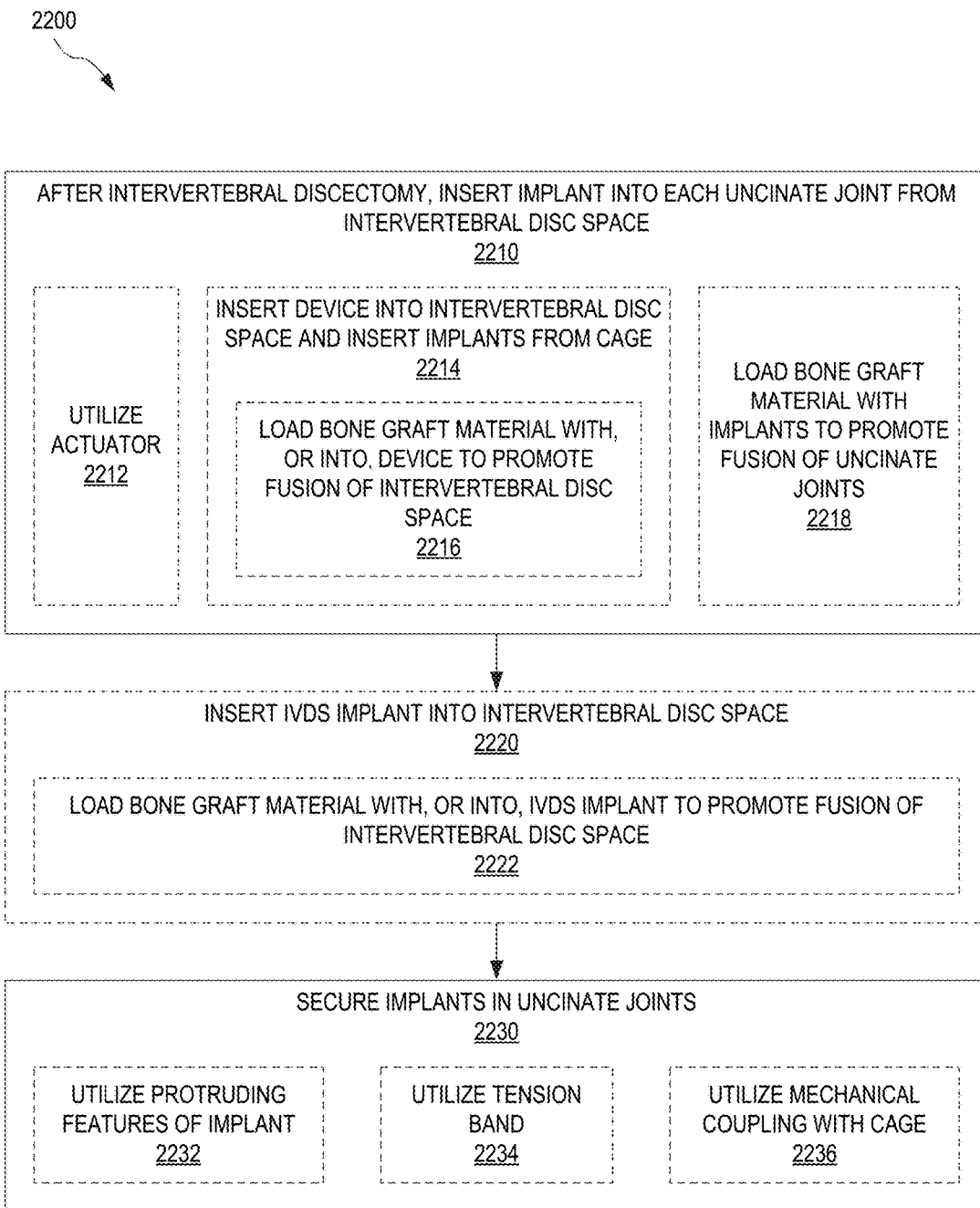
FIG. 22 illustrates a method of stabilizing the uncinate joints of a cervical spine segment after intervertebral discectomy of the cervical spine segment, according to an embodiment.

FIG. 22 illustrates one exemplary method 2200 of stabilizing uncinate joints 120 of a cervical spine segment 180 (FIG. 1) after intervertebral discectomy of cervical spine segment 180. Method 2200 accesses uncinate joints 120 from intervertebral disc space 140 along medial-to-lateral directions 220. Method 2200 may be incorporated into method 2100 (FIG. 21) to implement step 2170 and, optionally, step 2160.

In a step 2210, a pair of implants 100 is inserted from intervertebral disc space 140 into the pair of uncinate joints 120, respectively. Exemplary embodiments of implant 100, which are compatible with step 2210, are discussed below in reference to FIGS. 23A-26 and 29-31.

In one embodiment, step 2210 includes a step 2212 of utilizing an actuator to insert implants 100 into uncinate joints 120 from intervertebral disc space 140. Step 2212 is similar to step 2022 of method 2000 (FIG. 20) and may be performed as discussed in reference to step 2022.

In another embodiment, step 2210 includes a step 2214 of inserting an IVDS implant into intervertebral disc space 140 and inserting implants 100 from this IVDS implant into uncinate joints 120. This IVDS implant may be non-load bearing or partial-load bearing, as discussed in reference to FIG. 20. Examples of IVDS implants, which are compatible with step 2214, are discussed below in reference to FIGS. 32 and 33. In one implementation, step 2214 includes a step 2216 of loading bone graft material, with, or into, the IVDS implant to promote fusion of cervical spine segment 180 within intervertebral disc space 140. In one example of step 2216, the IVDS implant has at least one void capable of accommodating bone graft material. Bone graft material may be loaded into the void(s) before or after inserting the IVDS implant into intervertebral disc space 140. In another example of step 2216, the IVDS implant is or includes a porous element substantially composed of bone graft material.

Optionally, step 2210 includes a step 2218 of loading bone graft material with, or into, implants 100 to promote fusion of uncinate joints 120. In one example of step 2210, implants 100 have at least one void that carry bone graft material. Bone graft material may be loaded into the void(s) of each implant 100 before or after inserting implant 100 into uncinate joint 120. In another example of step 2210, at least a portion of each implant 100 is a porous portion substantially composed of bone graft material that promotes bone growth in the pores thereof. Since the surfaces of uncinate joints 120 are cortical bone, fusion promoted by step 2210 may be stronger and/or faster than fusion within intervertebral disc space 140. Method 2200 may implement step 2218 together with step 2216 to achieve fusion strength and/or speed superior to that possible when fusing only intervertebral disc space 140.

Embodiments of method 2200, which do not include step 2214, may include a step 2220 of inserting an IVDS implant into intervertebral disc space 140. Step 2220 is similar to step 2050 of method 2000 and may be performed as discussed in reference to step 2050.

Method 2200 further includes a step 2230 of securing implants 100 in uncinate joints 120. In one implementation, step 2230 includes a step 2232 of securing each implant 100 in the corresponding uncinate joint 120 using one or more protruding features of implant 100 to grip at least one of superior surface 684 (FIG. 6B) and inferior surface 686, and thus securing implant 100 in uncinate joint 120. Exemplary protruding features include barbs, ribs, and surface texture. Exemplary implants compatible with step 2232 are discussed below in reference to FIGS. 23A-D, 25, and 29. Step 2230 may include a step 2234, wherein a tension band is utilized to secure each implant 100 to the corresponding uncinate joint 120. In certain embodiments, step 2230 includes a step 2236 of utilizing mechanical coupling with an IVDS implant inserted into intervertebral disc space 140 in step 2214 or step 2220. Step 2236 may utilize a non-load bearing or partial-load bearing IVDS implant, as discussed in reference to FIG. 20. FIGS. 29-31 discussed below illustrate one exemplary embodiment of implant 100 and one exemplary IVDS implant, which are compatible with step 2236. In embodiments of method 2200, which implement steps 2222 and 2236, step 2222 may be performed after step 2236, without departing from the scope hereof.

Method 2000 may implement two or more of steps 2232, 2234, and 2236 in combination. Without departing from the scope hereof, method 2000 may perform step 2230 as an integrated element of step 2210 and/or step 2220.

Figure 23A:
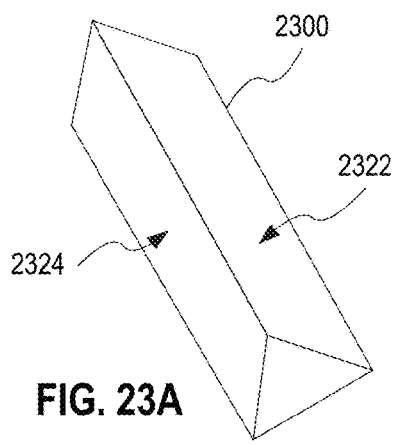
FIGS. 23A, 23B, 23C, and 23D illustrate a tapered implant for stabilizing an uncinate joint, according to an embodiment.
Figure 23B:
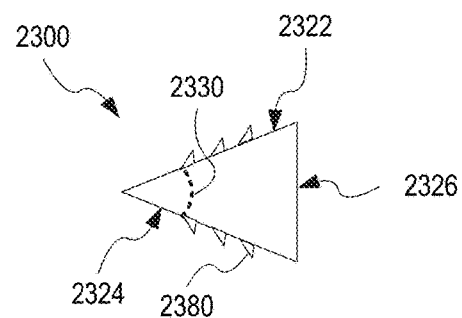
Figure 23C:
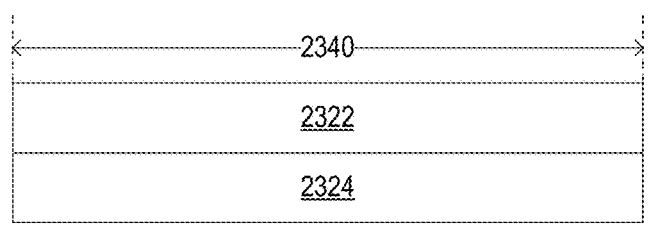
Figure 23D:
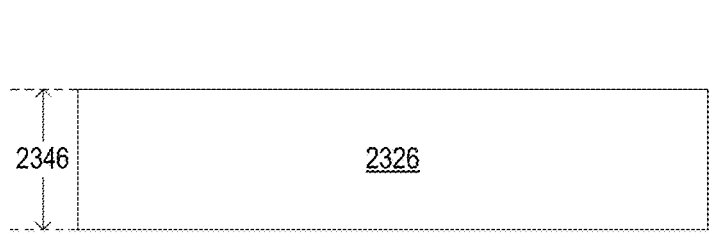

FIGS. 23A, 23B, 23C, and 23D illustrate one exemplary tapered implant 2300 for stabilizing uncinate joint 120 (FIG. 1). Tapered implant 2300 is an embodiment of implant 100 (FIG. 1). Tapered implant 2300 may be implemented in method 2000 (FIG. 20), in method 2100 (FIG. 21) as the trial implant or the implant of step 2170, or in method 2200 (FIG. 22). FIG. 23A shows tapered implant 2300 in perspective view. FIG. 23B shows tapered implant 2300 in cross-sectional side view. FIGS. 23C and 23D are elevation views of tapered implant 2300 from directions in the plane of the cross-sectional view of FIG. 23B. FIGS. 23A-D are best viewed together.

Tapered implant 2300 includes two surfaces 2322 and 2324 forming a taper with a taper angle of 2330. Taper angle 2330 is, for example, in the range between 10° and 45°. Taper angles 2330 less than 10°, may result in insufficient distraction of uncinate joints 120, while taper angles 2330 greater than 45° may result in insufficient support of uncinate joint 120 and/or trouble securing tapered implant 2300 in uncinate joint 120. Tapered implant 2300 is configured to be placed in uncinate joint 120 with surfaces 2322 and 2324 contacting superior surface 684 (FIG. 6B) and inferior surface 686 of uncinate joint 120. Tapered implant 2300 includes a surface 2326 generally facing intervertebral disc space 140, when tapered implant 2300 is located in uncinate joint 120.

Tapered implant 2300 has length 2340. When placed in uncinate joint 120, length 2340 is oriented along uncinate joint 120 substantially along anterior-to-posterior direction 210. In one example, length 2340 is at least six millimeters, for example, to provide sufficient contact area, between tapered implant 2300 and surfaces of uncinate joint 120, such that tapered implant 2300 is capable of supporting the load of uncinate joint 120. Length 2340 is at most eighteen millimeters, for example, to ensure that tapered implant 2300 does not encroach on the neural foramen. In another example, length 2340 is such that tapered implant 2300 protrudes from uncinate joint 120 in the anterior direction to easy coupling of tapered implant 2300 with another device, such as the actuator or extensions discussed in reference to FIGS. 21 and 22. In this example, length 2340 may be in the range between 15 and 70 millimeters.

When implemented in method 2000, 2100, or 2200, implant 2300 is inserted into uncinate joint 120 with the taper (characterized by taper angle 2330) facing uncinate joint 120 (i.e., with surfaces 2322 and 2324 facing uncinate joint 120 and surface 2326 facing away from uncinate joint 120). Tapered implant 2300 has a maximum thickness 2346. Maximum thickness 2346 exceeds the spacing between superior surface 684 and inferior surface 686 at the locations where tapered implant 2300 contacts superior surface 684 and inferior surface 686, such that tapered implant 2300 is capable of distracting uncinate joint 120. In one embodiment, the value of maximum thickness 2346 is sufficiently large that maximum thickness 2346 exceeds a desired spacing between superior surface 684 and inferior surface 686, at the locations where tapered implant 2300 contacts superior surface 684 and inferior surface 686, for the vast majority of patients 170. This embodiment of tapered implant 2300 is suitable for use with the vast majority of patients 170 without requiring customization or custom size selection. In one example, maximum thickness 2346 is in the range between four and ten millimeters, to provide sufficient distraction of uncinate joint 120 to relieve impingement issues while fitting between cervical vertebrae 184 and 186. In another example, maximum thickness 2346 is no greater than six millimeters. In yet another example, maximum thickness 2346 is greater than two millimeters.

In certain embodiments, tapered implant 2300 includes features 2380 that protrude from surfaces 2322 and 2324 and/or form fenestrations in surfaces 2322 and 2324. Each of methods 2000, 2100, and 2200 may utilize features 2380 in steps 2032, 2132, and 2232, respectively, to secure tapered implant 2300 in uncinate joint 120. Features 2380 may be barbs, ribs, surface texture, and/or fenestrations. For clarity of illustration, features 2380 are not shown in FIGS. 23A and 23C. Embodiments of tapered implant 2300 that include features 2380 may be self-securing.

Although not shown in FIGS. 23A-D, tapered implant 2300 may have at least one void capable of accommodating bone graft material, without departing from the scope hereof. Such embodiments of tapered implant 2300 may be utilized in step 2024 of method 2000, in step 2170 of method 2100, and in step 2218 of method 2200. Tapered implant 2300 may include a coating, for example a hydroxyapatite coating, to achieve improved fixation of tapered implant 2300 to uncinate joint 120, without departing from the scope hereof.

In one embodiment, tapered implant 2300 is substantially composed of a metal such as titanium, titanium alloy, stainless steel, cobalt, chromium, or a combination thereof. In another embodiment, tapered implant 2300 includes a porous portion with pores capable of accommodating bone graft material within uncinate joint 120, or a porous portion substantially composed of bone graft material, as discussed in reference to step 2024 of method 2000, in step 2170 of method 2100, and in step 2218 of method 2200. In one example, tapered implant 2300 is substantially composed of, or includes, porous metal. In yet another embodiment, tapered implant 2300 is substantially composed of allograft bone. In a further embodiment, tapered implant 2300 is substantially composed of polymer. The polymer is, for example, polyetheretherketone (PEEK) or another polyaryletherketone (PAEK) polymer. Any of the above materials may be used in a 3-D printing process to make tapered implant 2300.

Figure 24:
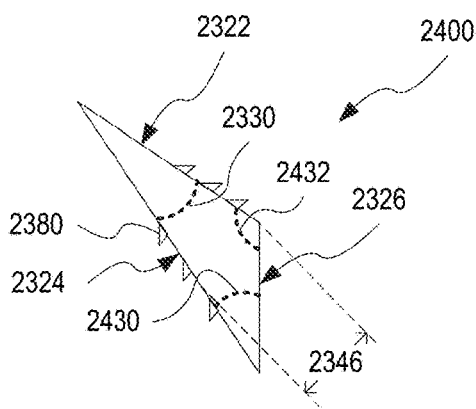
FIG. 24 illustrates another tapered implant for stabilizing an uncinate joint, according to an embodiment.

Although not shown in FIGS. 23A-D, tapered implant 2300 may further be tapered along the dimension associated with length 2340 to account for the lordosis of the cervical spine, as discussed in reference to threaded implant 500 (FIGS. 5A and 5B), without departing from the scope hereof FIG. 24 illustrates another exemplary tapered implant 2400 for stabilizing uncinate joint 120. Tapered implant 2400 is similar to tapered implant 2300, except that angle 2430 between surfaces 2324 and 2326 is less than angle 2432 between surface 2322 and 2326.

Figure 25:
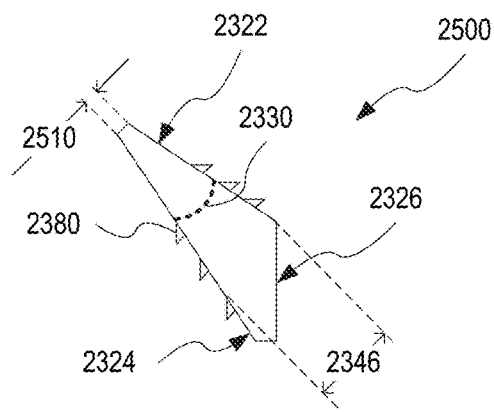
FIG. 25 illustrates yet another tapered implant for stabilizing an uncinate joint, according to an embodiment.

FIG. 25 illustrates yet another exemplary tapered implant 2500 for stabilizing uncinate joint 120. Tapered implant 2500 is similar to tapered implant 2400, except that the corner formed by surfaces 2322 and 2324 is truncated, and the corner formed by surfaces 2324 and 2326 is truncated. Tapered implant 2500 has a minimum thickness 2510. Minimum thickness 2510 may be sufficiently small that tapered implant 2500 can enter uncinate joint 120 for the vast majority of patients 170. Minimum thickness 2510 is in the range between 0.5 and 2 millimeters, for example.

Figure 26:
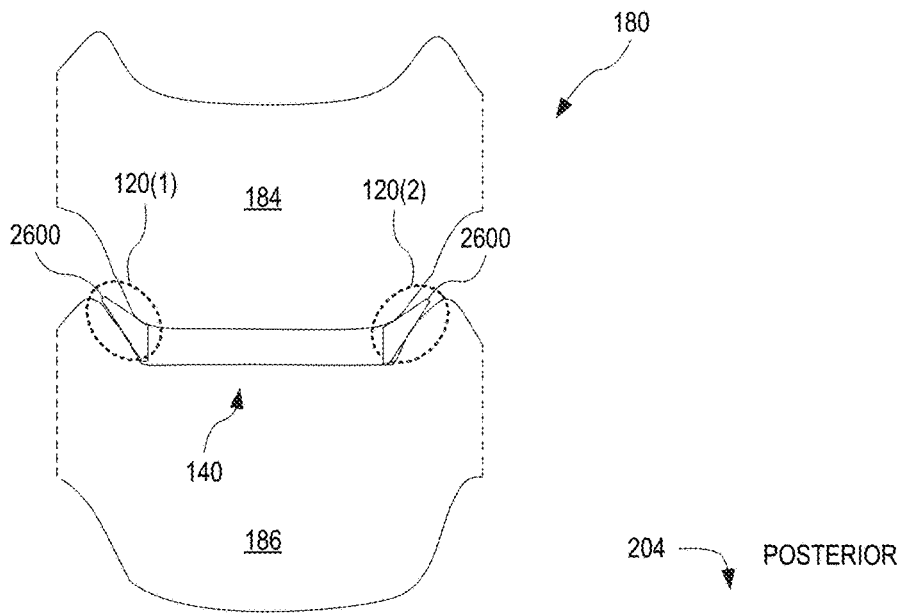
FIG. 26 illustrates, in an anterior view, a pair of tapered implants located in the uncinate joints of a cervical spine segment, after insertion into the uncinate joints according to the method of FIG. 20, the method of FIG. 21, or the method of FIG. 22, according to an embodiment.

FIG. 26 illustrates, in an anterior view, a pair of exemplary tapered implants 2600 located in uncinate joints 120 of cervical spine segment 180 (FIG. 1), after insertion into uncinate joints 120 according to method 2000 (FIG. 20), 2100 (FIG. 21), or 2200 (FIG. 22). Each tapered implant 2600 is, for example, one of tapered implants 2300 (FIG. 23), 2400 (FIGS. 24), and 2500 (FIG. 25). Tapered implant 2600 may be used as a trial implant.

Figure 27:
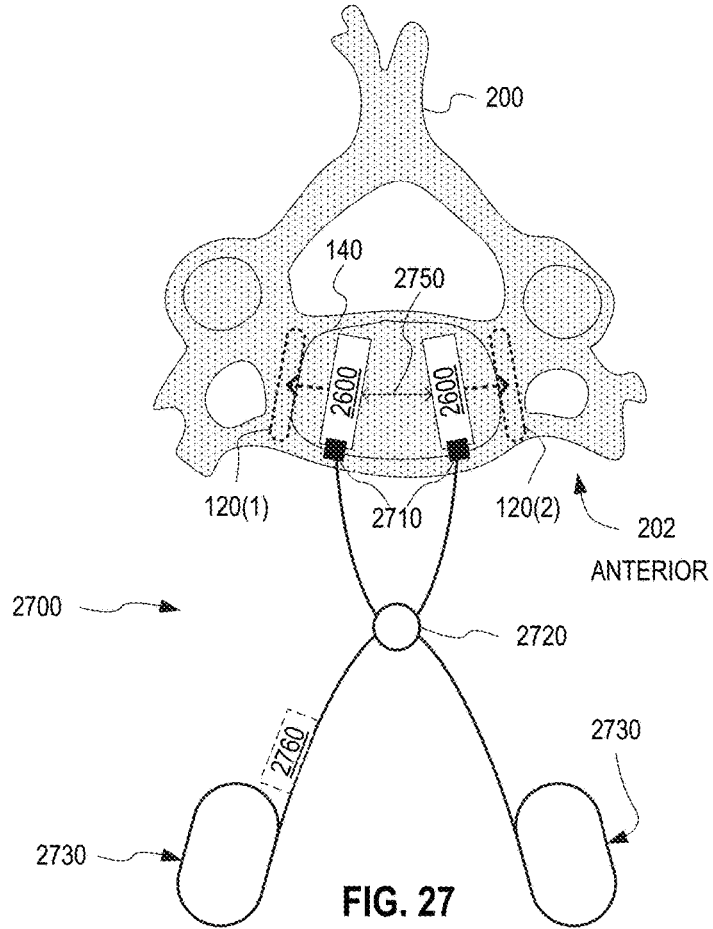
FIG. 27 illustrates, in an axial view, an actuator 2700 for inserting tapered implants into the uncinate joints of a cervical spine segment, according to an embodiment.

FIG. 27 illustrates, in an axial view, one exemplary actuator 2700 for inserting tapered implants 2600 (FIG. 26) into uncinate joints 120 of cervical spine segment 180 (FIG. 1). Actuator 2700 may be utilized by methods 2000 (FIG. 20), 2100 (FIGS. 21), and 2200 (FIG. 22). Together, actuator 2700 and tapered implants 2600 form a system for distracting uncinate joints 120. In one example of use, tapered implants 2600 are final implants left in cervical spine segment 180 to stabilize cervical spine segment 180. In another example of use, tapered implants 2600 are trial implants, and actuator 2700 and tapered implants 2600 may cooperate to perform step 2120 of method 2100. In this example of use, tapered implants 2600, or portions of tapered implants 2600 contacting a surface of uncinate joints 120, may be made of a polymer. In a more general embodiment, tapered implants 2600 is made of one or more of the materials discussed above in reference to threaded implant 500. Any one of these materials may be used to make tapered implant 2600 in a 3-D printing process.

Actuator 2700 includes a hinge 2720 and handles 2730. For the purpose of coupling with actuator 2700, each tapered implant 2600 includes a coupling interface 2710. A surgeon may manipulate handles 2730 to control the position of tapered implants 2600 through hinge 2720, to move tapered implants 2600 within cervical spine segment 180 along medial-to-lateral directions 220 (FIG. 2). In one embodiment, hinge 2720 is configured for scissor action, such that tapered implants 2600 move towards uncinate joints 120 when handles 2730 are moved away from each other. In another embodiment, hinge 2720 is configured for reverse scissor action, such that tapered implants 2600 move towards uncinate joints 120 when handles 2730 are towards each other.

Optionally, actuator 2700 includes a dial 2760 that indicates, to the surgeon, distance 2750 between tapered implants 2600 or another measure related to distance 2750. With knowledge of the shape of tapered implants 2600, other information may be derived from distance 2750, such as the spacing between superior surface 684 (FIG. 6B) and inferior surface 686. If, furthermore, a known force is applied to handles 2730, forces associated with distraction of uncinate joints 120 may be derived from distance 2750. In one example of use of dial 2760, actuator 2700 is implemented in step 2120 of method 2100 (FIG. 21) to obtain information about uncinate joints 120 and/or distraction of uncinate joints 120. This information may be utilized in step 2210 of method 2200 (FIG. 22), for example to select implants of suitable geometry for cervical spine segment 180 of patient 170. In one implementation, a surgeon utilizes dial 2760 to actuate handles 2730. In this implementation, dial 2760 may be configured to be operable in discrete increments that each corresponds to a known change of distance 2750. For example, each increment of dial 2700 corresponds to a change of distance 2750 by 0.5 or 1.0 millimeters.

Although not shown in FIG. 27, tapered implants 2600 may have length 2340 (FIG. 23C) sufficient to extend beyond uncinate joints 120 in an anterior direction, when tapered implants 2600 are placed in uncinate joints 120, without departing from the scope hereof.

In addition to inserting implants 100 into uncinate joints 120, actuator 2700 may serve to maintain anterior access to intervertebral disc space 140, by holding aside the esophagus, muscles, and other tissue of patient 170.

Figure 28:
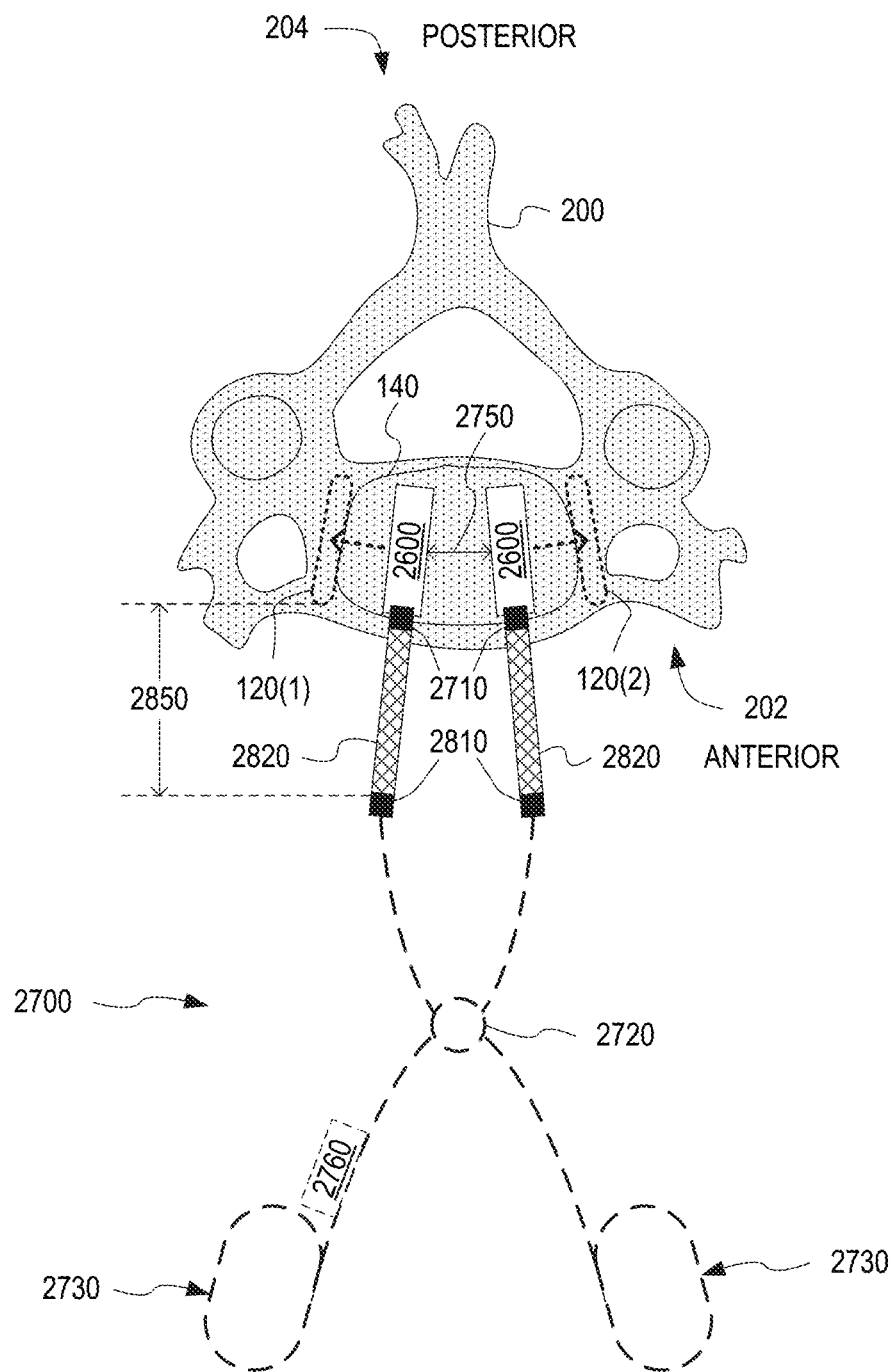
FIG. 28 illustrates, in an axial view, extensions that may be coupled with tapered implants to extend the tapered implants in an anterior direction, according to an embodiment.

FIG. 28 illustrates, in an axial view, exemplary extensions 2820 that may be coupled with tapered implants 2600 (FIG. 26) to extend tapered implants 2600 in an anterior direction. Extensions 2820 may be used by methods 2000 (FIG. 20), 2100 (FIGS. 21), and 2200 (FIG. 22).

Each extension 2820 has length 2850. Length 2850 is in the range between 20 and 60 millimeters, for example. Each extension 2820 couples to coupling interface 2710 of tapered implant 2600. Optionally, each extension 2820 includes a coupling interface 2810, such that extensions 2820 may be coupled with actuator 2700 (FIG. 27).

Actuator 2700 may be coupled with extensions 2820 to serve as a soft tissue retractor for the surgery, with or without tapered implants 2600 coupled therewith.

FIG. 29 illustrates one exemplary tapered implant 2900 for stabilizing uncinate joint 120 (FIG. 1). Tapered implant 2900 has an optional recess 2910 that facilitates mechanical coupling with an IVDS implant. Tapered implant 2900 is similar to tapered implant 2500 (FIG. 25), except for optionally including recess 2910. Without departing from the scope hereof, tapered implant 2900 may have the shape of tapered implant 2300 (FIG. 23) or tapered implant 2400 (FIG. 24), optionally modified to include recess 2910.

FIG. 30 illustrates one exemplary IVDS implant 3000 configured for placement in intervertebral disc space 140 (FIG. 1) to at least participate in securing tapered implants 2900 in uncinate joints 120. IVDS implant 3000 includes protruding features 3010 at opposing sides thereof. IVDS implant 3000 may be used in steps 2050 and 2060 of method 2000 (FIG. 20), and in steps 2220 and 2236 of method 2200 (FIG. 22). IVDS implant 3000 may be non-load bearing or partial-load bearing, as discussed in reference to FIG. 20.

IVDS implant 3000 includes a mechanism 3020 for extending distance 3080 between features 3010. Optionally, each feature 3010 is shaped to preferably couple with tapered implant 2900 in recess 2910 of tapered implant 2900 (FIG. 29). Thus, IVDS implant 3000 may couple with two tapered implants 2900.

In one embodiment, IVDS implant 3000 has at least one void capable of accommodating bone graft material to promote fusion in intervertebral disc space 140. Bone graft material may be loaded into the void(s) of IVDS implant 3000 before or after inserting IVDS implant 3000 into intervertebral disc space 140. This embodiment of IVDS implant 3000 is compatible with step 2052 of method 2000 and with step 2222 of method 2200. In another embodiment, at least a portion of IVDS implant 3000 is a porous portion substantially composed of bone graft material that promotes fusion in intervertebral disc space 140. This embodiment of IVDS implant 3000 is compatible with step 2052 of method 2000 and with step 2222 of method 2200.

FIG. 31 illustrates exemplary use of IVDS implant 3000 (FIG. 30) in step 2060 of method 2000 (FIG. 20) or in step 2236 of method 2200 (FIG. 22). FIG. 31 shows, in an anterior view, IVDS implant 3000 located in intervertebral disc space 140 of cervical spine segment 180 (FIG. 1). A pair of tapered implants 2900 (FIG. 29) are located in uncinate joints 120 of cervical spine segment 180.

Referring now to FIGS. 20 and 29-31 in combination, method 2000 inserts tapered implants 2900 into uncinate joints 120 in step 2020. In step 2050, method 2000 inserts IVDS implant 3000 into intervertebral disc space 140 (FIG. 1). In step 2060, a surgeon actuates mechanism 3020 to extend distance 3080 along medial-to-lateral directions 220 (FIG. 2) such that features 3010 apply pressure on tapered implants 2900. By virtue of this pressure, IVDS implant 3000 at least participates in securing tapered implants 2900 in uncinate joints 120.

Referring now to FIGS. 22 and 29-31 in combination, method 2200 inserts tapered implants 2900 into uncinate joints 120 in step 2210. In step 2220, method 2200 inserts IVDS implant 3000 into intervertebral disc space 140 (FIG. 1) In step 2236, a surgeon actuates mechanism 3020 to extend distance 3080 along medial-to-lateral directions 220 such that features 3010 apply pressure on tapered implants 2900. By virtue of this pressure, IVDS implant 3000 at least participates in securing tapered implants 2900 in uncinate joints 120.

Without departing from the scope hereof, features 3010 and recesses 2910 may be switched, such that tapered implants 2900 have features 3010 and IVDS implant 3000 optionally has recesses 2910.

Figure 32:
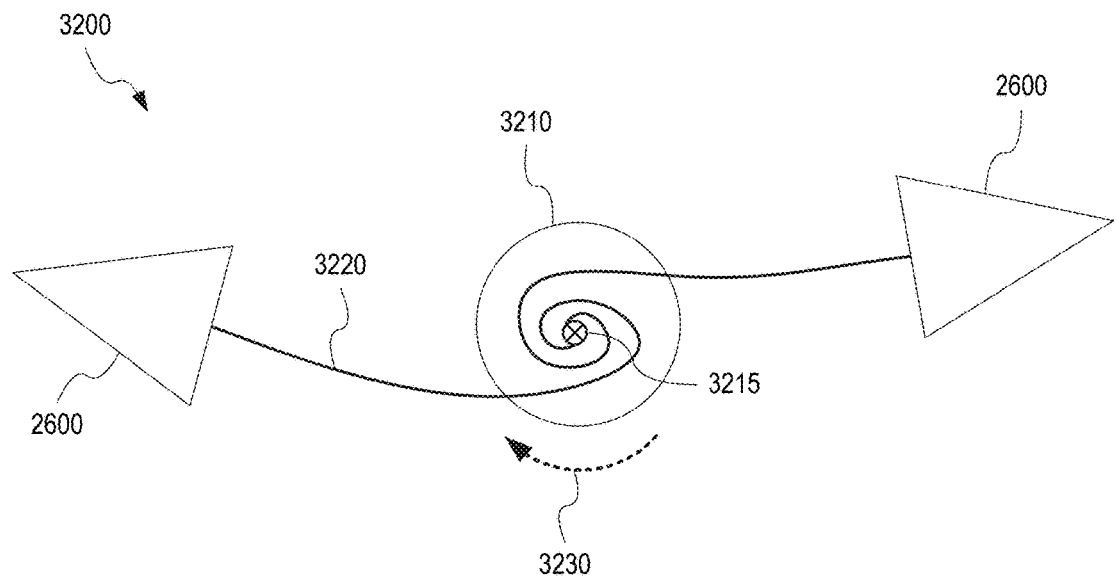
FIG. 32 illustrates an implant-loading system for stabilizing the uncinate joints of a cervical spine segment from the intervertebral disc space, according to an embodiment.

FIG. 32 illustrates one exemplary implant-loading system 3200 for stabilizing uncinate joints 120 of cervical spine segment 180 (FIG. 1) from intervertebral disc space 140. Implant-loading system 3200 may be utilized in step 2214 of method 2200 (FIG. 22).

Implant-loading system 3200 includes a cage 3210 with a rotation mechanism 3215. Implant-loading system 3200 further includes a pair of tapered implants 2600 (FIG. 26) and a pair of connectors 3220. Each connector 3220 connects a respective tapered implant 2600 to rotation mechanism 3215. Connectors 3220 are wound around rotation mechanism in a spiral pattern. Connectors 3220 may be sheets, for example made of metal, plastic, or a combination thereof. Upon clockwise rotation of rotation mechanism 3215 (as indicated by arrow 3230), tapered implants 2600 move away from cage 3210. Without departing from the scope hereof, rotation mechanism 3215 may be configured to move tapered implants 2600 away from cage 3210 upon counter-clockwise rotation of rotation mechanism 3215.

In one embodiment, cage 3210 has at least one void capable of accommodating bone graft material to promote fusion in intervertebral disc space 140. Bone graft material may be loaded into the void(s) of cage 3210 before or after inserting cage 3210 into intervertebral disc space 140. This embodiment of cage 3210 is compatible with step 2052 of method 2000 and with step 2222 of method 2200. In another embodiment, at least a portion of cage 3210 is a porous portion substantially composed of bone graft material that promotes fusion in intervertebral disc space 140. This embodiment of cage 3210 is compatible with step 2052 of method 2000 and with step 2222 of method 2200. Cage 3210 may be non-load bearing or partial-load bearing, as discussed in reference to FIG. 20.

Without departing from the scope hereof, spiral-wound connectors 3220 may be replaced by linear connectors having teeth that couple with a gear of rotation mechanism 3215.

Figure 33:
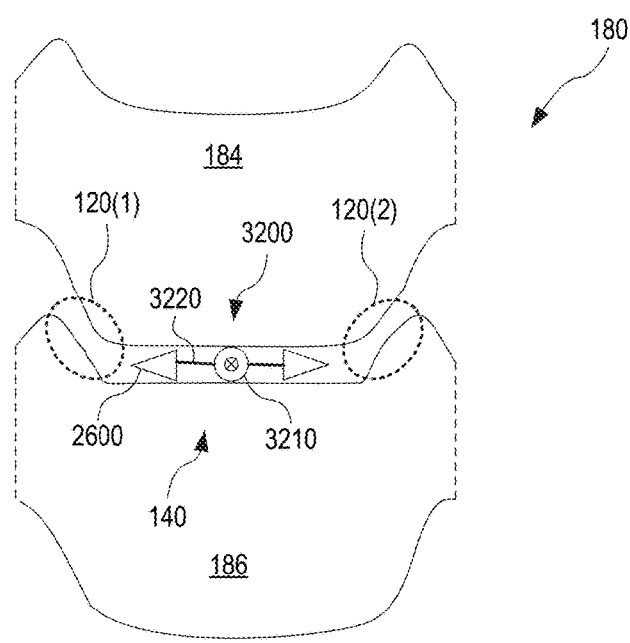
FIG. 33 shows the implant-loading system of FIG. 32 as implemented in the method of FIG. 22, according to an embodiment.

FIG. 33 shows implant-loading system 3200 (FIG. 32) as implemented in step 2214 of method 2200 (FIG. 22). Implant-loading system 3200 is inserted into intervertebral disc space 140. A surgeon rotates rotation mechanism 3215 to move tapered implants 2600 into uncinate joints 120 of cervical spine segment 180. The surgeon may utilize a tool, such as a phillips-head screwdriver/drill, a star-head screwdriver/drill, or a hexagonal wrench, to actuate rotation mechanism 3215.

Combinations of Features

Features described above as well as those claimed below may be combined in various ways without departing from the scope hereof. For example, it will be appreciated that aspects of one uncinate joint stabilizer, or associated system or method, described herein may incorporate or swap features of another uncinate joint stabilizer, or associated system or method, described herein. The following examples illustrate possible, non-limiting combinations of embodiments described above. It should be clear that many other changes and modifications may be made to the methods and device herein without departing from the spirit and scope of this invention:

(A1) A method for stabilizing a cervical spine segment may include implanting a respective uncinate joint stabilizer into each uncinate joint of the cervical spine segment to stabilize the uncinate joints and thereby stabilize the cervical spine segment.

(A2) In the method denoted as (A1), in the step of implanting, each uncinate joint stabilizer may be configured to preserve motion of the respective uncinate joint.

(A3) In the method denoted as (A1), in the step of implanting, each uncinate joint stabilizer may be configured to promote fusion of the respective uncinate joint. For example, each uncinate joint stabilizer may include bone graft material, or be configured to accept bone graft material, to promote fusion of the respective uncinate joint. Alternatively, in the step of implanting, each uncinate joint stabilizer may be composed of a non-fusing material.

(A4) In the method denoted as (A1), in the step of implanting, each uncinate joint stabilizer may be a temporary uncinate joint stabilizer composed of a biodegradable material, for temporary stabilization of the respective uncinate joint.

(A5) In any of the methods denoted as (A1) through (A4), in the step of implanting, the uncinate joint stabilizers may be configured to cooperate to bear at least a portion of load of the cervical spine segment to maintain spacing between cervical vertebrae of the cervical spine segment.

(A6) In any of the methods denoted as (A1) through (A5), the step of implanting may include inserting each uncinate joint stabilizer along an anterior-to-posterior direction.

(A7) In the method denoted as (A6), the step of inserting may include inserting each uncinate joint stabilizer into the respective uncinate joint while leaving intervertebral disc of the cervical spine segment undisturbed.

(A8) In either or both of the methods denoted as (A6) and (A7), the step of inserting may include inserting each uncinate joint stabilizer percutaneously.

(A9) In any of the methods denoted as (A6) through (A8), each uncinate joint stabilizer may be cannulated, and the step of inserting may include inserting each uncinate joint stabilizer over a guide wire.

(A10) The method denoted as (A9) may further include inserting the guide wire through longus colli muscle.

(A11) Either of both of the methods denoted as (A9) and (A10) may further include inserting the guide wire under imaging guidance.

(A12) In the method denoted as (A8), the step of inserting may include inserting each uncinate joint stabilizer through a respective cannula.

(A13) Any of the methods denoted as (A6) through (A12) may further include, during the step of inserting each uncinate joint stabilizer, monitoring, using imaging guidance, locations of (a) each uncinate joint stabilizer and (b) instrumentation used to insert each uncinate joint stabilizer.

(A14) In the method denoted as (A13), the step of monitoring may include monitoring the locations relative to vertebral artery on side of spine associated with the uncinate joint stabilizer, to prevent damaging the vertebral artery.

(A15) Any of the methods denoted as (A6) through (A14) may further include distracting each uncinate joint.

(A16) In the method denoted as (A15), the step of distracting may include distracting each uncinate joint using a distraction tool, and removing the distraction tool from the uncinate joint prior to the step of implanting.

(A17) In the method denoted as (A15), the step of distracting may include distracting each uncinate joint using the respective uncinate joint stabilizer during the step of inserting.

(A18) In any of the methods denoted as (A6) through (A17), each uncinate joint stabilizer may have threads, and the step of inserting may include threading each uncinate joint stabilizer into the respective uncinate joint using the threads.

(A19) The method denoted as (A18) may further include (a) in the step of threading, threading each uncinate joint stabilizer into the respective uncinate joint such that the threads contact uncinate joint surfaces only of a selected one of superior and inferior vertebral bodies of the cervical spine segment, and (b) securing each uncinate joint stabilizer to only the selected one of superior and inferior vertebral bodies to preserve motion of the cervical spine segment.

(A20) In the method denoted as (A19), the step of securing may include utilizing tension band formed by at least one ligament of the cervical spine segment.

(A21) In either or both of the methods denoted as (A19) and (A20), the step of securing may include, for each uncinate joint stabilizer, affixing mounting hardware to the uncinate joint stabilizer and the vertebral body.

(A22) In the method denoted as (A18), in the step of inserting, and for each uncinate joint, the threads may contact both superior and inferior surfaces of the uncinate joint.

(A23) The method denoted as (A1) may further include (a) in the step of implanting, inserting each uncinate joint stabilizer into the respective uncinate joint along a medial-to-lateral direction starting from intervertebral disc space of the cervical spine segment, and (b) securing each uncinate joint stabilizer to the respective uncinate joint.

(A24) In the method denoted as (A23), in the step of inserting each uncinate joint stabilizer, each uncinate joint stabilizer may include a tapered implant element for interfacing with superior and inferior uncinate joint surfaces, and the step of inserting each uncinate joint stabilizer may include, for each uncinate joint, distracting the uncinate joint by inserting the uncinate joint stabilizer into the uncinate joint along the medial-to-lateral direction with thinner portion of the tapered implant element facing the uncinate joint.

(A25) In the method denoted as (A24), the step of securing may include securing each uncinate joint stabilizer to the respective uncinate joint using features protruding from the tapered implant element.

(A26) In either or both of the methods denoted as (A24) and (A25), the step of securing may include securing each uncinate joint stabilizer to the respective uncinate joint by, in part, utilizing tension band formed by at least one ligament associated with the respective uncinate joint.

(A27) Any of the methods denoted as (A24) through (A26) may further include, before the step of distracting, opening anterior portion of the intervertebral disc space to open access path for the uncinate joint stabilizers.

(A28) Any of the methods denoted as (A24) through (A27) may further include (a) in the step of distracting, temporarily securing each uncinate joint stabilizer to the respective uncinate joint using features protruding from the tapered implant element, (b) after the step of distracting, performing cervical discectomy to remove at least a portion of intervertebral disc, (c) after the step of performing cervical discectomy, further distracting each uncinate joint by moving, along the medial-to-lateral direction, each uncinate joint stabilizer further into the respective uncinate joint, and (d) after the step of further distracting, securing each uncinate joint stabilizer to the respective uncinate joint using the features protruding from the tapered implant element.

(A29) In the method denoted as (A28), each of the steps of distracting, performing cervical discectomy, and further distracting may include moving each uncinate joint stabilizer using an actuator mechanically coupled with the uncinate joint stabilizers.

(A30) The method denoted as (A23) may further include, before the step of inserting each uncinate joint stabilizer, (a) opening anterior portion of the intervertebral disc space to open access path for tapered trial implants and (b) distracting the uncinate joints by inserting each tapered trial implant into a respective uncinate joint along the medial-to-lateral direction.

(A33) In the method denoted as (A30), the step of distracting may include using an actuator to insert each tapered trial implant into the respective uncinate joint to distract the respective uncinate joint, wherein the actuator accesses the tapered trial implants from anterior side of the cervical spine segment.

(A32) In the method denoted as (A31), the step of distracting may include using the actuator to distract both uncinate joints simultaneously.

(A33) Any of the methods denoted as (A30) through (A32) may further include temporarily securing each tapered trial implant to the respective uncinate joint using features protruding from the tapered trial implant.

(A34) Any of the methods denoted as (A30) through (A33) may further include, after the step of distracting and before the step of inserting each uncinate joint stabilizer, performing cervical discectomy to remove at least a portion of intervertebral disc of the cervical spine segment.

(A35) In the method denoted as (A34), the step of performing cervical discectomy may include mechanically coupling discectomy instrumentation to the tapered trial implants, and using the discectomy instrumentation to remove the at least a portion of intervertebral disc.

(A36) In the method denoted as (A35), the discectomy instrumentation may include a soft tissue retractor.

(A37) Any of the methods denoted as (A34) through (A36) may further include removing each tapered trial implant after the step of performing cervical discectomy, and the step of inserting each uncinate joint stabilizer further comprising distracting each uncinate joint by moving, along a medial-to-lateral direction, each uncinate joint stabilizer into the respective uncinate joint.

(A38) In any of the methods denoted as (A30) through (A37), the step of inserting each uncinate joint stabilizer may include moving the uncinate joint stabilizer using an actuator mechanically coupled with the uncinate joint stabilizers.

(A39) Any of the methods denoted as (A23) through (A38) may further include, after the step of inserting each uncinate joint stabilizer, depositing bone graft material in the intervertebral disc space to promote fusion of the cervical spine segment.

(A40) Any of the methods denoted as (A23) through (A39) may further include, after the step of inserting each uncinate joint stabilizer, placing an intervertebral-disc-space (IVDS) implant in the intervertebral disc space.

(A41) In the method denoted as (A40), the step of placing an IVDS implant may include mechanically coupling the IVDS implant with the uncinate joint stabilizers.

(A42) In the method denoted as (A41), the step of mechanically coupling may include adjusting lateral dimension of the IVDS implant to match distance between the uncinate joint stabilizers.

(A43) In any of the methods denoted as (A40) through (A42), the step of securing each uncinate joint stabilizer comprising utilizing mechanical coupling with the IVDS implant.

(B1) A system for stabilizing a cervical spine segment may include a pair of uncinate joint stabilizers for stabilizing a respective pair of uncinate joints of the cervical spine segment, wherein each uncinate joint stabilizer is elongated along a lengthwise dimension and configured for placement in the respective uncinate joint with the lengthwise dimension substantially oriented along an anterior-to-posterior direction of the cervical spine segment, and wherein each uncinate joint stabilizer has height in a heightwise dimension orthogonal to the lengthwise dimension and the height is configured to define spacing of the respective uncinate joint.

(B2) In the system denoted as (B1), the height may be in the range from two millimeters to seven millimeters, and/or the length may be in the range from six to eighteen millimeters.

(B3) In either or both of the systems denoted as (B1) and (B2), each uncinate joint stabilizer may have length in the lengthwise dimension and width in a widthwise dimension orthogonal to the lengthwise and heightwise dimensions, wherein the width is less than the length and greater than the height.

(B4) In the system denoted as (B3), the width and height may be compatible with percutaneous insertion of each uncinate joint stabilizer into the respective uncinate joint along an anterior-to-posterior direction.

(B5) In either or both of the systems denoted as (B3) and (B4), each of the width and the height may be no greater than 10 millimeters.

(B6) In any of the systems denoted as (B1) through (B5), each uncinate joint stabilizer may include a textured surface for securing the uncinate joint stabilizer to the respective uncinate joint.

(B7) In any of the systems denoted as (B1) through (B6), each uncinate joint stabilizer may be configured for insertion into the respective uncinate joint along an anterior to posterior direction; and the system may further include, for each uncinate joint stabilizer, a locking lever coupled to trailing or leading end of the uncinate joint stabilizer, wherein the interface between the uncinate joint stabilizer and the locking lever is configured to allow rotation of the locking lever about an axis in the lengthwise dimension, wherein extent of the locking lever in a first dimension transverse to the lengthwise dimension is less than the height to allow insertion of the uncinate joint stabilizer without the locking lever contacting surfaces of the respective uncinate joint, and wherein extent of the locking lever in a second dimension orthogonal to the first dimension and the lengthwise dimension is greater than the height to lock the locking lever to at least one surface of the uncinate joint by rotating the locking lever about the axis so as to secure the uncinate joint stabilizer in the respective uncinate joint.

(B8) In the system denoted as (B7), the locking lever may include a jagged surface for locking the locking lever to the at least one surface.

(B9) In either of both of the systems denoted as (B7) and (B8), when the locking lever is oriented to align the second dimension with the heightwise dimension, the locking lever may extend beyond the uncinate joint stabilizer in both directions away from the axis along the heightwise dimension to enable locking of the locking lever to both superior and inferior surfaces of the respective uncinate joint.

(B10) In either of both of the systems denoted as (B7) and (B8), when the locking lever is oriented to align the second dimension with the heightwise dimension, the locking lever may extend beyond the uncinate joint stabilizer only in one direction away from the axis along the heightwise dimension, to enable locking of the locking lever to only one of superior and inferior surfaces of the respective uncinate joint.

(B11) Any of the systems denoted as (B1) through (B6) may further include, for each uncinate joint stabilizer, a screw coupled to the uncinate joint stabilizer for threading the uncinate joint stabilizer into the respective uncinate joint along the anterior-to-posterior direction by contacting threads of the screw to at least one surface of the respective uncinate joint.

(B12) In the system denoted as (B11), each uncinate joint stabilizer may have two openings that allow the threads to contact the superior and inferior surfaces, respectively, for inserting the uncinate joint stabilizer into the respective uncinate joint by threading the screw into the respective uncinate joint, wherein the interface between the uncinate joint stabilizer and the screw allows for rotation of the uncinate joint stabilizer about axis of screw to rotate the uncinate joint stabilizer around the screw to secure the uncinate joint stabilizer to superior and inferior surfaces of the uncinate joint and define the spacing after inserting the uncinate joint stabilizer into the respective uncinate joint.

(B13) In the system denoted as (B14), each uncinate joint stabilizer having jagged exterior surfaces for securing the uncinate joint stabilizer to the superior and inferior surfaces.

(B14) In any of the systems denoted as (B1) through (B6), each uncinate joint stabilizer may include a generally cylindrical portion with cylinder axis in the lengthwise dimension, wherein the generally cylindrical portion has threads for threading the uncinate joint stabilizer into the respective uncinate joint along the anterior-to-posterior direction.

(B15) In the system denoted as (B14), the generally cylindrical portion may include a porous portion for accommodating bone graft material and bone growth.

(B16) In either or both of the systems denoted as (B14) and (B15), the threads may be interrupted by one or more fenestrations, oriented along the lengthwise direction, wherein the fenestrations are configured to accommodate one or more materials selected from the group consisting of bone graft material, bone growth, and tissue displaced from the respective uncinate joint by the uncinate joint stabilizer.

(B17) In any of the systems denoted as (B14) through (B16), each uncinate joint stabilizer may be cannulated along the cylinder axis for insertion into the respective uncinate joint over a respective guide wire.

(B18) The system denoted as (B17) may further include an interface for coupling the uncinate joint stabilizer to a drill for drilling the uncinate joint stabilizer into the respective uncinate joint over the respective guide wire.

(B19) In the system denoted as (B18), the interface may be located on an end face of the uncinate joint stabilizer, the end face generally facing along the lengthwise direction.

(B20) In any of the systems denoted as (B14) through (B19), each uncinate joint stabilizer may include a tapered portion that (a) is adjacent to the generally cylindrical portion, (b) is offset from the generally cylindrical portion in a direction along the lengthwise dimension, and (c) has decreasing extent transverse to the cylinder axis with increasing distance along the cylinder axis away from the generally cylindrical portion, such that the tapered portion eases insertion of the uncinate joint stabilizer into the respective uncinate joint along the anterior-to-posterior direction.

(B21) In any of the systems denoted as (B14) through (B20), the generally cylindrical portion may have diameter to implement the height.

(B22) In any of the systems denoted as (B14) through (B21), each uncinate joint stabilizer may be configured to expose the threads at least in two opposite-facing directions in the heightwise dimension, to secure the uncinate joint stabilizer to both superior and inferior surfaces of the respective uncinate joint using the threads.

(B23) In any of the systems denoted as (B14) through (B20), each uncinate joint stabilizer may further include comprising a housing for partly containing the generally cylindrical portion, wherein the housing includes (a) an opening from which the threads protrude in a first direction along the heightwise dimension, to allow the threads to contact a selected one of superior and inferior surfaces of the respective uncinate joint, and (b) a material portion shielding the threads from contacting a non-selected one of the superior and inferior surfaces.

(B24) In the system denoted as (B23), the material portion may include a smooth surface for contacting the non-selected one of the superior and inferior surfaces while allowing relative movement between the uncinate joint stabilizer and the non-selected one of the superior and inferior surfaces, to form a motion-preserving uncinate joint stabilizer.

(B25) The system denoted as (B24) may further include mounting hardware for affixing each uncinate joint stabilizer to vertebra associated with the selected one of the superior and inferior surfaces.

(B26) In the system denoted as (B25), the mounting hardware may include a bracket for interconnecting the uncinate joint stabilizers externally to intervertebral disc space of the cervical spine segment.

(B27) In the system denoted as (B26), the bracket may include a portion configured to contact anterior facing surface of vertebral body associated with the selected one of the superior and inferior surfaces.

(B28) In the system denoted as (B27), the portion may include an aperture for accepting a screw at location where the portion contacts the anterior facing surface, to secure the uncinate joint stabilizers to the vertebral body using the bracket and the screw.

(B29) In the system denoted as (B28), the aperture may include a laterally oriented slot to accommodate a range of distances between the uncinate joints.

(B30) Either or both of the systems denoted as (B28) and (B29) may further include the screw.

(B31) In any of the systems denoted as (B1) through (B6), each uncinate joint stabilizer may include a tapered portion for interfacing with superior and inferior surfaces of the respective uncinate joint, wherein the tapered portion has a gradient in height along the widthwise dimension, to enable insertion of the uncinate joint stabilizer into the respective uncinate joint from intervertebral disc space of the cervical spine segment.

(B32) In the system denoted as (B31), the tapered portion may have (a) a first surface for contacting the superior surface of the respective uncinate joint and (b) a second surface for contacting the inferior surface of the respective uncinate joint, wherein each of the first and second surfaces has at least one protruding feature for securing the uncinate joint stabilizer to the respective uncinate joint.

(B33) In either or both of the systems denoted as (B31) and (B32), the tapered portion may have taper angle in range between 10° and 45°.

(B34) Any of the systems denoted as (B31) through (B33) may further include a cage configured for placement in the intervertebral disc space and for inserting, from the intervertebral disc space, the uncinate joint stabilizers into the respective uncinate joints.

(B35) The system denoted as (B34) may further include a pair of connecting elements for connecting the pair of uncinate joint stabilizers, respectively, to the cage, and an actuator, connected to each of the connecting elements, for extending the connecting elements to insert the uncinate joint stabilizers into the uncinate joints, respectively.

(B36) In any of the systems denoted as (B1) through (B35), each uncinate joint stabilizer may be composed of metal.

(B37) In the system denoted as (B36), the metal may be selected from the group consisting of titanium, titanium alloy, stainless steel, cobalt, chromium, and a combination thereof.

(B38) In any of the systems denoted as (B1) through (B35), each uncinate joint stabilizer may include a polymer.

(B39) In the system denoted as (B38), the polymer being selected from the group consisting of (a) polyetheretherketone (PEEK) and (b) other polyaryletherketone (PAEK) material.

(B40) Any of the systems denoted as (B1) through (B35) may be composed of biodegradable material or a non-fusing material.

(B41) In the system denoted as (B40), the biodegradable material may be selected from the group consisting of lactulose, proline, polyglycolic acid, a derivative of polyglycolic acid, poly-L-lactic acid, a derivative of poly-L-lactic acid, and a combination thereof.

(C1) A system for distracting uncinate joints of a cervical spine segment may include two tapered elements and an actuator configured to couple with the tapered elements and change distance between the tapered elements, to insert the tapered elements into the uncinate joints, respectively, from intervertebral disc space of the cervical spine segment.

(C2) In the system denoted as (C1), each of the tapered elements may be elongated in a lengthwise dimension and having height in a heightwise dimension orthogonal to the lengthwise dimension, wherein the height has a gradient in a widthwise dimension orthogonal to the lengthwise and heightwise dimensions to define tapering of the tapered element.

(C3) Either or both of the systems denoted as (C1) and (C2) may further include two extensions for extending the tapered elements, respectively, along the lengthwise dimension, wherein each extension has length sufficient to protrude in anterior direction from the respective uncinate joint, the actuator being coupled to the tapered elements via the extensions.

(C4) In the system denoted as (C3), each extension may include an interface for holding instrumentation for protecting soft tissue.

(C5) In either or both of the systems denoted as (C3) and (C4), each extension may be integrally formed with the respective tapered element.

(C6) In either or both of the systems denoted as (C3) and (C4), each extension may be removably coupled with the respective tapered element.

(C7) In any of the systems denoted as (C1) through (C6), each tapered element may include polymer.

(C8) In any of the systems denoted as (C1) through (C6), each tapered element may include at least one portion for contacting surfaces of the respective uncinate joint, wherein the portion is composed of polymer.

(C9) In any of the systems denoted as (C1) through (C8), the tapered elements may taper away from each other when coupled with the actuator, such that the height of each implant decreases in direction away from the other implant.

(C10) In any of the systems denoted as (C1) through (C9), each tapered element may taper from height less than one millimeter to height no greater than six millimeters.

(C11) In any of the systems denoted as (C1) through (C9), each tapered element may taper from height less than two millimeters to height greater than two millimeters.

(C12) In any of the systems denoted as (C1) through (C11), each tapered element may include features protruding from the tapered element for temporarily securing the tapered elements to the uncinate joints.

(C13) In any of the systems denoted as (C1) through (C12) further including a coupling mechanism for coupling and uncoupling the actuator with the tapered elements.

(C14) In any of the systems denoted as (C1) through (C13), the actuator may include (a) two connecting members for mechanically coupling with the tapered elements, respectively, (b) two handles for actuating the actuator, and (c) a hinge, coupled with the connecting members and the handles, for translating action of the handles to the connecting members.

(C15) In the system denoted as (C14), the hinge may be configured for reverse scissor action.

(C16) In the system denoted as (C14), the hinge may be configured for scissor action.

(C17) Any of the systems denoted as (C1) through (C16) may further include an indicator for indicating separation between the tapered elements when coupled with the actuator.

Changes may be made in the above devices, systems, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present devices, systems, and methods, which, as a matter of language, might be said to fall therebetween.

What is claimed is:

1. A system for distracting uncinate joints of a cervical spine segment, comprising:
    two tapered elements; and
    an actuator configured to couple with the tapered elements and change distance between the tapered elements, to insert the tapered elements into the uncinate joints, respectively, from an intervertebral disc space of the cervical spine segment, to fully seat the tapered elements in the respective uncinate joints.

2. The system of claim 1, each of the tapered elements being elongated in a lengthwise dimension and having height in a heightwise dimension orthogonal to the lengthwise dimension, the height having a gradient in a widthwise dimension orthogonal to the lengthwise and heightwise dimensions to define tapering of the tapered element.

3. The system of claim 2, further comprising two extensions for extending the tapered elements, respectively, along the lengthwise dimension, each extension having length sufficient to protrude in anterior direction from the respective uncinate joint, the actuator being coupled to the tapered elements via the extensions.

4. The system of claim 3, each extension being removably coupled with the respective tapered element.

5. The system of claim 1, each tapered element including polymer.

6. The system of claim 5, each tapered element including at least one portion for contacting surfaces of the respective uncinate joint, the portion being composed of polymer.

7. The system of claim 1, the tapered elements tapering away from each other when coupled with the actuator, such that the height of each tapered element decreases in direction away from the other tapered element.

8. The system of claim 7, each tapered element tapering from height less than one millimeter to height no greater than six millimeters.

9. The system of claim 7, each tapered element tapering from height less than two millimeters to height greater than two millimeters.

10. The system of claim 7, each tapered element including features protruding from the tapered element for temporarily securing the tapered elements to the uncinate joints.

11. The system of claim 1, further including a coupling mechanism for coupling and uncoupling the actuator with the tapered elements.

12. The system of claim 1, the actuator including:
two connecting members for mechanically coupling with the tapered elements, respectively;
two handles for actuating the actuator; and
a hinge, coupled with the connecting members and the handles, for translating action of the handles to the connecting members.

13. The system of claim 12, the hinge being configured for reverse scissor action.

14. The system of claim 12, the hinge being configured for scissor action.

15. The system of claim 1, further comprising an indicator for indicating separation between the tapered elements when coupled with the actuator.

* * * * *